US012790653B2

(12) United States Patent
Manohar et al.

(10) Patent No.: US 12,790,653 B2

(45) Date of Patent: Nov. 10, 2026

(54) COMPOSITIONS AND METHODS FOR DETECTION OF HUMAN PARAINFLUENZA VIRUSES 1-4 (HPIV 1-4)

(71) Applicant: Roche Molecular Systems, Inc., Pleasanton, CA (US)

(72) Inventors: Chitra Manohar, San Ramon, CA (US); Ramani S. Ravirala, Dublin, CA (US); Jingtao Sun, San Ramon, CA (US); Alison Tsan, Danville, CA (US); Michelle E. Yee, San Jose, CA (US)

(73) Assignee: Roche Molcular Systems, Inc., Pleasanton, CA (US)

( * ) Notice: Subject to any disclaimer, the term of this patent is extended or adjusted under 35 U.S.C. 154(b) by 575 days.

(21) Appl. No.: 18/275,507

(22) PCT Filed: Feb. 4, 2022

(86) PCT No.: PCT/EP2022/052689

§ 371 (c)(1),
(2) Date: Aug. 2, 2023

(87) PCT Pub. No.: WO2022/167570

PCT Pub. Date: Aug. 11, 2022

(65) Prior Publication Data

US 2024/0124946 A1 Apr. 18, 2024

Related U.S. Application Data

(60) Provisional application No. 63/146,158, filed on Feb. 5, 2021.

(51) Int. Cl.
*C12Q 1/70* (2006.01)

(52) U.S. Cl.
CPC ......... *C12Q 1/701* (2013.01); *C12Q 2600/16* (2013.01)

(58) Field of Classification Search
None
See application file for complete search history.

(56) References Cited

FOREIGN PATENT DOCUMENTS

| | | | |
|---|---|---|---|
| CN | 111926114 | A | 11/2020 |
| WO | 2006/102695 | A1 | 10/2006 |

OTHER PUBLICATIONS

International Searching Authority, International Search Report for International Patent Application No. PCT/EP2002/052689 (Aug. 11, 2022).

International Searching Authority, Written Opinion of the International Searching Authority for International Patent Application No. PCT/EP2002/052689 (Aug. 11, 2022).

Jose C. Aguilar, et al., "Detection and Identification of Human Parainfluenza Viruses 1, 2, 3, and 4 in Clinical Samples of Pediatric Patients by Multiplex Reverse Transcriptase-PCR," Journal of Clinical Microbiology 38 (3):1191-1195 (2000).

Marta E. Alvarez-Arguelles, et al., "New clinical and seasonal evidence of infections by Human Parainfluenzavirus," European Journal of Clinical Microbiology & Infectious Diseases 37:2211-2217 (2018).

S. Bellau-Pujol, et al., "Development of three multiplex RT-PCR assays for the detection of 12 respiratory RNA viruses," Journal of Virological Methods 126:53-63 (2005).

Raychel Chambers & Toru Takimoto, "Parainfluenza Viruses," Encyclopedia of Life Sciences 1-8 (2011).

Samuel Cordey, et al., "Simultaneous detection of parainfluenza viruses 1 and 3 by real-time reverse transcription-polymerase chain reaction," Journal of Virological Methods 156:166-168 (2009).

Kelly J. Henrickson, "Parainfluenza Viruses," Clinical Microbiology Reviews 16(2):242-264 (2003).

Aizhong Hu, et al., "Development of a real-time RT-PCR assay for detection and quantitation of parainfluenza virus 3," Journal of Virological Methods 130:145-148 (2005).

Rogier R. Jansen, et al., "Development and evaluation of a four-tube real time multiplex PCR assay covering fourteen respiratory viruses, and comparison to its corresponding single target counterparts," Journal of Clinical Virology 51:179-185 (2011).

James B. Mahony, "Detection of Respiratory Viruses by Molecular Methods," Clinical Microbiology Reviews 21 (4):716-747 (2008).

Raija Vainionpaa & Timo Hyypia, "Biology of Parainfluenza Viruses," Clinical Microbiology Reviews 7(2):265-275 (1994).

International Searching Authority, International Preliminary Report on Patentability for International Patent Application No. PCT/EP2002/052689 (Aug. 17, 2023).

R. Lassauniere, et al., "A novel multiplex real-time RT-PCR assay with FRET hybridization probes for the detection and quantitation of 13 respiratory viruses," Journal of Virological Methods 165:254-260 (2010).

Mahboobeh Ramezannia, et al., "Development of a multiplex real-time RT-PCR assay for detection of human parainfluenza viruses in patients with respiratory symptoms," Future Virol. 11(9):611-617 (2016).

*Primary Examiner* — Nicole Kinsey White

(74) *Attorney, Agent, or Firm* — Eric Grant Lee

(57) ABSTRACT

Methods for the rapid detection of the presence or absence of Human Parainfluenza Viruses (HPIV), including HPIV 1-4 in a biological or non-biological sample are described. The methods can include performing an amplifying step, a hybridizing step, and a detecting step. Furthermore, primers and probes targeting HPIV 1-4, and kits are provided that are designed for the detection of target regions of HPIV 1-4. Also described are kits, reaction mixtures, and oligonucleotides (e.g., primer and probe) for the amplification and detection of HPIV 1-4.

29 Claims, 46 Drawing Sheets

Specification includes a Sequence Listing.

| COU | FAM | HEX | JA270 | CY5.5 |
|---|---|---|---|---|
| HPIV2 | HPIV4 | HPIV1 | HPIV3 | GIC |

FIG. 1

| | | |
|---|---|---|
| HPIV 1 | HPIV1_FP4_OME2 | TCAGGTGTTAATTCTTGTGATCTC<2_OMe_rA>A |
| | HPIV1_RP1_A | TGACCCAGGATTCCCATTGA<t_BB_dA> |
| | HPIV1_PRB1_HEX6QC3 | <HEX_Thr>TCGTGA<BHQ_2>CATTATTCAATTTCTTCCCTACCAGTGCCA<Phos> |
| HPIV 2 | HPIV2_FP5_A | GTTAAGATATCCCTAGAGCAACTTC<t_BB_dA> |
| | HPIV2_RP5_A | TGAGTATAACTAGAAAATGCATAGGAACT<t_BB_dA> |
| | HPIV2_PRB2_COU6Q | <Coum_Thr>TTAAGT<BHQ_2>GTTGTGGCTCCATCATCTAAACGGTGTGTAAT<Phos> |
| HPIV 3 | HPIV3_FP2_A | AGCAGAAATGATCTCACAACC<t_BB_dA> |
| | HPIV3_RP2_A | GGATAGAGTCAAAGCTGCCATT<t_BB_dC> |
| | HPIV3_PRB2_JA11Q | <JA270_Thr>TTGTTGGTAAC<BHQ_2>TACATAAGAGATGCAGGTCTCGCT<Phos> |
| HPIV 4 | HPIV4_FP3_A | GGTGGTATTCAAATAGATCTTGAG<t_BB_dC> |
| | HPIV4_RP1_A | TCATTATCACCAAAAGCCCAAATATATA<t_BB_dC> |
| | HPIV4_PRB3_FAM6Q | <FAM_Thr>AGATTT<BHQ_2>TGAGAAGCACCTGGTATTTGGGCC<Phos> |

FIG. 2

| | | |
|---|---|---|
| HPIV1 | Forward Primer | HPIV1_FP4_OME2 **(200 nM)** |
| | Reverse Primer | HPIV1_RP1_A **(150 nM)** |
| | Probe | HPIV1_PRB1_HEX6Q **(75 nM)** |

| | | |
|---|---|---|
| HPIV2 | Forward Primer | HPIV2_FP5_A (150 nM) |
| | Reverse Primer | HPIV2_RP5_A (150 nM) |
| | Probe | HPIV2_PRB2_COU6Q (75 nM) |

| Condition | Primer Conc nM | Probe Conc nM |
|---|---|---|
| 1 (CONTROL) | 150 | 75 |
| 2 | 200 | 100 |
| 3 | 300 | 100 |

| | | |
|---|---|---|
| HPIV3 | Forward Primer | HPIV3_FP2_A **(200 nM)** |
| | Reverse Primer | HPIV3_RP2_A **(150 nM)** |
| | Probe | HPIV3_PRB2_JA14Q **(100 nM)** |

| | | |
|---|---|---|
| HPIV4 | Forward Primer | HPIV4_FP3_OME2 **(200 nM)** |
| | Reverse Primer | HPIV4_RP1,OME1 **(200 nM)** |
| | Probe | HPIV4_PRB3_FAM6Q **(100 nM)** |

| Assays | AV (2-plex) | HPIV (4-plex) | EV/RV | HMPV |
|---|---|---|---|---|
| **Virus Cultures** | FAM | HEX | HEX | JA270 |
| CV 229E | ND | ND | ND | ND |
| CV NL63 | ND | ND | ND | ND |
| CV OC43 | ND | ND | ND | ND |
| CV HKU1* | ND | ND | ND | ND |
| AV B | **11.3** | ND | ND | ND |
| AV E | **14.5** | ND | ND | ND |
| AV C | **23.4** | ND | ND | ND |
| AV A | **31.9** | ND | ND | ND |
| HPIV1 | ND | **19.4** | ND | ND |
| HPIV2 | ND | **21.5** | ND | ND |
| HPIV3 | ND | **19.2** | ND | ND |
| HPIV4 | ND | **26.8** | ND | ND |
| EV A | ND | ND | **13.5** | ND |
| EV B | ND | ND | **14.5** | ND |
| EV C | ND | ND | **15.7** | ND |
| EV D68 | ND | ND | **14.2** | ND |
| RV A | ND | ND | **27.3** | ND |
| HMPV | ND | ND | ND | **21.6** |
| FluA H1N1 | ND | ND | ND | ND |
| FluA H3N2 | ND | ND | ND | ND |
| FluB | ND | ND | ND | ND |
| RSV | ND | ND | ND | ND |

ND- Not Detected

FIG. 11B

| Amont of HCT-15 cells (cells/mL) | Mucin II | Albumin | NaN3 |
|---|---|---|---|
| 1.00E+05 | 0.05% | 0.25 mg/mL | 0.073% |

| Target | Oligo Type | Oligo Name | SEQ ID NO: | Sequence |
|---|---|---|---|---|
| HPIV 1 | F. Primer | HPIV1_FP4_OME2 | 1 | TCAGGTGTTAATTCTTGTGATCTC<2_OMe_rA>A |
| | R. Primer | HPIV1_RP1_A | 2 | TGACCCAGGATTCCCATTGA<t_BB_dA> |
| | Probe | HPIV1_PRB1_HEX6QC3 | 3 | <HEX_Thr>TCGTGA<BHQ_2>CATTATTCAATTTCTTCCCTACCAGTGCCA<Spc_C3> |
| HPIV 2 | F. Primer | HPIV2_FP5_A | 4 | GTTAAGATATCCCTAGAGCAACTTC<t_BB_dA> |
| | R. Primer | HPIV2_RP5_A | 5 | TGAGTATAACTAGAAAATGCATAGGAACT<t_BB_dA> |
| | Probe | HPIV2_PRB3_COU6Q | 6 | <Coum_Thr>TGGCTC<BHQ_2>CATCATCTAAACGGTGTGTAATATTTGCAGATGT<Spc_C3> |
| HPIV3 | F. Primer | HPIV3_FP4_A | 15 | GCAGAAATGATCTCACAACCATAGAAAAG<t_BB_dA> |
| | R. Primer | HPIV3_RP3_A | 16 | AGCTGCCATTCTAGTCTCAATTCCAT<t_BB_dA> |
| | Probe | HPIV3_PRB3_JA9QC3 | 17 | <JA270_Thr>CTGATTGTA<BHQ_2>TTGAAGAATGAAGCGAGACCTGCATCTCTT<Spc_C3> |
| HPIV 4 | F. Primer | HPIV4_FP3_A | 11 | GGTGGTATTCAAATAGATCTTGAG<t_BB_dC> |
| | F. Primer | HPIV4_FP8_A | 18 | AACAGATGAACGAAGAATTGCATC<t_BB_dA> |
| | R. Primer | HPIV4_RP4_A | 19 | TGTTCATTATCACCAAAAGCCCAAATAT<t_BB_dA> |
| | Probe | HPIV4_PRB3_FAM6Q | 13 | <FAM_Thr>AGATTT<BHQ_2>TGAGAAGCACCTGGTATTTGGGCC<Phos> |

FIG. 15

FIG. 18A

| Amount of HCT-15 cells (cell/mL) | Mucin II | NaN3 |
|---|---|---|
| 2.50E+04 | 0.05% | 0.073% |

COMPOSITIONS AND METHODS FOR DETECTION OF HUMAN PARAINFLUENZA VIRUSES 1-4 (HPIV 1-4)

CROSS REFERENCE TO RELATED APPLICATIONS

This patent application is the U.S. national stage application of International Patent Application No. PCT/EP2022/052689, filed Feb. 4, 2022, which claims priority to U.S. Provisional Patent Application No. U.S. 63/146,158, filed Feb. 5, 2021, all which are incorporated herewith in their entireties.

SEQUENCE LISTING

The instant patent application contains a Sequence Listing, which has been submitted electronically in CRF format and is hereby incorporated by reference in its entirety. The CRF copy, created Jun. 9, 2026, is named "P35972-US-2 SL," and is 7,304 bytes in size.

FIELD OF THE INVENTION

The present disclosure relates to the field of in vitro diagnostics. Within this field, the present invention concerns the amplification and detection of a target nucleic acid that may be present in a sample and particularly, the amplification, detection, and/or quantitation of a target nucleic acid comprising sequence variations and/or individual mutations of Human Parainfluenza Viruses 1-4 (HPIV 1-4), using primers and probes. The invention further provides reaction mixtures and kits containing primers and probes for amplification and detection of HPIV (including HPIV 1-4).

BACKGROUND OF THE INVENTION

Human Parainfluenza Viruses (HPIV) are viruses that cause human parainfluenza. HPIVs are a group of four distinct single-stranded RNA viruses belonging to the Paramyxoviridae family, known as Human parainfluenza virus type 1 (referred to as HPIV 1 or HPIV-1 or HPIV serotype 1), Human parainfluenza virus type 2 (referred to as HPIV 2 or HPIV-2 or HPIV serotype 2), Human parainfluenza virus type 3 (referred to as HPIV 3 or HPIV-3 or HPIV serotype 3), and Human parainfluenza virus type 4 (referred to as HPIV 4 or HPIV-4 or HPIV serotype 4) (i.e., collectively, HPIV 1-4 or HPIV serotypes 1-4). Together these four distinct viruses may be referred to as Human parainfluenza virus types 1-4, or HPIV 1-4. HPIV 1-4 are distinct both genetically and antigenically. The majority of their structural and biological characteristics are similar, however each HPIV 1-4 have adapted to infect humans at different ages and cause different diseases. Overall, the Paramyxoviridae family of viruses, of which HPIV 1-4 are members, is one of the most costly, in terms of disease burden and economic impact. HPIV are divided into two genera: (1) Respirovirus, which includes HPIV 1 and HPIV 3; and (2) Rubulavirus, which includes HPIV 2 and HPIV 4. HPIV 4 has also been divided into two different antigenic subgroups, 4a and 4b, on the basis of their reactivity with monoclonal antibodies. In particular, HPIV are enveloped viruses that contain non-segmented negative-strand genomic RNA. Replication of HPIV is initiate by entry by attachment, fusion, genomic transcription and replication. Subsequently, the de novo synthesized viral components are trafficked to assembly sites at the plasma membrane where newly formed virions bud out from the cell.

For all HPIV 1-4, the RNA genome is tightly associated with nucleoproteins to form a helical nucleocapsid and the viral RNA polymerase is attached to the nucleocapsid. Replication takes place entirely in the cytoplasm, and progeny virions are assembled at the plasma membrane of infected cells and released by budding. The virion consists of a filamentous nucleocapsid core surrounded by a lipid envelope with virus-specific glycoprotein spikes. In addition to containing the genome, the nucleocapsid of HPIV 1-4 also contains two other proteins, the phosphoprotein (P protein) and the large protein (L protein). The outer layer of the lipid membrane bears spike-like haemagglutinin-neuraminidase (HN) and fusion (F) glycoproteins, which extend from the surface of the virus membrane or infected cell. Underlying the viral lipid bilayer is the matrix (M) protein, which is the smallest of the major structural proteins and also the most abundant protein produced in the paramyxoviruses. The viral membrane encompasses the viral RNA, which is encapsidated with nucleoprotein (NP) to form nucleocapsids, which are attached to the polymerase complex composed of P and L proteins, to form the biologically active ribonucleocapsid. The nucleocapsid protein (or nucleoprotein or NP) is believed to be responsible (together with the P and L proteins) for RNA-dependent RNA polymerase activity. The genomic RNA of all of the parainfluenza viruses generates six separate non-overlapping polyadenylated mRNAs that encode NP, P, M, F, HN, and L proteins. The mRNA that encodes the P protein contains several additional ORFs that encode C and V (which are accessory proteins). The genome consists, in 3' to 5' order, of the leader sequence, the genes for NP, P, M, F, HN, and L, as well as the trailer sequence. Parainfluenza viruses, including HPIV 1-4, are respiratory pathogens that act as the causative agent for croup, bronchitis, and pneumonia. HPIV infections are responsible for hundreds of thousands of hospitalizations in the United States ever year. HPIVs cause serious respiratory infections, especially among children. HPIVs replicate mainly in the respiratory tract and transmit through aerosolization. In children, the most common type of illness from parainfluenza consists of rhinitis, pharyngitis, and bronchitis. However, infection in immuno-compromised patients is usually prolonged and may be even more severe. There is significant diversity in the clinical manifestations of the various types of HPIV. For example, HPIV 1 and HPIV 2 cause most cases of laryngotracheobronchitis (croup) in children (about 600,000 cases per year in the U.S.), while HPIV 3 is responsible for 3-10% of hospitalizations and usually causes bronchitis, pneumonia, croup, or pneumonia. HPIV 4 is not recognized as often, but may cause mild to severe respiratory tract illnesses. HPIVs commonly infect infants and young children and persons with weakened immune systems, however anyone can get HPIV infection. Additionally, people can get multiple HPIV infections in their lifetime. Reinfections usually cause mild upper respiratory tract illness with cold-like symptoms, however reinfections can also cause serious lower respiratory tract illness, such as pneumonia, bronchitis, and bronchiolitis in some people. Older adults and people with compromised or weakened immune systems are at higher risk for severe infections. HPIVs are usually transmitted by direct contact with infectious droplets or by airborne spread when an infected individual breathes, coughs, or sneezes. HPIVs may remain infectious in airborne droplets for over an hour and on surfaces for a few hours, as many as 10 hours. Unfortunately, there are very few, if any, effective treatments for an HPIV infection. Ribavirin is one medication that has shown to have potential efficacy against HPIV 3 infections. Moreover, there are no effective vaccines against HPIV, including any of HPIV 1-4.

Existing methods for laboratory diagnosing an HPIV infection include direct detection of viral genome by polymerase chain reaction (PCR) assay, direct detection of viral antigens in respiratory secretions (collected within 1 week of symptom onset) using immunofluorescence or enzyme immunoassay, isolation and identification of the virus in cell culture, and/or demonstration of a significant rise in HPIV-specific IgG antibodies between appropriately collected paired serum specimens or specific IgM antibodies in a single serum specimen. Throat swabs, nasopharyngeal swabs, nasal washes, and nasal aspiration have all been used successfully to recover HPIV, although the optimal method of collecting clinical samples for HPIV has not been well studied, but is believed to depend on the method of detection used (e.g., PCR or tissue culture), the age of the patient, and the general health of the patient (i.e., immunocompromised or with chronic lung disease) (see, Hendrickson, "Parainfluenza Viruses, Clin. Microbiol. Rev. 16(2):242-264 (2003)). The few studies to yield high rates of viral recovery (HPIV-1 and HPIV-3) employed nasal washes or nasal aspirates, which is recommended for optimal virus isolation. There are also methods for detecting antibodies to HPIV in samples, including enzyme-linked immunoabsorbent assay (ELISA), radioimmunoassays, HI, complement fixation, western blotting, and neutralization assays. However, the development of heterologous antibody to closely related HPIV serogroups during an HPIV infection is a persistent problem in trying to make a serological diagnosis. ELISA, radioimmunoassay, and fluoroimmunoassays have also been developed to detect HPIV antigen directly. Further, electron microscopy can easily demonstrate the presence of HPIV, however many paramyxoviruses appear the same, and use of electron microscopy if expensive. Moreover, immunofluorescence was also widely used as a means to detect HPIV in samples, however, the detection of HPIV by direct IF staining of clinical material has yielded highly variable and sometimes disappointing results. A shell vial assay, in which tissue culture is grown on slides and then centrifugation is used initially to speed viral absorption and cell infection, is another method for the rapid identification of HPIV, however sensitivity issues have been described with these techniques. HPIV RNA can be detected directly by Northern hybridization or a dot blot analysis using virus-specific probes, but these methods are time-consuming, yield inconsistent results, and lack sensitivity. The amount of HPIV RNA in many clinical samples is not sufficient to allow for detection, without either biological (tissue culture) or molecular amplification. There are some studies that have demonstrated PCR to be adequate for detecting HPIV, and a multiplex RT-PCR assay for detecting HPIV-1, HPIV-2, and HPIV-3 have been developed. Another group claims to have developed a multiplex RT-PCR assay for detection of HPIV 1-4 in samples, but this assay suffers from sensitivity issues (see, Aguilar, et al., "Detection and Identification of Human Parainfluenza Viruses 1, 2, 3, and 4 in Clinical Samples of Pediatric Patients by Multiplex Reverse Transcription-PCR," Journal of Clinical Microbiology 38(3):1191-1195 (2000)). Thus, there remains a need in the art for a quick, reliable, specific, and sensitive method for detecting and/or quantifying the presence of HPIV 1-4 in samples.

SUMMARY OF THE INVENTION

In the field of molecular diagnostics, the amplification and detection of nucleic acids is of considerable significance. Such methods can be employed to detect any number of microorganisms, such as viruses and bacteria. The most prominent and widely-used amplification technique is the Polymerase Chain Reaction (PCR). Other amplification techniques include Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification. Automated systems for PCR-based analysis often make use of a real-time detection of product amplification during the PCR process in the same reaction vessel. Key to such methods is the use of modified oligonucleotides carrying reporter groups or labels. The present invention is directed to the reliable, sensitive, and reproducible amplification and detection of Human Parainfluenza Viruses 1-4 (HPIV 1-4). The primers and probes are designed to maximize inclusivity for Human Parainfluenza Viruses 1-4 (HPIV 1-4) and exclude other viruses of the same family (Paramyxoviridae) thereby preventing cross reactivity with other templates (e.g., other viral templates). This Human Parainfluenza Viruses 1-4 (HPIV 1-4) assay may be used on the Cobas® 6800/8800 systems. The primers and probes of the present invention may be used as a multiplex target assay, to detect all four HPIV targets. The design strategy was to select conserved sequence regions from the HPIV 1-4 genomes and assess several primer and probe combinations for each target. These candidates could be used individually to detect single individual HPIV type, for example, one assay to detect HPIV 1 in a sample, one assay to detect HPIV 2 in a sample, one assay to detect HPIV 3 in a sample, and one assay to detect HPIV 4 in a sample. Alternatively, these candidates could also be used simultaneously, in a multiplex assay, to detect HPIV 1-4 in a single sample. In this way, a single assay can detect the presence of four different types of HPIV (HPIV 1-4) in a sample. If used as a multiplex assay targeting four types of HPIV (HPIV 1-4), then four different sets of primers and probes are employed (each set of primers and probe detecting HPIV 1, HPIV 2, HPIV 3, and HPIV 4). Of course, the candidates could also be used in a duplex or triplex assay, to detect two targets or three targets simultaneously, respectively. The candidates can be used in any configuration of an assay to detect anywhere between one to four HPIV targets of Human Parainfluenza Viruses 1-4 (HPIV 1-4).

Certain embodiments in the present disclosure relate to methods for the rapid detection of the presence or absence of Human Parainfluenza Viruses 1-4 (HPIV 1-4) in a biological or non-biological sample, for example, multiplex detection and quantitating of HPIV 1-4 by real-time polymerase chain reaction (PCR) in a single test tube or vessel. Embodiments include methods of detection of Human Parainfluenza Viruses 1-4 (HPIV 1-4) comprising performing at least one cycling step, which may include an amplifying step and a hybridizing step. Furthermore, embodiments include primers, probes, and kits that are designed for the detection of Human Parainfluenza Viruses 1-4 (HPIV 1-4) in a single tube or vessel.

One embodiment of the disclosure is directed to a method for detecting one or more target nucleic acids of Human Parainfluenza Viruses 1-4 (HPIV 1-4). In particular one embodiment of the disclosure is directed to a method for detecting one or more target nucleic acids of Human Parainfluenza Viruses 1-4 (HPIV 1-4) in a nasopharyngeal sample collected in Viral Collection Media/Universal Transport Media (UTM), One aspect of the disclosure is directed to a method for detecting Human Parainfluenza Virus (HPIV) in a sample, wherein the HPIV comprises Human Parainfluenza Virus Type 1 (HPIV-1), Human Parainfluenza Virus Type 2 (HPIV-2), Human Parainfluenza Virus Type 3 (HPIV-3), and/or Human Parainfluenza Virus Type 4 (HPIV-4), the method comprising: (a) performing an amplification step comprising contacting the sample with one or more set of primers to produce an amplification product of a target nucleic acid of HPIV-1, HPIV-2, HPIV-3, and/or HPIV-4, if one or more target nucleic acids of HPIV-1, HPIV-2, HPIV-3, and/or HPIV-4 is present in the sample; (b) performing a hybridization step comprising contacting one or more probes with the amplification product of the target nucleic acid of HPIV-1, HPIV-2, HPIV-3, and/or HPIV-4, if the one or more target nucleic acids of HPIV-1, HPIV-2, HPIV-3, and/or HPIV-4 is present in the sample; and (c) detecting the presence or absence of the amplification product of the target nucleic acid of HPIV-1, HPIV-2, HPIV-3, and/or HPIV-4, wherein the presence of the amplification product of the target nucleic acid of HPIV-1, HPIV-2, HPIV-3, and/or HPIV-4 is indicative of the presence of HPIV-1, HPIV-2, HPIV-3, and/or HPIV-4, respectively, in the sample, and wherein the absence of the amplification product of the target nucleic acid of HPIV-1, HPIV-2, HPIV-3, and/or HPIV-4 is indicative of the absence of HPIV-1, HPIV-2, HPIV-3, and/or HPIV-4, respectively, from the sample; and wherein the one or more set of primers and the one or more probes comprises: (1) a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO:3, or a complement thereof; and/or (2) a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO:6 or SEQ ID NO:7, or a complement thereof; and/or (3) a set of primers and a probe specific for target nucleic acids of HPIV-3, wherein the set of primers specific for target nucleic acids of HPIV-3 comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe specific for target nucleic acids of HPIV-3 comprises the nucleic acid sequence of SEQ ID NO:10 or SEQ ID NO:17, or a complement thereof; and/or (4) a set of primers and a probe specific for target nucleic acids of HPIV-4, wherein the set of primers specific for target nucleic acids of HPIV-4 comprises a first primer comprising the nucleic acid sequence of SEQ ID NO:11 or SEQ ID NO:18, or a complement thereof, a second primer comprising the nucleic acid sequence of SEQ ID NO:12 or SEQ ID NO:19, or a complement thereof; and wherein the probe specific for target nucleic acids of HPIV-4 comprises the nucleic acid sequence of SEQ ID NO:13 or SEQ ID NO:14, or a complement thereof. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In another embodiment, the one or more probes is labeled with a donor fluorescent moiety and a corresponding acceptor moiety. In another embodiment, detecting the presence or absence of the amplification product of the target nucleic acid of HPIV-1, HPIV-2, HPIV-3, and/or HPIV-4 in step (c) comprises detecting the presence or absence of fluorescent resonance energy transfer (FRET) between the donor fluorescent moiety and the acceptor moiety of the probes specific for the target nucleic acid of HPIV-1, HPIV-2, HPIV-3, and/or HPIV-4, wherein the presence or absence of fluorescence is indicative of the presence or absence of HPIV-1, HPIV-2, HPIV-3, and/or HPIV-4, respectively, in the sample.

Another aspect of the disclosure is directed to a method for simultaneously detecting one or more target nucleic acids of HPIV-1, HPIV-2, HPIV-3, and/or HPIV-4 in a sample, the method comprising: (a) performing an amplification step comprising contacting the sample with one or more set of primers to produce an amplification product of a target nucleic acid of HPIV-1, HPIV-2, HPIV-3, and/or HPIV-4, if one or more target nucleic acids of HPIV-1, HPIV-2, HPIV-3, and/or HPIV-4 is present in the sample; (b) performing a hybridization step comprising contacting one or more probes with the amplification product of the target nucleic acid of HPIV-1, HPIV-2, HPIV-3, and/or HPIV-4, if the one or more target nucleic acids of HPIV-1, HPIV-2, HPIV-3, and/or HPIV-4 is present in the sample; and (c) detecting the presence or absence of the amplification product of the target nucleic acid of HPIV-1, HPIV-2, HPIV-3, and/or HPIV-4, wherein the presence of the amplification product of the target nucleic acid of HPIV-1, HPIV-2, HPIV-3, and/or HPIV-4 is indicative of the presence of HPIV-1, HPIV-2, HPIV-3, and/or HPIV-4, respectively, in the sample, and wherein the absence of the amplification product of the target nucleic acid of HPIV-1, HPIV-2, HPIV-3, and/or HPIV-4 is indicative of the absence of HPIV-1, HPIV-2, HPIV-3, and/or HPIV-4, respectively, from the sample; and wherein the one or more set of primers and the one or more probes comprises: (1) a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO:3, or a complement thereof; and/or (2) a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO:6 or SEQ ID NO:7, or a complement thereof; and/or (3) a set of primers and a probe specific for target nucleic acids of HPIV-3, wherein the set of primers specific for target nucleic acids of HPIV-3 comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe specific for target nucleic acids of HPIV-3 comprises the nucleic acid sequence of SEQ ID NO:10 or SEQ ID NO:17, or a complement thereof; and/or (4) a set of primers and a probe specific for target nucleic acids of HPIV-4, wherein the set of primers specific for target nucleic acids of HPIV-4 comprises a first primer comprising the nucleic acid sequence of SEQ ID NO:11 or SEQ ID NO:18, or a complement thereof, a second primer comprising the nucleic acid sequence of SEQ ID NO:12 or SEQ ID NO:19, or a complement thereof; and wherein the probe specific for target nucleic acids of HPIV-4 comprises the nucleic acid sequence of SEQ ID NO:13 or SEQ ID NO:14, or a complement thereof. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In embodiment, the one or more probes is labeled with a donor fluorescent moiety and a corresponding acceptor moiety. In another embodiment, detecting the presence or absence of the amplification product of the target nucleic acid of HPIV-1, HPIV-2, HPIV-3, and/or HPIV-4 in step (c) comprises detecting the presence or absence of fluorescent resonance energy transfer (FRET) between the donor fluorescent moiety and the acceptor moiety of the probes specific for target nucleic acid of HPIV-1, HPIV-2, HPIV-3, and/or HPIV-4, wherein the presence or absence of fluorescence is indicative of the presence or absence of HPIV-1, HPIV-2, HPIV-3, and/or HPIV-4, respectively, in the sample.

Another aspect of the disclosure is directed to a method for detecting a first target nucleic acid, second target nucleic acid, third target nucleic acid, and/or fourth target nucleic acid in a sample, if the first target nucleic acid, the second target nucleic acid, the third target nucleic acid, and/or the fourth target nucleic acid is present in the sample, the method comprising: (a) performing an amplification step comprising contacting the sample with one or more set of primers to produce an amplification product of the first target nucleic acid, the second target nucleic acid, the third target nucleic acid, and/or the fourth target nucleic acid, if the first target nucleic acid, the second target nucleic acid, the third target nucleic acid, and/or the fourth target nucleic acid is present in the sample; (b) performing a hybridization step comprising contacting the one or more probes with the amplification product, if the first target nucleic acid, the second target nucleic acid, the third target nucleic acid, and/or the fourth target nucleic acid is present in the sample; and (c) detecting the presence or absence of the amplification product of the first target nucleic acid, the second target nucleic acid, the third target nucleic acid, and/or the fourth target nucleic acid, wherein the presence of the amplification product of the first target nucleic acid, the second target nucleic acid, the third target nucleic acid, and/or the fourth target nucleic acid is indicative of the presence of the first target nucleic acid, the second target nucleic acid, the third target nucleic acid, and/or the fourth target nucleic acid, respectively, in the sample, and wherein the absence of the amplification product of the first target nucleic acid, the second target nucleic acid, the third target nucleic acid, and/or the fourth target nucleic acid is indicative of the absence of the first target nucleic acid, the second target nucleic acid, the third target nucleic acid, and/or the fourth target nucleic acid, respectively, in the sample; and wherein the one or more set of primers and the one or more probes comprises: (1) a set of primers and a probe for the first target nucleic acid, wherein the set of primers for the first target nucleic acid comprises a first primer comprising the nucleic acid sequence of SEQ ID NO:1, or a complement thereof, and a second primer comprising the nucleic acid sequence of SEQ ID NO:2, or a complement thereof; and wherein the probe for the first target nucleic acid comprises the nucleic acid sequence of SEQ ID NO:3, or a complement thereof; and/or (2) a set of primers and a probe for the second target nucleic acid, wherein the set of primers for the second target nucleic acid comprises a first primer comprising the nucleic acid sequence of SEQ ID NO:4, or a complement thereof, and a second primer comprising the nucleic acid sequence of SEQ ID NO:5, or a complement thereof; and wherein the probe for the second target nucleic acid comprises the nucleic acid sequence of SEQ ID NO:6 or SEQ ID NO:7, or a complement thereof; and/or (3) a set of primers and a probe for the third target nucleic acid, wherein the set of primers for the third target nucleic acid comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe for the third target nucleic acid comprises the nucleic acid sequence of SEQ ID NO:10 or SEQ ID NO:17, or a complement thereof; and/or (4) a set of primers and a probe for the fourth target nucleic acid, wherein the set of primers for the fourth target nucleic acid comprises a first primer comprising the nucleic acid sequence of SEQ ID NO:11 or SEQ ID NO:18, or a complement thereof, and a second primer comprising the nucleic acid sequence of SEQ ID NO:12 or SEQ ID NO:19, or a complement thereof; and wherein the probe for the fourth target nucleic acid comprises the nucleic acid sequence of SEQ ID NO:13 or SEQ ID NO:14, or a complement thereof; and wherein the first target nucleic acid is a target nucleic acid of HPIV-1, wherein the second target nucleic acid is a target nucleic acid of HPIV-2, wherein the third target nucleic acid is a target nucleic acid of HPIV-3, and wherein the fourth target nucleic acid is a target nucleic acid of HPIV-4. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In another embodiment, the one or more probes is labeled with a donor fluorescent moiety and a corresponding acceptor moiety. In another embodiment, detecting the presence or absence of the amplification product of the first target nucleic acid, the second target nucleic acid, the third target nucleic acid, and/or the fourth target nucleic acid in step (c) comprises detecting the presence or absence of fluorescent resonance energy transfer (FRET) between the donor fluorescent moiety and the acceptor moiety of the probe for the first target nucleic acid, the second target nucleic acid, the third target nucleic acid, and/or the fourth target nucleic acid, wherein the presence of fluorescence is indicative of the presence of HPIV-1, HPIV-2, HPIV-3, and/or HPIV-4 in the sample, and the absence of fluorescence is indicative of the absence of HPIV-1, HPIV-2, HPIV-3, and/or HPIV-4 in the sample.

Another aspect is directed to a method for simultaneously detecting a first target nucleic acid, second target nucleic acid, third target nucleic acid, and/or fourth target nucleic acid in a sample, if the first target nucleic acid, the second target nucleic acid, the third target nucleic acid, and/or the fourth target nucleic acid is present in the sample, the method comprising: (a) performing an amplification step comprising contacting the sample with one or more set of primers to produce an amplification product of the first target nucleic acid, the second target nucleic acid, the third target nucleic acid, and/or the fourth target nucleic acid, if the first target nucleic acid, the second target nucleic acid, the third target nucleic acid, and/or the fourth target nucleic acid is present in the sample; (b) performing a hybridization step comprising contacting the one or more probes with the amplification product of the first target nucleic acid, the second target nucleic acid, the third target nucleic acid, and/or the fourth target nucleic acid, if the first target nucleic acid, the second target nucleic acid, the third target nucleic acid, and/or the fourth target nucleic acid is present in the sample; and (c) detecting the presence or absence of the amplification product of the first target nucleic acid, the second target nucleic acid, the third target nucleic acid, and/or the fourth target nucleic acid, wherein the presence of the amplification product of the first target nucleic acid, the second target nucleic acid, the third target nucleic acid, and/or the fourth target nucleic acid is indicative of the presence of the first target nucleic acid, the second target nucleic acid, the third target nucleic acid, and/or the fourth target nucleic acid, respectively, in the sample, and wherein the absence of the amplification product of the first target nucleic acid, the second target nucleic acid, the third target nucleic acid, and/or the fourth target nucleic acid is indicative of the absence of the first target nucleic acid, the second target nucleic acid, the third target nucleic acid, and/or the fourth target nucleic acid, respectively, in the sample; and wherein the one or more set of primers and the one or more probes comprises: (1) a set of primers and a probe for the first target nucleic acid, wherein the set of primers for the first target nucleic acid comprises a first primer comprising the nucleic acid sequence of SEQ ID NO:1, or a complement thereof, and a second primer comprising the nucleic acid sequence of SEQ ID NO:2, or a complement thereof; and wherein the probe for the first target nucleic acid comprises the nucleic acid sequence of SEQ ID NO:3, or a complement thereof; (2) a set of primers and a probe for the second target nucleic acid, wherein the set of primers for the second target nucleic acid comprises a first primer comprising the nucleic acid sequence of SEQ ID NO:4, or a complement thereof, and a second primer comprising the nucleic acid sequence of SEQ ID NO:5, or a complement thereof; and wherein the probe for the second target nucleic acid comprises the nucleic acid sequence of SEQ ID NO:6 or SEQ ID NO:7, or a complement thereof; (3) a set of primers and a probe for the third target nucleic acid, wherein the set of primers for the third target nucleic acid comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe for the third target nucleic acid comprises the nucleic acid sequence of SEQ ID NO:10 or SEQ ID NO:17, or a complement thereof; and (4) a set of primers and a probe for the fourth target nucleic acid, wherein the set of primers for the fourth target nucleic acid comprises a first primer comprising the nucleic acid sequence of SEQ ID NO:11 or SEQ ID NO:18, or a complement thereof, and a second primer comprising the nucleic acid sequence of SEQ ID NO:12 or SEQ ID NO:19, or a complement thereof; and wherein the probe for the fourth target nucleic acid comprises the nucleic acid sequence of SEQ ID NO:13 or SEQ ID NO:14, or a complement thereof; and wherein the first target nucleic acid is a target nucleic acid of HPIV-1, wherein the second target nucleic acid is a target nucleic acid of HPIV-2, wherein the third target nucleic acid is a target nucleic acid of HPIV-3, and wherein the fourth target nucleic acid is a target nucleic acid of HPIV-4. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In another embodiment, the one or more probes is labeled with a donor fluorescent moiety and a corresponding acceptor moiety. In another embodiment, detecting the presence or absence of the amplification product of the first target nucleic acid, the second target nucleic acid, the third target nucleic acid, and/or the fourth target nucleic acid in step (c) comprises detecting the presence or absence of fluorescent resonance energy transfer (FRET) between the donor fluorescent moiety and the acceptor moiety of the probe for the first target nucleic acid, the second target nucleic acid, the third target nucleic acid, and/or the fourth target nucleic acid, wherein the presence of fluorescence is indicative of the presence of HPIV-1, HPIV-2, HPIV-3, and/or HPIV-4 in the sample, and the absence of fluorescence is indicative of the absence of HPIV-1, HPIV-2, HPIV-3, and/or HPIV-4 in the sample.

Another aspect is directed to a kit for detecting HPIV that may be present in a sample, wherein the HPIV comprises HPIV-1, HPIV-2, HPIV-3, and/or HPIV-4, the kit comprising amplification and detection reagents, wherein the amplification and detection reagents comprise: (i) a DNA polymerase; (ii) nucleotide monomers; and (iii) one or more set of primers and one or more probes, wherein the one or more set of primers and the one or more probes comprises: (1) a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO:3, or a complement thereof; and/or (2) a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO:6 or SEQ ID NO:7, or a complement thereof; and/or (3) a set of primers and a probe specific for target nucleic acids of HPIV-3, wherein the set of primers specific for target nucleic acids of HPIV-3 comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe specific for target nucleic acids of HPIV-3 comprises the nucleic acid sequence of SEQ ID NO:10 or SEQ ID NO:17, or a complement thereof; and/or (4) a set of primers and a probe specific for target nucleic acids of HPIV-4, wherein the set of primers specific for target nucleic acids of HPIV-4 comprises a first primer comprising the nucleic acid sequence of SEQ ID NO:11 or SEQ ID NO:18, or a complement thereof, and a second primer comprising the nucleic acid sequence of SEQ ID NO:12 or SEQ ID NO:19, or a complement thereof; and wherein the probe specific for target nucleic acids of HPIV-4 comprises the nucleic acid sequence of SEQ ID NO:13 or SEQ ID NO:14, or a complement thereof. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In another embodiment, the one or more probes is labeled with a donor fluorescent moiety and a corresponding acceptor moiety.

Another aspect is directed to a kit for simultaneous detection of a target nucleic acid of HPIV-1, HPIV-2, HPIV-3, and/or HPIV-4 in a sample, if a target nucleic acid of HPIV-1, HPIV-2, HPIV-3, and/or HPIV-4 is present in the sample, the kit comprising amplification and detection reagents, wherein the amplification and detection reagents comprise: (i) a DNA polymerase; (ii) nucleotide monomers; and (iii) one or more set of primers and one or more probes, wherein the one or more set of primers and the one or more probes comprises: (1) a set of primers and a probe specific for target nucleic acids of HPIV-1, wherein the set of primers comprises a first primer comprising the nucleic acid sequence of SEQ ID NO:1, or a complement thereof, and a second primer comprising the nucleic acid sequence of SEQ ID NO:2, or a complement thereof; and wherein the probe comprises the nucleic acid sequence of SEQ ID NO:3, or a complement thereof (2) a set of primers and a probe specific for target nucleic acids of HPIV-2, wherein the set of primers comprises a first primer comprising the nucleic acid sequence of SEQ ID NO:4, or a complement thereof, and a second primer comprising the nucleic acid sequence of SEQ ID NO:5, or a complement thereof and wherein the probe comprises the nucleic acid sequence of SEQ ID NO:6 or SEQ ID NO:7, or a complement thereof (3) a set of primers and a probe specific for target nucleic acids of HPIV-3, wherein the set of primers comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe comprises the nucleic acid sequence of SEQ ID NO:10 or SEQ ID NO:17, or a complement thereof; and (4) a set of primers and a probe specific for target nucleic acids of HPIV-4, wherein the set of primers comprises a first primer comprising the nucleic acid sequence of SEQ ID NO:11 or SEQ ID NO:18, or a complement thereof, and a second primer comprising the nucleic acid sequence of SEQ ID NO:12 or SEQ ID NO:19, or a complement thereof; and wherein the probe comprises the nucleic acid sequence of SEQ ID NO:13 or SEQ ID NO:14, or a complement thereof. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In another embodiment, the one or more probes is labeled with a donor fluorescent moiety and a corresponding acceptor moiety.

Another aspect is directed to a method for detecting HPIV-1 in a sample, the method comprising: (a) performing an amplification step comprising contacting the sample with one or more set of primers to produce an amplification product of the target nucleic acid of HPIV-1, if one or more target nucleic acids of HPIV-1 is present in the sample; (b) performing a hybridization step comprising contacting one or more probes with the amplification product, if the one or more target nucleic acids of HPIV-1 is present in the sample; and (c) detecting the presence or absence of the amplification product of the target nucleic acid of HPIV-1, wherein the presence of the amplification product of the target nucleic acid of HPIV-1 is indicative of the presence of HPIV-1 in the sample, and wherein the absence of the amplification product of the target nucleic acid of HPIV-1 is indicative of the absence of HPIV-1 from the sample; and wherein the one or more set of primers and the one or more probes comprises: a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO:3, or a complement thereof. Another embodiment is directed to a method for detecting HPIV-2 in a sample, the method comprising: (a) performing an amplification step comprising contacting the sample with one or more set of primers to produce an amplification product of the target nucleic acid of HPIV-2, if one or more target nucleic acids of HPIV-2 is present in the sample; (b) performing a hybridization step comprising contacting one or more probes with the amplification product, if the one or more target nucleic acids of HPIV-2 is present in the sample; and (c) detecting the presence or absence of the amplification product of the target nucleic acid of HPIV-2, wherein the presence of the amplification product of the target nucleic acid of HPIV-2 is indicative of the presence of HPIV-2 in the sample, and wherein the absence of the amplification product of the target nucleic acid of HPIV-2 is indicative of the absence of HPIV-2 from the sample; and wherein the one or more set of primers and the one or more probes comprises: a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO:6 or SEQ ID NO:7, or a complement thereof. Another embodiment is directed to a method for detecting HPIV-3 in a sample, the method comprising: (a) performing an amplification step comprising contacting the sample with one or more set of primers to produce an amplification product of the target nucleic acid of HPIV-3, if one or more target nucleic acids of HPIV-3 is present in the sample; (b) performing a hybridization step comprising contacting one or more probes with the amplification product, if the one or more target nucleic acids of HPIV-3 is present in the sample; and (c) detecting the presence or absence of the amplification product of the target nucleic acid of HPIV-3, wherein the presence of the amplification product of the target nucleic acid of HPIV-3 is indicative of the presence of HPIV-3 in the sample, and wherein the absence of the amplification product of the target nucleic acid of HPIV-3 is indicative of the absence of HPIV-3 from the sample; and wherein the one or more set of primers and the one or more probes comprises: a set of primers and a probe specific for target nucleic acids of HPIV-3, wherein the set of primers specific for target nucleic acids of HPIV-3 comprises a first primer comprising the nucleic acid sequence of SEQ ID NO:8 or SEQ ID NO:15, or a complement thereof, and a second primer comprising the nucleic acid sequence of SEQ ID NO:9 or SEQ ID NO:16, or a complement thereof; and wherein the probe specific for target nucleic acids of HPIV-3 comprises the nucleic acid sequence of SEQ ID NO:10 or SEQ ID NO:17, or a complement thereof. Another embodiment is directed to a method for detecting HPIV-4 in a sample, the method comprising: (a) performing an amplification step comprising contacting the sample with one or more set of primers to produce an amplification product of the target nucleic acid of HPIV-4, if one or more target nucleic acids of HPIV-4 is present in the sample; (b) performing a hybridization step comprising contacting one or more probes with the amplification product, if the one or more target nucleic acids of HPIV-4 is present in the sample; and (c) detecting the presence or absence of the amplification product of the target nucleic acid of HPIV-4, wherein the presence of the amplification product of the target nucleic acid of HPIV-4 is indicative of the presence of HPIV-4 in the sample, and wherein the absence of the amplification product of the target nucleic acid of HPIV-4 is indicative of the absence of HPIV-4 from the sample; and wherein the one or more set of primers and the one or more probes comprises: a set of primers and a probe specific for target nucleic acids of HPIV-4, wherein the set of primers specific for target nucleic acids of HPIV-4 comprises a first primer comprising the nucleic acid sequence of SEQ ID NO:11 or SEQ ID NO:18, or a complement thereof, and a second primer comprising the nucleic acid sequence of SEQ ID NO:12 or SEQ ID NO:19, or a complement thereof; and wherein the probe specific for target nucleic acids of HPIV-4 comprises the nucleic acid sequence of SEQ ID NO:13 or SEQ ID NO:14, or a complement thereof. Another related embodiment is directed to a method for detecting HPIV-1, HPIV-2, HPIV-3, and/or HPIV-4 in a sample, the method comprising performing these methods. In another embodiment, the sample is a biological sample. In another embodiment, the biological sample is whole blood, respiratory specimens, nasopharyngeal samples, urine, fecal specimens, blood specimens, plasma, dermal swabs, nasal swabs, wound swabs, blood cultures, skin, and soft tissue infections. In another embodiment, the biological sample is a nasopharyngeal sample. In another embodiment, the one or more probes is labeled. In another embodiment, the one or more probes is labeled with a donor fluorescent moiety and a corresponding acceptor moiety.

Other aspects provide an oligonucleotide comprising or consisting of a sequence of nucleotides selected from SEQ ID NOs:1-19, or a complement thereof, which oligonucleotide has 100 or fewer nucleotides. In another aspect, the present disclosure provides an oligonucleotide that includes a nucleic acid having at least 70% sequence identity (e.g., at least 75%, 80%, 85%, 90% or 95%, etc.) to one of SEQ ID NOs:1-19, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 7 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

The present disclosure also provides for methods of detecting the presence or absence of HPIV (including HPIV 1-4) or HPIV (including HPIV 1-4) nucleic acid, in a biological sample from an individual. These methods can be employed to detect the presence or absence of HPIV (including HPIV 1-4) nucleic acid in plasma, for example, for use in blood screening and diagnostic testing. Additionally, the same test may be used by someone experienced in the art to assess urine and other sample types to detect and/or quantitate HPIV (including HPIV 1-4) nucleic acid. Such methods generally include performing at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of HPIV (including HPIV 1-4) nucleic acid in the sample, and wherein the absence of binding is indicative of the absence of HPIV (including HPIV 1-4) nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of HPIV (including HPIV 1-4) nucleic acid.

In a further aspect, a kit for detecting and/or quantitating one or more nucleic acids of HPIV (including HPIV 1-4) is provided. The kit can include one or more sets of primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of HPIV (including HPIV 1-4) nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting.

All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 1 shows the different probe dye labels for the various HPIV 1-4 targets used in the assay. For example, the HEX dye is dedicated to probes for HPIV 1, the COU dye is dedicated to probes for HPIV 2, the JA270 dye is dedicated to probes for HPIV 3, the FAM dye is dedicated to probes for HPIV 4, and the Cy5.5 dye is dedicated to the internal control (GIC).

FIG. 2 shows sequences of the set of primers and the probes for each of the assays for each of the four HPIV targets (HPIV 1-4). The set of primers and probe for detection of HPIV-1 includes the forward primer: HPIV1 FP4 OME2 (SEQ ID NO:1); reverse primer: HPIV RP1 A (SEQ ID NO:2); and probe: HPIV1 PRB1 HEX6QC3 (SEQ ID NO:3). The set of primers and probes for detection of HPIV-2 includes the forward primer: HPIV2 FP5 A SEQ ID NO:4); reverse primer HPIV2 RP5A (SEQ ID NO:5); and probe: HPIV2 PRB2 COU6Q (SEQ ID NO:7). The set of primers and probes for detection of HPIV-3 includes the forward primer: HPIV3 FP2 A (SEQ ID NO:8); reverse primer: HPIV RP2 A (SEQS ID NO: 9); and probe HPIV3 PRB2 JA11Q (SEQ ID NO:10). The set of primers and probes for detection of HPIV-4 includes the forward primer: HPIV4 FP3 A (SEQ ID NO:11); reverse primer: HPIV4 RP1 A (SEQ ID NO: 12); and probe: HPIV4 PRB3 FAM6Q (SEQ ID NO: 13).

FIG. 11A and FIG. 11B show the growth curves and data, respectively, of the performance of the HPIV 1-4 primers and probes simultaneously amplifying and detecting HPIV 1-4 target nucleic acids from virus eluates, in multiplex fashion, as described in Example 6, using the following oligonucleotides: HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13).

FIGS. 12B-12D demonstrate that the HPIV 1-4 oligonucleotides are able to simultaneously detect target HPIV 1-4 nucleic acids from a contrived artificial nasopharyngeal simulated clinical sample in a multiplex setting.

FIG. 15 shows sequences of a set of primers and the probes for each of the assays for each of the four HPIV targets (HPIV 1-4).

FIG. 18A shows the composition of the contrived artificial nasopharyngeal matrix eluate used in Example 12. Example 12 describes the HPIV 1-4 oligonucleotides for detecting HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19) tested in a contrived nasopharyngeal simulated clinical sample. FIG. 18B, FIG. 18C, FIG. 18D, and FIG. 18E demonstrate that the HPIV 1-4 oligonucleotides are able to simultaneously detect target HPIV 1-4 nucleic acids from a contrived artificial nasopharyngeal simulated clinical sample in a multiplex setting.

DETAILED DESCRIPTION OF THE INVENTION

Figure 3:
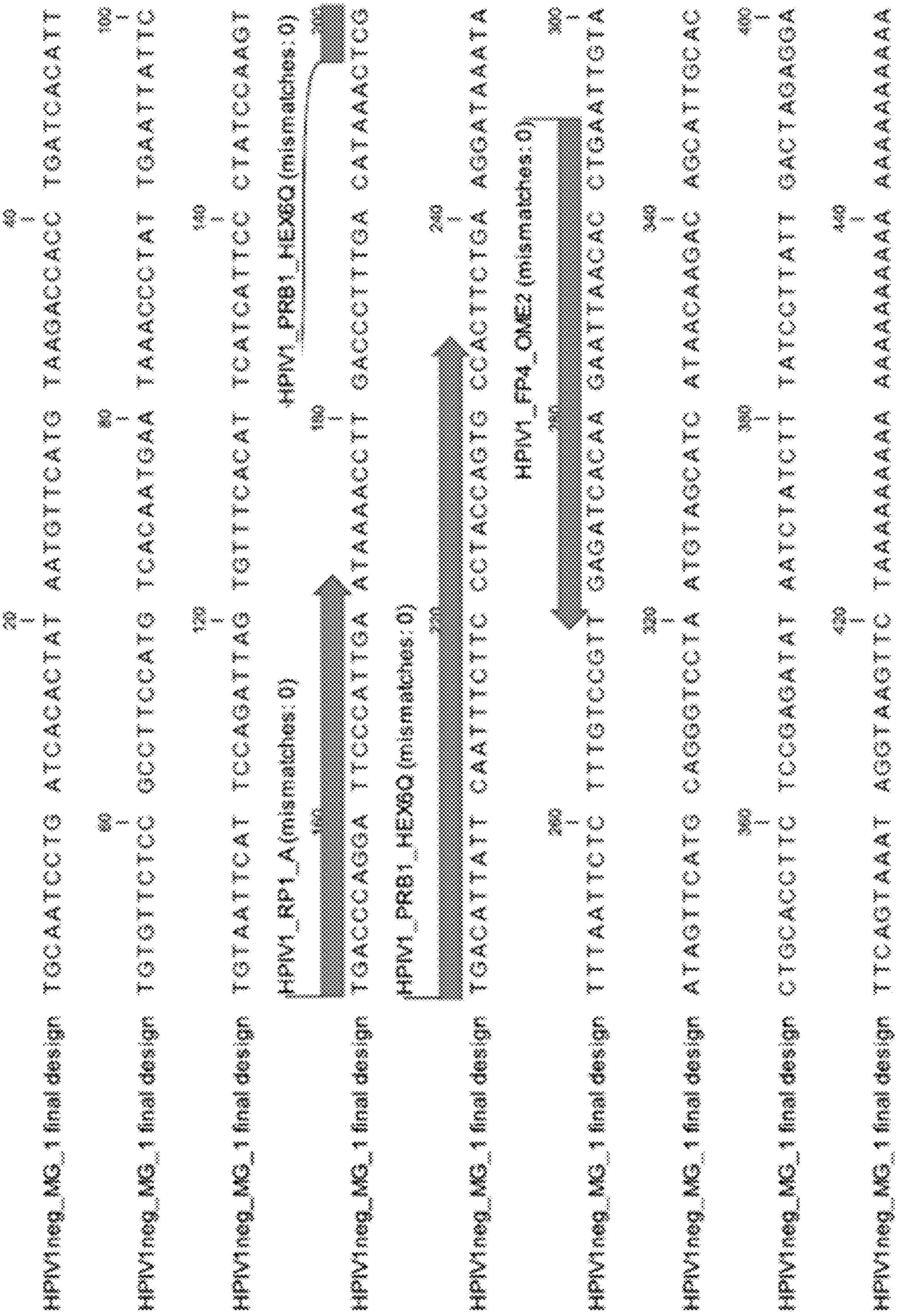
FIG. 3 shows the alignment of a set of primers (SEQ ID NOs: 1 and 2) and a probe (SEQ ID NO: 3) for amplification and detection of the HPIV 1 target (SEQ ID NO: 15).

Diagnosis of HPIV (including HPIV 1-4) infection by nucleic acid amplification provides a method for rapidly, accurately, reliably, specifically, and sensitively detecting and/or quantitating the HPIV (including HPIV 1-4) infection. A real-time PCR assay for detecting and/or quantitating HPIV (including HPIV 1-4) nucleic acids, including DNA and/or RNA, in a non-biological or biological sample is described herein. Primers and probes for detecting and/or quantitating HPIV (including HPIV 1-4) are provided, as are articles of manufacture or kits containing such primers and probes. The increased specificity and sensitivity of real-time PCR for detection of HPIV (including HPIV 1-4) compared to other methods, as well as the improved features of real-time PCR including sample containment and real-time detection and quantitating of the amplified product, make feasible the implementation of this technology for routine diagnosis of HPIV (including HPIV 1-4) infections in the clinical laboratory. Additionally, this technology may be employed for blood screening as well as for prognosis. This HPIV (including HPIV 1-4) detection assay may also be multiplexed, such that all of the oligonucleotides for detection and amplification of HPIV 1-4 are added to sample, and the oligonucleotides for HPIV 1-4 are able to amplify and detect respective target nucleic acids, if present in the sample, in parallel, simultaneously. In this way, a single sample can be assayed for the presence of four types of HPIV (HPIV 1-4) in a single reaction and reaction vessel. Such a multiplexed assay is advantageous from a cost-saving standpoint and in sample-limiting situations.

The present disclosure includes oligonucleotide primers and fluorescent labeled hydrolysis probes that hybridize to the HPIV (including HPIV 1-4) genome, in order to specifically identify HPIV (including HPIV 1-4) using, e.g., TaqMan® amplification and detection technology.

The disclosed methods may include performing at least one cycling step that includes amplifying one or more portions of the nucleic acid molecule gene target from a sample using one or more pairs of primers. "HPIV primer(s)" or "HPIV 1-4 primers" as used herein refer to oligonucleotide primers that specifically anneal to nucleic acid sequences found in the HPIV (including HPIV 1-4) genome, and initiate DNA synthesis therefrom under appropriate conditions producing the respective amplification products. Each of the discussed HPIV (including HPIV 1-4) primers anneals to a target such that at least a portion of each amplification product contains nucleic acid sequence corresponding to the target. The one or more amplification products are produced provided that one or more nucleic acid is present in the sample, thus the presence of the one or more amplification products is indicative of the presence of HPIV (including HPIV 1-4) in the sample. The amplification product should contain the nucleic acid sequences that are complementary to one or more detectable probes for HPIV (including HPIV 1-4). "HPIV probe(s)" or "HPIV 1-4 probe(s)" as used herein refer to oligonucleotide probes that specifically anneal to nucleic acid sequences found in the HPIV (including HPIV 1-4) genome. Each cycling step includes an amplification step, a hybridization step, and a detection step, in which the sample is contacted with the one or more detectable HPIV (including HPIV 1-4) probes for detection of the presence or absence of HPIV (including HPIV 1-4) in the sample.

As used herein, the term "amplifying" refers to the process of synthesizing nucleic acid molecules that are complementary to one or both strands of a template nucleic acid molecule (e.g., nucleic acid molecules from the HPIV (including HPIV 1-4) genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'—OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-O-methyl ribo-U, 2'-O-methyl ribo-C, an N4-ethyl-dC, an N6-methyl-dA, a 5-propynyl dU, a 5-propynyl dC, 7-deaza-deoxyguanosine (deaza G (u-deaza)) and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection/Quantitation of HPIV (Including HPIV 1-4) Target Nucleic Acid

The present disclosure provides methods to detect HPIV (including HPIV 1-4) by amplifying, for example, a portion of the HPIV (including HPIV 1-4) nucleic acid sequence. Specifically, primers and probes to amplify and detect and/or quantitate HPIV (including HPIV 1-4) nucleic acid molecule targets are provided by the embodiments in the present disclosure.

For detection and/or quantitation of HPIV (including HPIV 1-4), primers and probes to amplify and detect/quantitate the HPIV (including HPIV 1-4) are provided. HPIV (including HPIV 1-4) nucleic acids other than those exemplified herein can also be used to detect HPIV (including HPIV 1-4) in a sample. For example, functional variants can be evaluated for specificity and/or sensitivity by those of skill in the art using routine methods. Representative functional variants can include, e.g., one or more deletions, insertions, and/or substitutions in the HPIV (including HPIV 1-4) nucleic acids disclosed herein.

More specifically, embodiments of the oligonucleotides each include a nucleic acid with a sequence selected from SEQ ID NOs:1-19, a substantially identical variant thereof in which the variant has at least, e.g., 80%, 90%, or 95% sequence identity to one of SEQ ID NOs:1-19, or a complement of SEQ ID NOs:1-19 and the variant.

In one embodiment, the above described sets of HPIV (including HPIV 1-4) primers and probes are used in order to provide for detection of HPIV (including HPIV 1-4) in a biological sample suspected of containing HPIV (including HPIV 1-4) (Table 1). The sets of primers and probes may comprise or consist of the primers and probes specific for the HPIV (including HPIV 1-4) nucleic acid sequences, comprising or consisting of the nucleic acid sequences of SEQ ID NOs:1-19. In another embodiment, the primers and probes for the HPIV (including HPIV 1-4) target comprise or consist of a functionally active variant of any of the primers and probes of SEQ ID NOs:1-19. A functionally active variant of any of the primers and/or probes of SEQ ID NOs:1-19 may be identified by using the primers and/or probes in the disclosed methods. A functionally active variant of a primer and/or probe of any of the SEQ ID NOs:1-19 pertains to a primer and/or probe which provide a similar or higher specificity and sensitivity in the described method or kit as compared to the respective sequence of SEQ ID NOs:1-19.

TABLE 1

Oligonucleotides in HPIV 1-4 Test

| Target | Oligo Type | Oligo Name | SEQ ID NO: | Sequence |
|---|---|---|---|---|
| HPIV 1 | F. Primer | HPIV1_FP4_OME2 | 1 | TCAGGTGTTAATTCTTGTGATCTC<2_OMe_rA>A |
| | R. Primer | HPIV1_RP1_A | 2 | TGACCCAGGATTCCCATTGA<t_BB_dA> |
| | Probe | HPIV1_PRB1_HEX6QC3 | 3 | <HEX_Thr>TCGTGA<BHQ_2>CATTATTCAATTTC TTCCCTACCAGTGCCA<Spc_C3> |
| HPIV 2 | F. Primer | HPIV2_FP5_A | 4 | GTTAAGATATCCCTAGAGCAACTTC<t_BB_dA> |
| | R. Primer | HPIV2_RP5_A | 5 | TGAGTATAACTAGAAAATGCATAGGAACT<t_BB_dA> |
| | Probe | HPIV2_PRB3_HEX6QC3 | 6 | <HEX_Thr>TGGCTC<BHQ_2>CATCATCTAAACG GTGTGTAATATTTGCAGATGT<Spc_C3> |
| | Probe | HPIV2_PRB2_COU6Q.C3 | 7 | <Coum_Thr>TTAAGT<BHQ_2>GTTGTGGCTCCAT CATCTAAACGGTGTGTAAT<Spc_C3> |
| HPIV 3 | F. Primer | HPIV3_FP2_A | 8 | AGCAGAAATGATCTCACAACC<t_BB_dA> |
| | F. Primer | HPIV3_FP4_A | 15 | GCAGAAATGATCTCACAACCATAGAAAAG<t_BB_dA> |
| | R. Primer | HPIV3_RP2_A | 9 | GGATAGAGTCAAAGCTGCCATT<t_BB_dC> |
| | R. Primer | HPIV3_RP3_A | 16 | AGCTGCCATTCTAGTCTCAATTCCAT<t_BB_dA> |
| | Probe | HPIV3_PRB2_JA11Q | 10 | <JA270_Thr>TTGTTGGTAAC<BHQ_2>TACATAAG AGATGCAGGTCTCGCT<Phos> |
| | Probe | HPIV3_PRB3_T HRBP3_J77 | 17 | <JA270_Thr>CTGATTGTA<BHQ_2>TTGAAGAATG AAGCGAGACCTGCATCTCTT<Spc_C3> |
| HPIV 4 | F. Primer | HPIV4_FP3_A | 11 | GGTGGTATTCAAATAGATCTTGAG<t_BB_dC> |
| | F. Primer | HPIV4_FP8_A | 18 | AACAGATGAACGAAGAATTGCATC<t_BB_dA> |
| | R. Primer | HPIV4_RP1_A | 12 | TCATTATCACCAAAAGCCCAAATATATA<t_BB_dC> |
| | R. Primer | HPIV4_RP4_A | 19 | TGTTCATTATCACCAAAAGCCCAAATAT<t_BB_dA> |
| | Probe | HPIV4_PRB3_FAM6Q | 13 | <FAM_Thr>AGATTT<BHQ_2>TGAGAAGCACCTG GTATTTGGGCC<Phos> |
| | Probe | HPIV4_PRB3_HEX6QC3 | 14 | <HEX_Thr>AGATTT<BHQ_2>TGAGAAGCACCTG GTATTTGGGCC<Spc_C3> |

The variant may, e.g., vary from the sequence of SEQ ID NOs:1-19 by one or more nucleotide additions, deletions or substitutions such as one or more nucleotide additions, deletions or substitutions at the 5' end and/or the 3' end of the respective sequence of SEQ ID NOs:1-19. As detailed above, a primer and/or probe may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the HPIV (including HPIV 1-4) target, e.g., nucleic acids encoding alternative portions of HPIV (including HPIV 1-4) can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of HPIV (including HPIV 1-4). The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a HPIV (including HPIV 1-4) (target) nucleic acid. A "probe" can be referred to as a "detection probe" meaning that it detects the target nucleic acid.

In some embodiments, the described HPIV (including HPIV 1-4) probes can be labeled with at least one fluorescent label. In one embodiment, the HPIV (including HPIV 1-4) probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs:3, 6, 7, 10, 13, 14 and/or 17.

Designing oligonucleotides to be used as probes can be performed in a manner similar to the design of primers. Embodiments may use a single probe or a pair of probes for detection of the amplification product. Depending on the embodiment, the probe(s) used may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length. Constructs can include vectors each containing one of HPIV (including HPIV 1-4) primers and probes nucleic acid molecules (e.g., SEQ ID NOs:1, 2, 3, 4, 5, 6, 7, 8, 9, 10, 11, 12, 13, 14, 15, 16, 17, 18 and 19). Constructs can be used, for example, as control template nucleic acid molecules. Vectors suitable for use are commercially available and/or produced by recombinant nucleic acid technology methods routine in the art. HPIV (including HPIV 1-4) nucleic acid molecules can be obtained, for example, by chemical synthesis, direct cloning from HPIV (including HPIV 1-4), or by nucleic acid amplification.

Constructs suitable for use in the methods typically include, in addition to the HPIV (including HPIV 1-4) nucleic acid molecules (e.g., a nucleic acid molecule that contains one or more sequences of SEQ ID NOs:1-19), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery. Constructs containing HPIV (including HPIV 1-4) nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described HPIV (including HPIV 1-4) nucleic acid sequences (e.g., SEQ ID NOs:1, 2, 4, 5, 8, 9, 11, 12, 15, 16, 18 and/or 19). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, or the mRNA produced by a DNA virus, such as HPIV (including HPIV 1-4), is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ HPIV (including HPIV 1-4) nucleic acid such as RNA or DNA (cDNA). The template nucleic acid need not be purified; it may be a minor fraction of a complex mixture, such as HPIV (including HPIV 1-4) nucleic acid contained in human cells. HPIV (including HPIV 1-4) nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs:1, 2, 4, and 5) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target HPIV (including HPIV 1-4) nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996, 143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety or dye (e.g., HEX or FAM) and a corresponding quencher (e.g., BlackHole Quencher™ (BHQ) (such as BHQ-2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quencher™ (BHQ) (such as BHQ2), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the HPIV (including HPIV 1-4) target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced there between.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, VA)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of HPIV (Including HPIV 1-4) Amplified Product (Amplicon)

The present disclosure provides methods for detecting the presence or absence of HPIV (including HPIV 1-4) in a biological or non-biological sample. Methods provided avoid problems of sample contamination, false negatives, and false positives. The methods include performing at least one cycling step that includes amplifying a portion of HPIV (including HPIV 1-4) target nucleic acid molecules from a sample using one or more pairs of HPIV (including HPIV 1-4) primers, and a FRET detecting step. Multiple cycling steps are performed, preferably in a thermocycler. Methods can be performed using the HPIV (including HPIV 1-4) primers and probes to detect the presence of HPIV (including HPIV 1-4), and the detection of HPIV (including HPIV 1-4) indicates the presence of HPIV (including HPIV 1-4) in the sample.

As described herein, amplification products can be detected using labeled hybridization probes that take advantage of FRET technology. One FRET format utilizes TaqMan® technology to detect the presence or absence of an amplification product, and hence, the presence or absence of HPIV (including HPIV 1-4). TaqMan® technology utilizes one single-stranded hybridization probe labeled with, e.g., one fluorescent moiety or dye (e.g., HEX or FAM) and one quencher (e.g., BHQ-2), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of HPIV (including HPIV 1-4) in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of HPIV (including HPIV 1-4) genomes). If amplification of HPIV (including HPIV 1-4) target nucleic acid occurs and an amplification product is produced, the step of hybridizing results in a detectable signal based upon FRET between the members of the pair of probes.

Generally, the presence of FRET indicates the presence of HPIV (including HPIV 1-4) in the sample, and the absence of FRET indicates the absence of HPIV (including HPIV 1-4) in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to whole blood, respiratory specimens, urine, fecal specimens, blood specimens, plasma, dermal swabs, nasal swabs, nasopharyngeal samples, wound swabs, blood cultures, skin, and soft tissue infections. Collection and storage methods of biological samples are known to those of skill in the art. Biological samples can be processed (e.g., by nucleic acid extraction methods and/or kits known in the art) to release HPIV (including HPIV 1-4) nucleic acid or in some cases, the biological sample can be contacted directly with the PCR reaction components and the appropriate oligonucleotides. In some instances, the biological sample is whole blood. When whole blood is typically collected, it is often collected in vessels containing anticoagulants, such as heparin, citrate, or EDTA, which enables the whole blood to be stored at suitable temperatures. However, under such conditions, the nucleic acids within the whole blood undergo considerable amount of degradation. Therefore, it may be advantageous to collect the blood in a reagent that will lyse, denature, and stabilize whole blood components, including nucleic acids, such as a nucleic acid-stabilizing solution. In such cases, the nucleic acids can be better preserved and stabilized for subsequent isolation and analysis, such as by nucleic acid test, such as PCR. Such nucleic acid-stabilizing solution are well known in the art, including, but not limited to, cobas PCR media, which contains 4.2 M guanadinium salt (GuHCl) and 50 mM Tris, at a pH of 7.5.

The sample can be collected by any method or device designed to adequately hold and store the sample prior to analysis. Such methods and devices are well known in the art. In the case that the sample is a biological sample, such as whole blood, the method or device may include a blood collection vessel. Such a blood collection vessel is well known in the art, and may include, for example, a blood collection tube. In many cases, it may be advantageous to use a blood collection tube wherein the blood collection vessel is under pressure in the space intended for sample uptake, such as a blood vessel with an evacuated chamber, such as a vacutainer blood collection tube. Such blood collection tubes with an evacuated chamber, such as a vacutainer blood collection tube are well known in the art. It may further be advantageous to collect the blood in a blood collection vessel, with or without an evacuated chamber, that contains within it, a solution that will lyse, denature, and stabilize whole blood components, including nucleic acids, such as a nucleic acid-stabilizing solution, such that the whole blood being drawn immediately contacts the nucleic acid-stabilizing solution in the blood collection vessel.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the HPIV (including HPIV 1-4) probes from the HPIV (including HPIV 1-4) amplification products can confirm the presence or absence of HPIV (including HPIV 1-4) in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control(s) can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

The LightCycler® 480 II Real-Time PCR System can also be operated using a PC workstation. The instrument has a thermal block cycler and heating and cooling is achieved using Peltier elements. Fluorescent signals from the samples are obtained from the 96-well plate using a high-intensity Xenon lamp which emits light across a broad spectrum. Flexible combination of the built-in filters for specific excitation and emission allows the use of a variety of fluorescent dyes and detection formats. The software can display the fluorescence signals and calculate CT values, and the data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect HPIV (including HPIV 1-4). An article of manufacture can include primers and probes used to detect the HPIV (including HPIV 1-4) gene target, together with suitable packaging materials. Representative primers and probes for detection of HPIV (including HPIV 1-4) are capable of hybridizing to HPIV (including HPIV 1-4) target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to HPIV (including HPIV 1-4) target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the HPIV (including HPIV 1-4) probes. Examples of suitable FRET donor fluorescent moieties and corresponding acceptor fluorescent moieties are provided above.

Articles of manufacture can also contain a package insert or package label having instructions thereon for using the HPIV (including HPIV 1-4) primers and probes to detect HPIV (including HPIV 1-4) in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure also provide for a set of primers and one or more detectable probes for the detection of HPIV (including HPIV 1-4) in a sample.

Embodiments of the present disclosure will be further described in the following examples, which do not limit the scope of the invention described in the claims.

EXAMPLES

The following examples and figures are provided to aid the understanding of the subject matter, the scope of which is set forth in the appended claims. It is understood that modifications can be made in the procedures set forth without departing from the spirit of the invention.

The test was a fully automated sample preparation (nucleic acid extraction and purification) followed by PCR amplification and detection. The system used was the Cobas® 6800/8800 System, which consisted of a sample supply module, the transfer module, the processing module, and the analytic module. Automated data management was performed by the Cobas® 6800/8800 System. The master mix contained detection probes, which were specific for Human Parainfluenza Virus 1-4 (HPIV 1-4) and control nucleic acids. The specific Human Parainfluenza Virus 1-4 (HPIV 1-4) and control detection probes were each labeled with unique fluorescent dyes, which act as a reporter. Each probe also had a second dye, which acted as a quencher. The reporter dye is measured at a defined wavelength, thus permitting detection and discrimination of the amplified Human Parainfluenza Virus 1-4 (HPIV 1-4) target and the control. The fluorescent signal of the intact probes was suppressed by the quencher dye. During the PCR amplification step, hybridization of the probes to the specific single-stranded DNA template resulted in cleavage by the 5' to 3' nuclease activity of the DNA polymerase resulting in separation of the reporter and quencher dyes, and the generation of fluorescent signal. With each PCR cycle, increasing amounts of cleaved probes were generated and the cumulative signal of the reporter dye was concomitantly increased. Because the two specific reporter dyes are measured at defined wavelengths, simultaneous detection and discrimination of the amplified Human Parainfluenza Virus 1-4 (HPIV 1-4) target and the control was possible.

The primers and probes for the Human Parainfluenza Virus 1-4 (HPIV 1-4) test were designed by seeding primers and probes along the genome in the most conserved regions based on the alignment. One set of oligonucleotides (SEQ ID NOs:1-3) was designed to detect and amplify HPIV 1 target nucleic acids. Another set of oligonucleotides (SEQ ID NOs:4-7) was designed to detect and amplify HPIV 2 target nucleic acids. Another set of oligonucleotides (SEQ ID NOs:8-10) was designed to detect and amplify HPIV 3 target nucleic acids. Another set of oligonucleotides (SEQ ID NOs:11-14) was designed to detect and amplify HPIV 4 target nucleic acids. Another set of oligonucleotides (SEQ ID NO:15-17) was designed to detect and amplify HPIV 3 target nucleic acids. Another set of oligonucleotides (SEQ ID NOs:18-19 and 13-14) was designed to detect and amplify HPIV 4 target nucleic acids. Another set of oligonucleotides (SEQ ID NOs:11, 18-19 and 13-14) was designed to detect and amplify HPIV 4 target nucleic acids. Each set of oligonucleotides (or primers/probes) can be used in singleplex in its own reaction to amplify and detect the particular target region of interest (i.e., HPIV 1, HPIV 2, HPIV 3, or HPIV 4). However, the set of oligonucleotides can also be combined in a multiplex target assay, whereby in a single real-time PCR reaction, any or all of HPIV 1-4 target nucleic acids are amplified and detected in the sample (if the targets are present in the sample), because the reaction mixture contains one or more sets of oligonucleotides (SEQ ID NOs:1-3 for HPIV 1; SEQ ID NOs:3-7 for HPIV 2; SEQ ID NOs:8-10 or SEQ ID NO:15-17 for HPIV 3; and SEQ ID NOs:11-14 or SEQ ID NOs:18-19 and 13-14 or SEQ ID NOs:11, 18-19 and 13-14 for HPIV 4). For detection of the HPIV 1 target nucleic acids, the forward primer corresponds to the nucleic acid sequence of SEQ ID NO:1, the reverse primer corresponds to the nucleic acid sequence of SEQ ID NO:2, and the probe corresponds to the nucleic acid sequence of SEQ ID NO:3. For detection of the HPIV 2 target nucleic acids, the forward primer corresponds to the nucleic acid sequence of SEQ ID NO:4, the reverse primer corresponds to the nucleic acid sequence of SEQ ID NO:5, and the probes correspond to the nucleic acid sequence of SEQ ID NOs:6 and/or 7. For detection of the HPIV 3 target nucleic acids, the forward primer corresponds to the nucleic acid sequence of SEQ ID NO:8, the reverse primer corresponds to the nucleic acid sequence of SEQ ID NO:9, and the probe corresponds to the nucleic acid sequence of SEQ ID NO:10. Alternatively, for detection of the HPIV 3 target nucleic acids, the forward primer corresponds to the nucleic acid sequence of SEQ ID NO:15, the reverse primer corresponds to the nucleic acid sequence of SEQ ID NO:16, and the probe corresponds to the nucleic acid sequence of SEQ ID NO:17. For detection of the HPIV 4 target nucleic acids, the forward primer corresponds to the nucleic acid sequence of SEQ ID NO:11, the reverse primer corresponds to the nucleic acid sequence of SEQ ID NO:12, and the probes correspond to the nucleic acid sequence of SEQ ID NOs:13 and/or 14. Alternatively, for detection of the HPIV 4 target nucleic acids, the forward primer corresponds to the nucleic acid sequence of SEQ ID NO:18, the reverse primer corresponds to the nucleic acid sequence of SEQ ID NO:19, and the probes correspond to the nucleic acid sequence of SEQ ID NOs:13 and/or 14. In some instances the set for detection of the HPIV 4 target nucleic acids further comprises a second forward primer that corresponds to the nucleic acid sequence of SEQ ID NO:11. These oligonucleotides can be employed in individual assays for detection and amplification of HPIV 1 target nucleic acids (using oligonucleotides corresponding to SEQ ID NOs:1-3), HPIV 2 target nucleic acids (using oligonucleotides corresponding to SEQ ID NOs:4-7), HPIV 3 target nucleic acids (using oligonucleotides corresponding to SEQ ID NOs:8-10 or SEQ ID NO:15-17), and HPIV 4 target nucleic acids (using oligonucleotides corresponding to SEQ ID NOs:11-14 or SEQ ID NOs:18-19 and 13-14 or SEQ ID NOs:11, 18-19 and 13-14). Alternatively, the oligonucleotides can be used in a multiplex target assay wherein the oligonucleotides simultaneously is designed to detect and amplify a plurality of nucleic acid targets from the different types of HPIV (for example, HPIV 1-4). For example, oligonucleotides for detection and amplification of HPIV 1, HPIV 2, HPIV 3, and/or HPIV 4 can be added to the sample at the same time. There are certain advantages to a multiplex target assay, in that in any or all of the four types of HPIV (HPIV 1-4) can be detected in a single sample, without having to employ additional resources. In this way, resources (e.g., PCR reagents, sample), costs, and time are conserved, in a multiplex assay. Multiplex assays allow for an efficient, rapid, reliable, and inexpensive means to detect a plurality of HPIV types simultaneously in a single sample.

Figure 4:
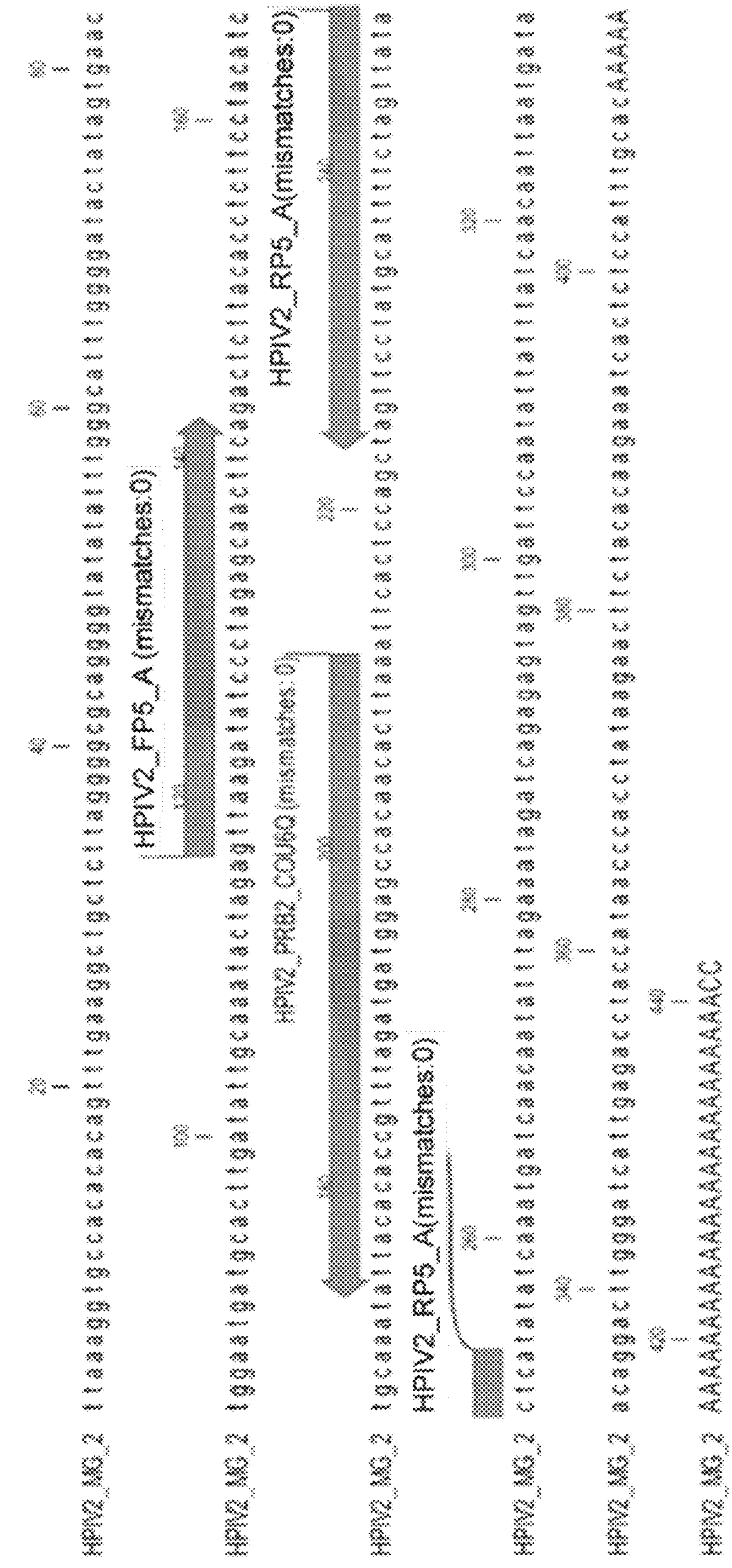
FIG. 4 shows the alignment of a set of primers (SEQ ID NOs: 4 and 5) and a probes (SEQ ID NOs: 6 and 7) for amplification and detection of the HPIV 2 target (SEQ ID NO:16).
Figure 5:
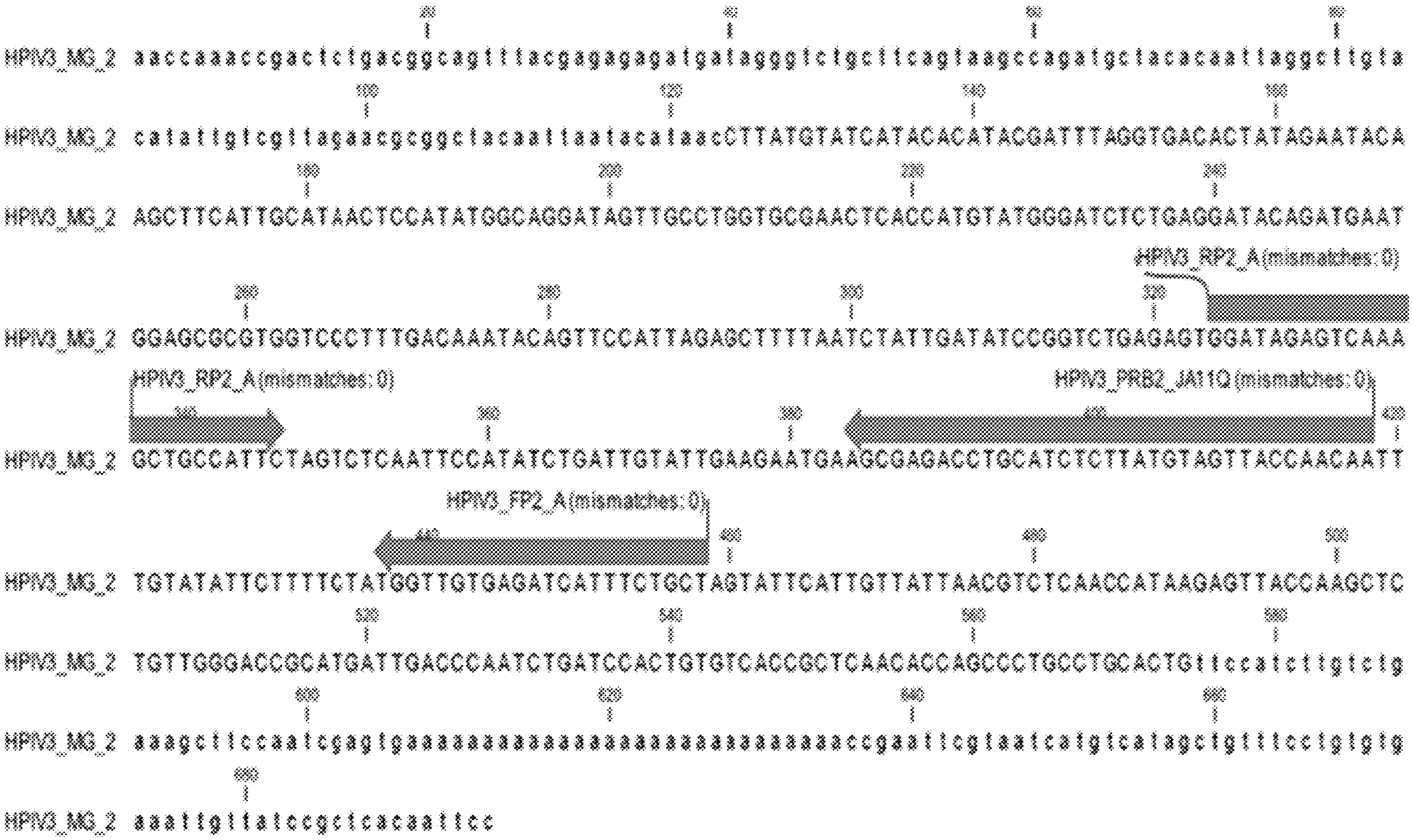
FIG. 5 shows the alignment of a set of primers (SEQ ID NOs: 8 and 9) and a probe (SEQ ID NO: 10) for amplification and detection of the HPIV 3 target (SEQ ID NO:17)
Figure 6:
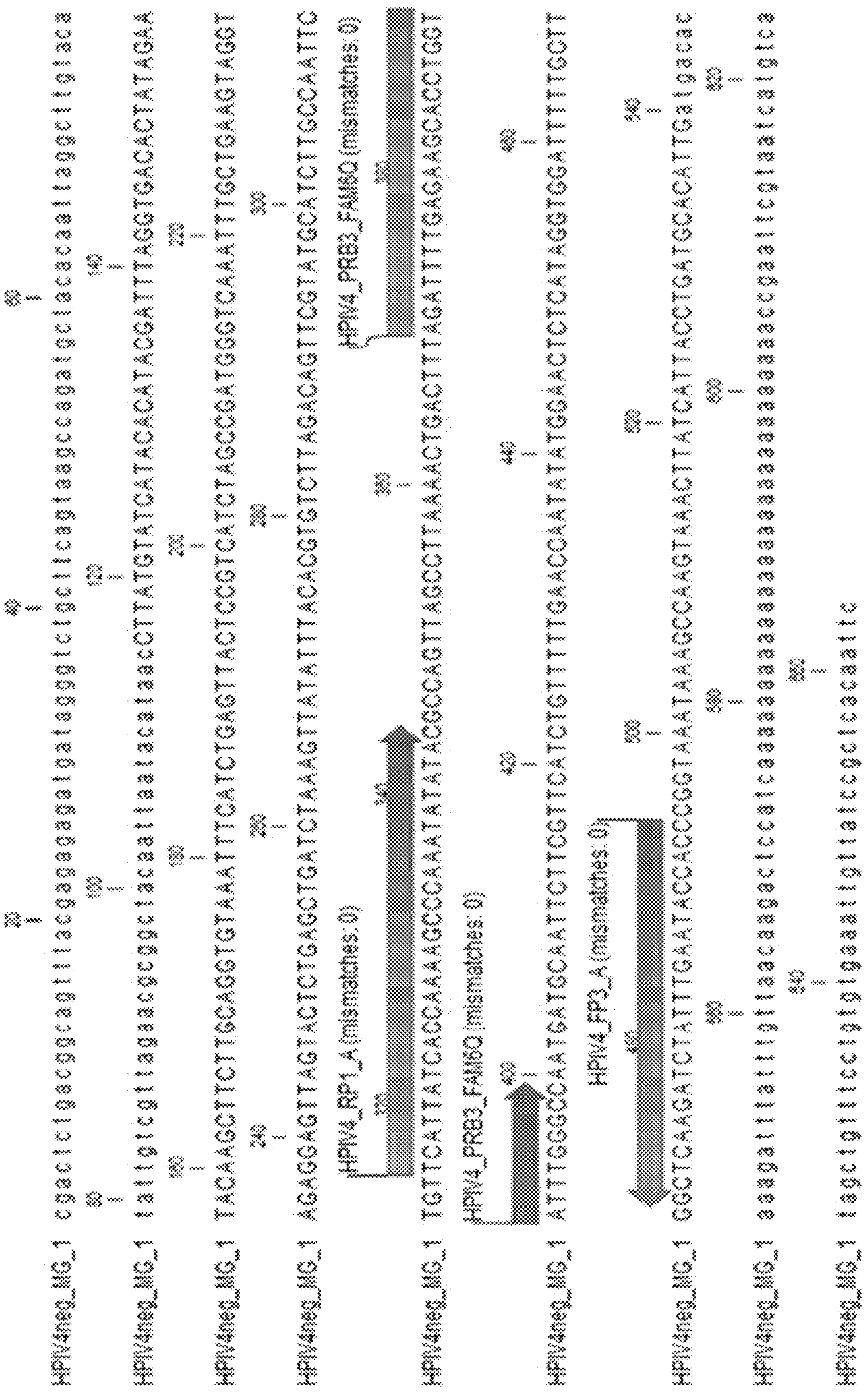
FIG. 6 shows the alignment of a set of primers (SEQ ID NOs: 11 and 12) and a probes (SEQ ID NOs: 13 and 14) for amplification and detection of the HPIV 4 target (SEQ ID NO:18).

Example 1: Design of Primers and Probes for Detection of HPIV 1-4 by Real-Time PCR The HPIV 1-4 nucleic acid test was designed to detect all of the four types of HPIV (HPIV 1-4). Viral pathogen-specific assays were designed by proprietary software using optimal oligonucleotide sequences found within the genome, based on specific inclusivity and exclusivity requirements. A specific target region was selected for each of the HPIV 1-4 assays (i.e., a total of four target regions). The HPIV 1 assay targets the L polymerase protein gene (see, FIG. 3), the HPIV 2 assay targets the Large Protein (see, FIG. 4), the HPIV 3 assay is designed in the nucleocapsid protein (see, FIG. 5), and the HPIV 4 assay targets the Large Protein (see, FIG. 6). Each assay has one forward primer, one reverse primer, and one probe for each HPIV type (HPIV 1-4).

Example 2: HPIV 1 Primers and Probes Amplify and Detect the L Polymerase Protein Gene of HPIV 1 in a Real-Time PCR Assay HPIV 1 oligonucleotides were tested using primers/probes for detecting HPIV 1 (SEQ ID NOs:1-3). The final concentrations for the forward primer (SEQ ID NO:1) was 200 nM, the reverse primer (SEQ ID NO:2) was 150 nM, and the probe (SEQ ID NO:3) at 75 nM. The HPIV 1 assay was tested in the HEX channel. In vitro generated transcripts were used at the following concentrations: 10, $10^2$, $10^3$, $10^4$, and $10^5$ copies per reaction. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is depicted in Table 2, below:

TABLE 2 cobas ® 6800/8800 PCR Profile

| Step | Cycles | Target (° C.) | Hold time (hh:mm:ss) | Ramp |
|---|---|---|---|---|
| Pre-PCR | 1 | 50 | 00:02:00 | 4.4 |
| | | 94 | 00:00:05 | 4.4 |
| | | 55 | 00:02:00 | 2.2 |
| | | 60 | 00:06:00 | 4.4 |
| | | 65 | 00:04:00 | 4.4 |
| 1. Meas | 5 | 95 | 00:00:05 | 4.4 |
| | | 55 | 00:00:30 | 2.2 |
| 2. Meas | 45 | 91 | 00:00:05 | 4.4 |
| | | 58 | 00:00:25 | 2.2 |
| Post | 1 | 40 | 00:02:00 | 2.2 |

Figure 7A:
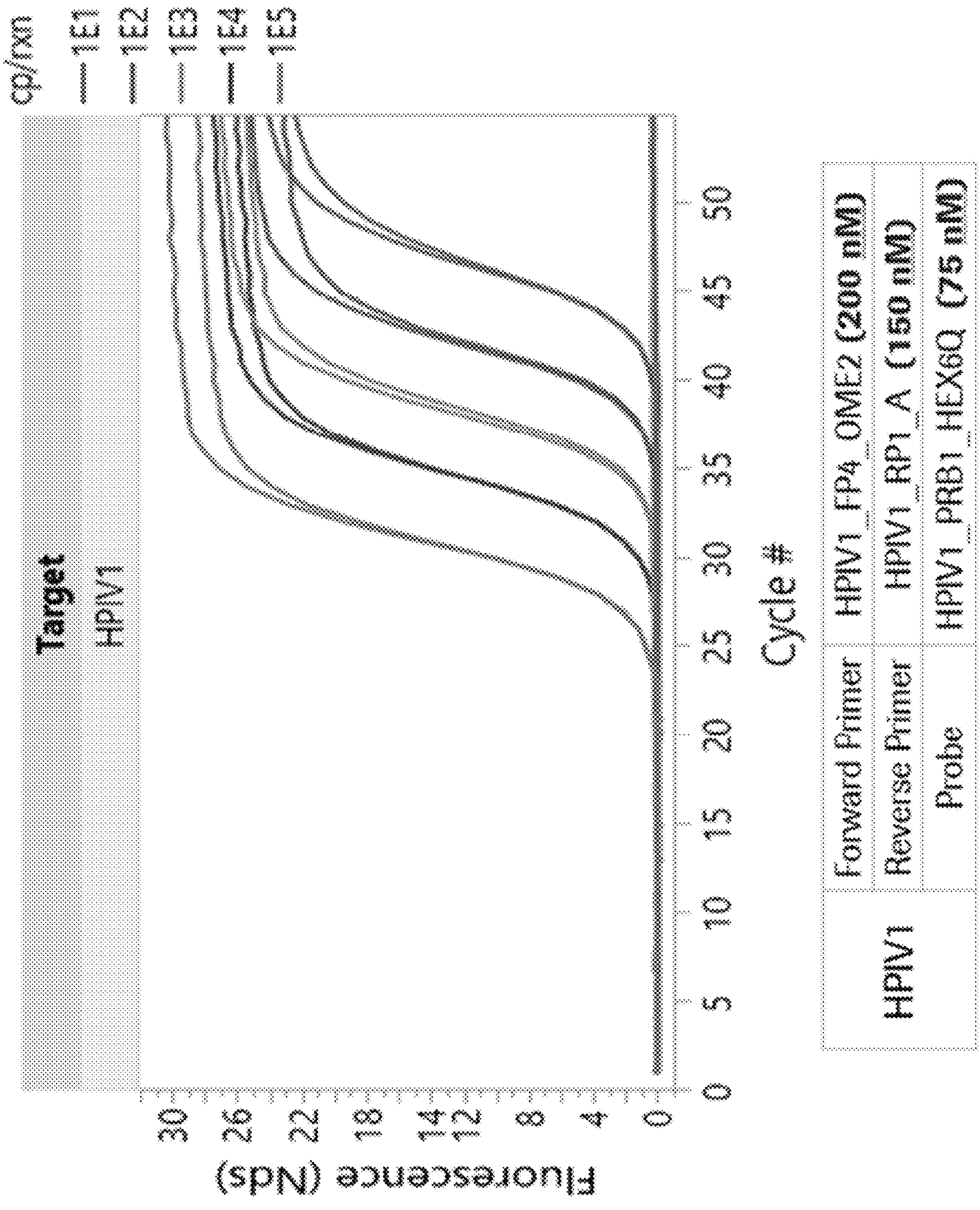
FIG. 7A shows PCR growth curves of a dilution series of the IVT transcript for HPIV 1, as described in Example 2 (using the oligonucleotides for HPIV 1, which include SEQ ID NOs:1-3).
Figure 7B:
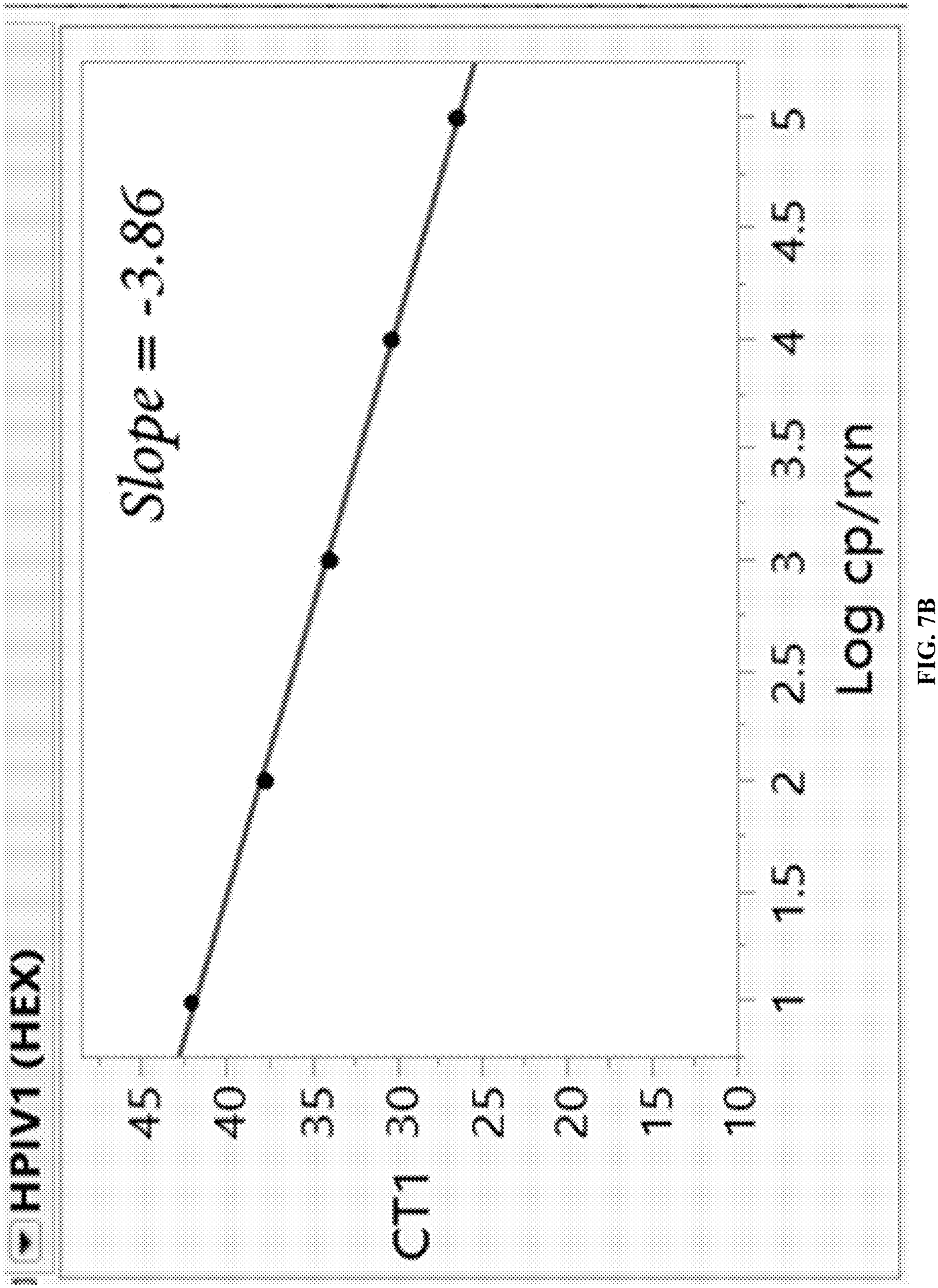
FIG. 7B shows the efficiency of the HPIV 1 assay, as described in Example 2 (using the oligonucleotides for HPIV 1, which include SEQ ID NOs:1-3).

The results are shown in FIG. 7A, which shows PCR growth curves of a dilution series of the performance of a HPIV 1 assay. FIG. 7A shows that the HPIV 1 primers and probes (SEQ ID NOs:1-3) employed, are able to amplify and detect HPIV 1. FIG. 7B shows the efficiency of the HPIV 1 assay, and demonstrates that the HPIV 1 real-time PCR assay is efficient, showing excellent sensitivity at low target concentrations. These data show that the HPIV 1 real-time PCR assay is linear across the range tested, and can detect up to 10 copies of target per reaction. Taken together, these data demonstrate that the HPIV 1 real-time assay (which include oligonucleotide sequences of SEQ ID NOs:1-3) is able to detect and amplify HPIV 1.

Figure 8A:
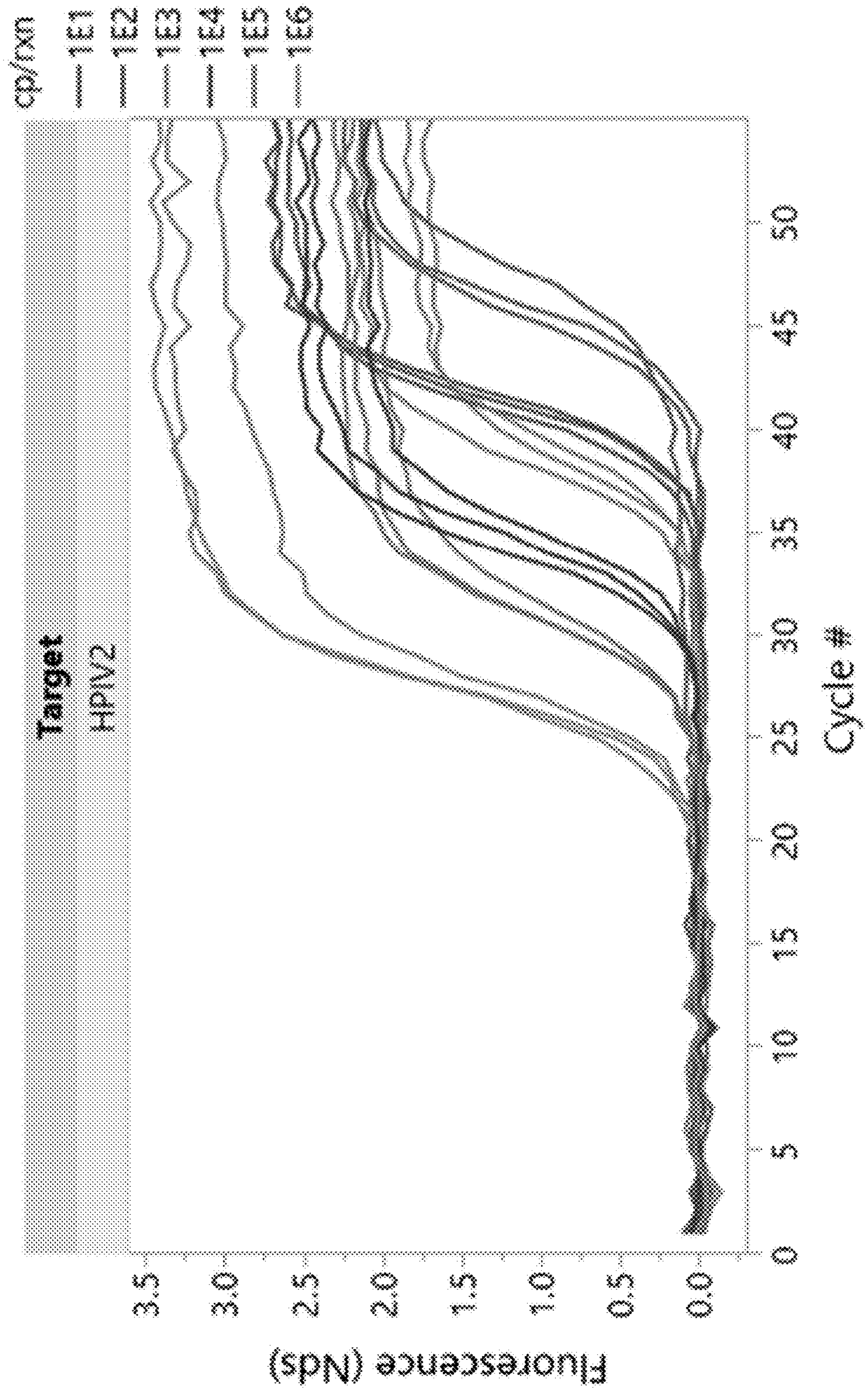
FIG. 8A shows PCR growth curves of a dilution series of the performance of a HPIV 2 assay, as described in Example 3 (using the oligonucleotides for HPIV 2, which include SEQ ID NOs:4, 5, and 7).
Figures 8B, 8C:
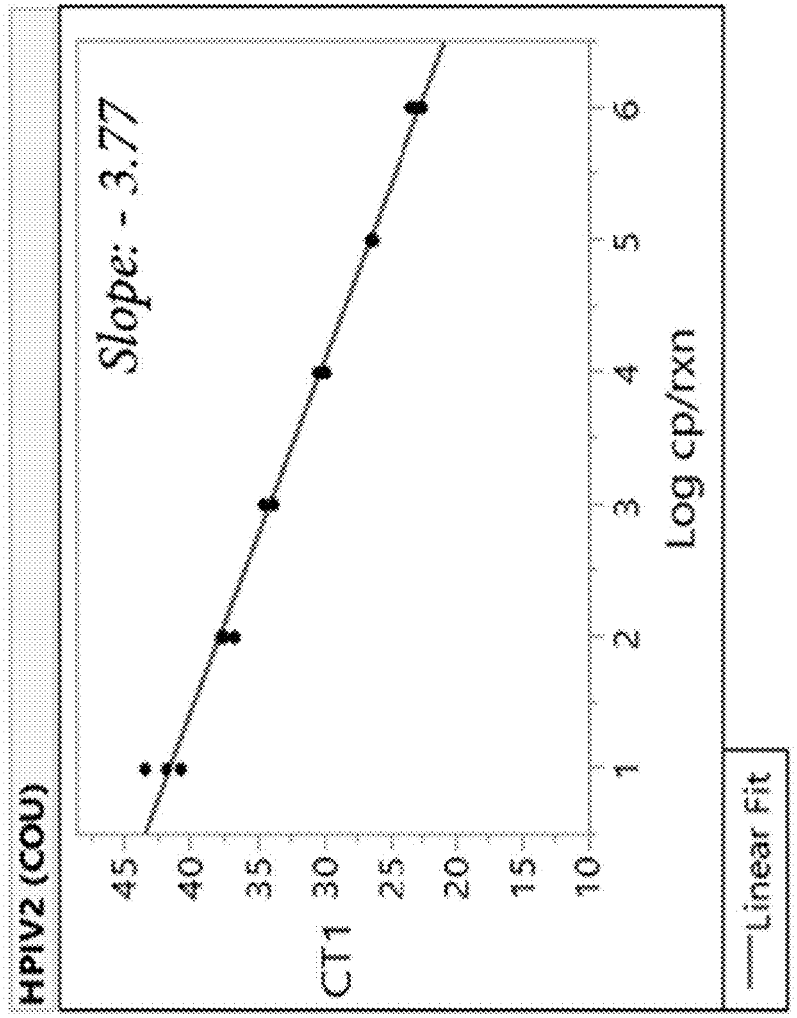
FIG. 8B shows the efficiency of the HPIV 2 assay, as described in Example 3 (using the oligonucleotides for HPIV 2, which include SEQ ID NOs:4, 5, and 7).
FIG. 8C shows the primer and probe concentrations under three different testing conditions, as described in Example 3 (using the oligonucleotides for HPIV 2, which include SEQ ID NOs:4, 5, and 7).
Figure 8D:
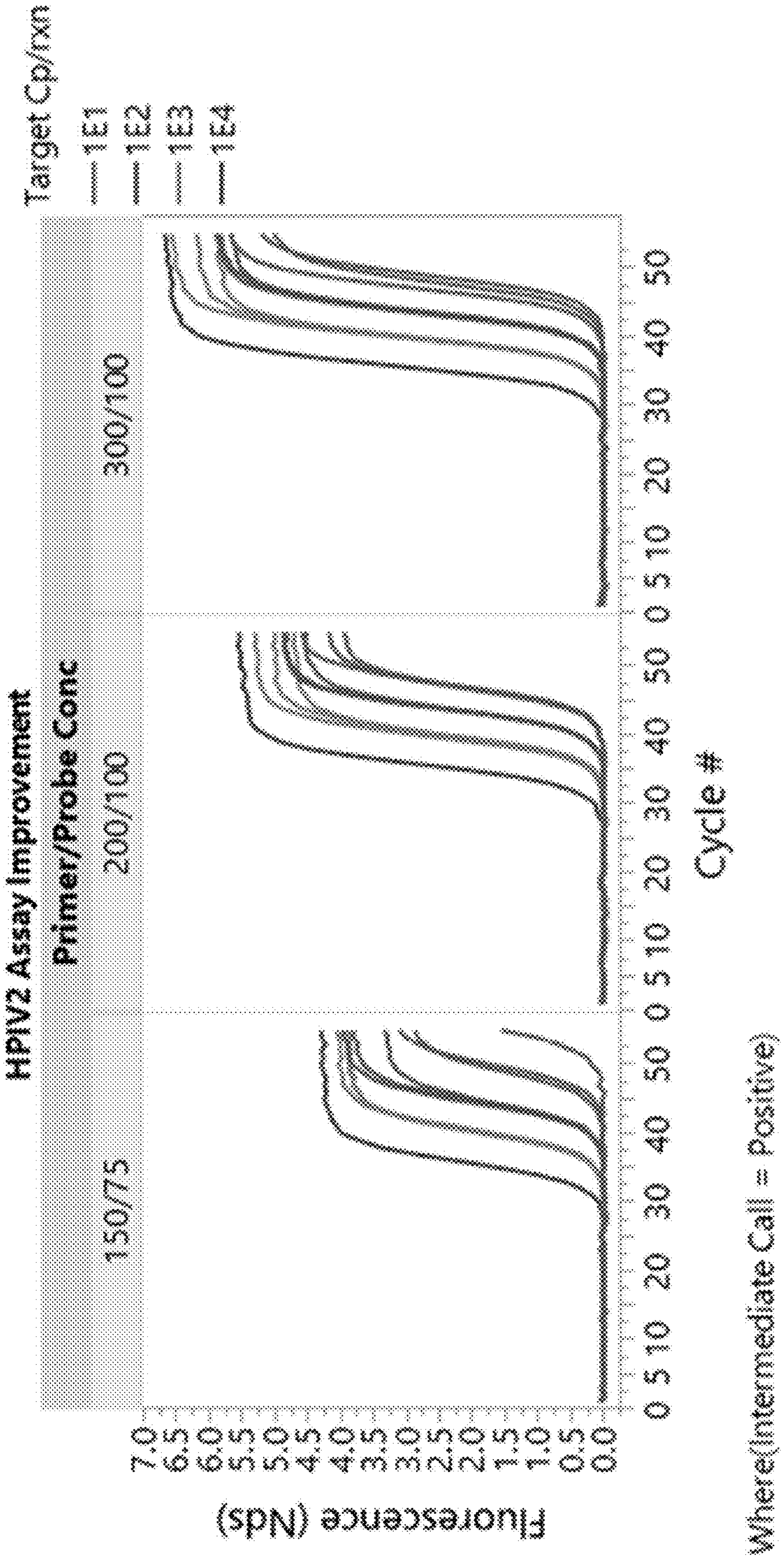
FIG. 8D shows the growth curves of the performance of the HPIV 2 assay under the three different conditions for various primer and probe concentrations, which show that increasing the primer and probe concentrations improves the signal.

Example 3: HPIV 2 Primers and Probes Amplify and Detect the Large Protein Gene of HPIV 2 in a Real-Time PCR Assay HPIV 2 oligonucleotides were tested using primers/probes for detecting HPIV 2 (SEQ ID NOs:4, 5, and 7). The final concentrations for the forward primer (SEQ ID NO:4) was 150 nM, the reverse primer (SEQ ID NO:5) was 150 nM, and the probe (SEQ ID NO:7) at 75 nM. The HPIV 2 assay was tested in the COU channel. In vitro generated transcripts were used at the following concentrations: 10, $10^2$, $10^3$, $10^4$, $10^5$, and $10^6$ copies per reaction. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The results are shown in FIG. 8A, which shows PCR growth curves of a dilution series of the performance of a HPIV 2 assay. FIG. 8A shows that the HPIV 2 primers and probes (SEQ ID NOs:4, 5, and 7) employed, are able to amplify and detect HPIV 2. FIG. 8B shows the efficiency of the HPIV 2 assay, and demonstrates that the HPIV 2 real-time PCR assay is efficient, showing excellent sensitivity at low target concentrations. These data show that the HPIV 2 real-time PCR assay is linear across the range tested. However, overall, these results indicate that improvements could be made with respect to the performance of the HPIV 2 assay, as the RFI could be higher, suggesting that optimization of the assay would be needed (e.g., primer/probe oligonucleotide concentrations). To that end, the concentrations of the primers and probes were titrated. Three different concentration conditions were tested: (1) primer concentration at 150 nM and probe concentration of 75 nM; (2) primer concentration of 200 nM and probe concentration of 100 nM; and (3) primer concentration of 300 nM and probe concentration of 100 nM (as shown in FIG. 8C). In vitro generated transcripts were used at the following concentrations: 10, $10^2$, $10^3$, and $\mathbf{10^4}$ copies per reaction. The results of each of the three different concentration conditions are shown in FIG. 8D, which shows increasing the primer and probe concentrations improves the signal. These studies show that the HPIV 2 assay is robust enough to detect down to 10 copies per reaction. Taken together, these data demonstrate that the HPIV 2 real-time assay (which include oligonucleotide sequences of SEQ ID NOs:4, 5, and 7) is able to detect and amplify HPIV 2.

Figure 9A:
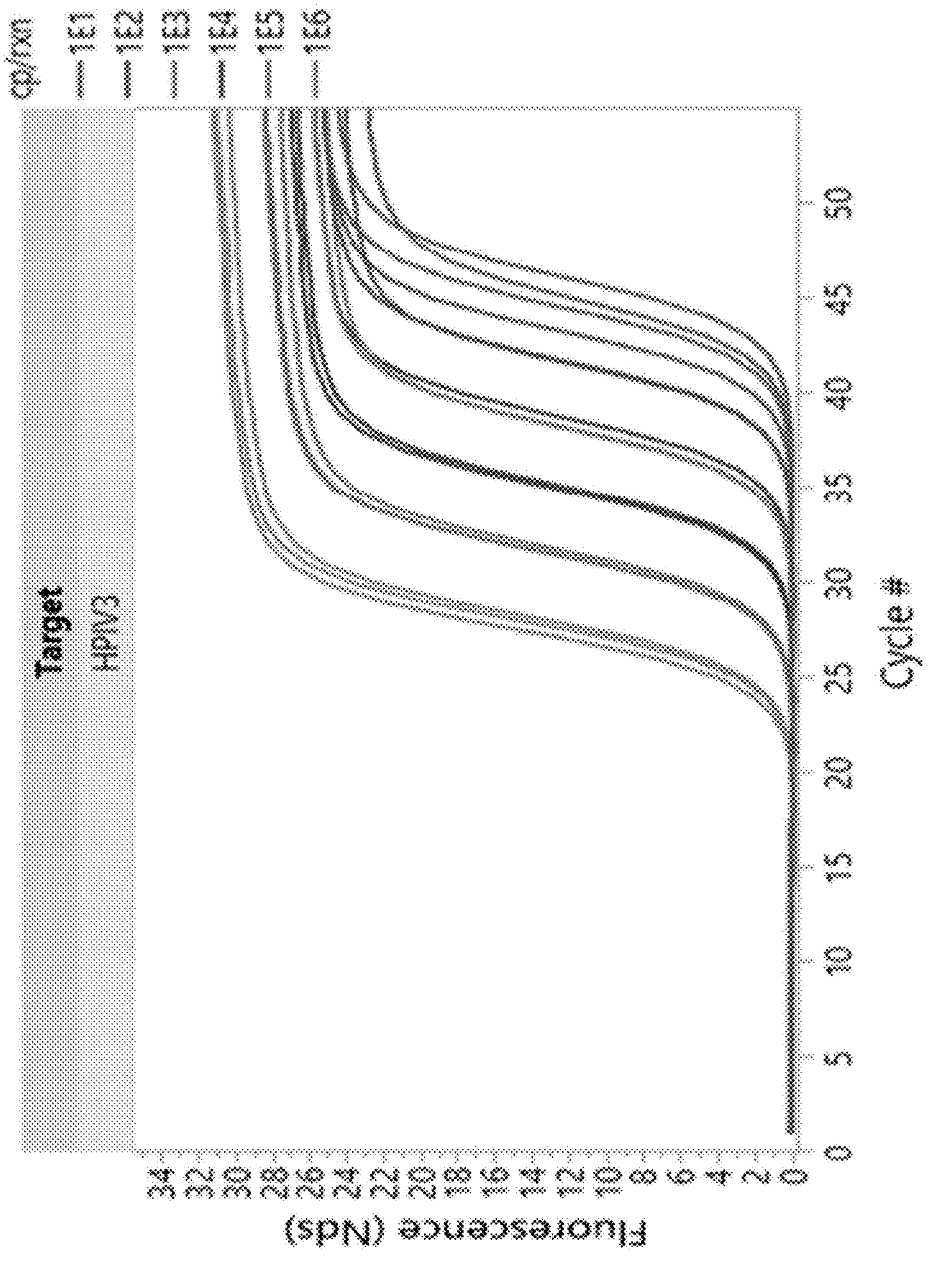
FIG. 9A shows PCR growth curves of a dilution series of the performance of a HPIV 3 assay, as described in Example 4 (using the oligonucleotides for HPIV 3, which include SEQ ID NOs:8-10).
Figure 9B:
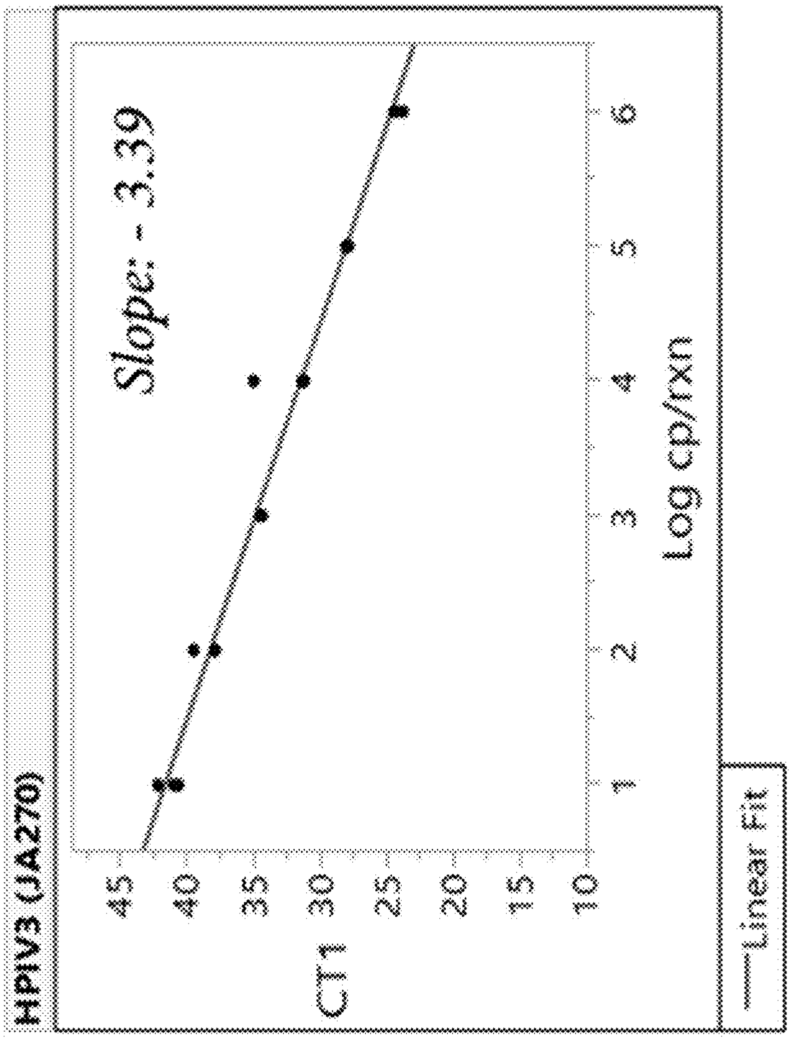
FIG. 9B shows the efficiency of the HPIV 3 assay, as described in Example 4 (using the oligonucleotides for HPIV 3, which include SEQ ID NOs:8-10).

Example 4: HPIV 3 Primers and Probes Amplify and Detect the Nucleocapsid Protein Gene of HPIV 3 in a Real-Time PCR Assay HPIV 3 oligonucleotides were tested using primers/probes for detecting HPIV 3 (SEQ ID NOs:8-10). The final concentrations for the forward primer (SEQ ID NO:8) was 200 nM, the reverse primer (SEQ ID NO:9) was 150 nM, and the probe (SEQ ID NO:10) at 100 nM. The HPIV 3 assay was tested in the JA270 channel. In vitro generated transcripts were used at the following concentrations: 10, $10^2$, $10^3$, $10^4$, $10^5$, and $10^6$ copies per reaction. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The results are shown in FIG. 9A, which shows PCR growth curves of a dilution series of the performance of a HPIV 3 assay. FIG. 9A shows that the HPIV 3 primers and probes (SEQ ID NOs:9-10) employed, are able to amplify and detect HPIV 3. FIG. 9B shows the efficiency of the HPIV 3 assay, and demonstrates that the HPIV 3 real-time PCR assay is efficient, showing excellent sensitivity at low target concentrations. These data show that the HPIV 3 real-time PCR assay is linear across the range tested, and can detect up to 10 copies per reaction. Taken together, these data demonstrate that the HPIV 3 real-time assay (which include oligonucleotide sequences of SEQ ID NOs:8-10) is able to detect and amplify HPIV 3.

Figure 10A:
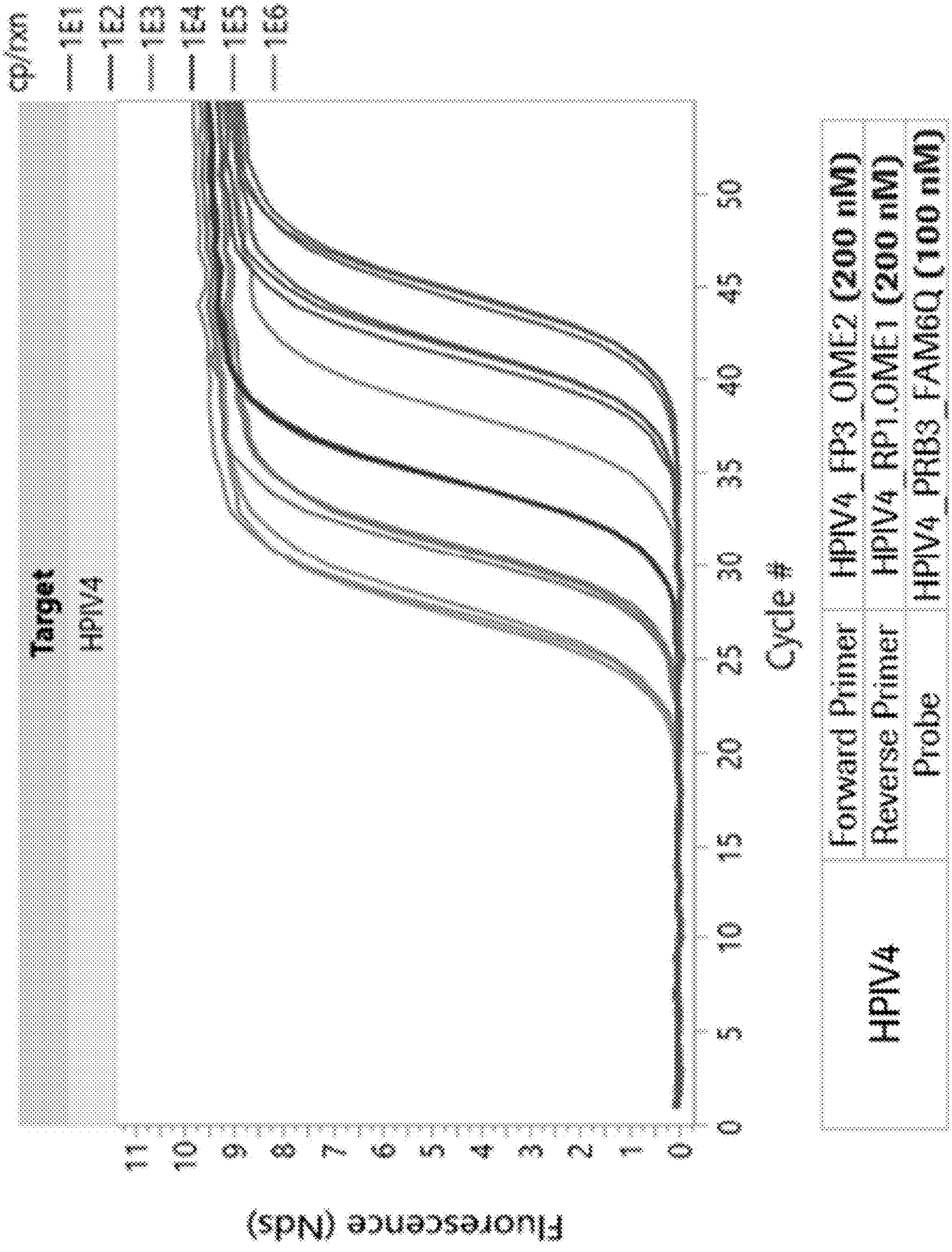
FIG. 10A shows PCR growth curves of a dilution series of the performance of a HPIV 4 assay, as described in Example 5 (using the oligonucleotides for HPIV 4, which include SEQ ID NOs:11-13).
Figure 10B:
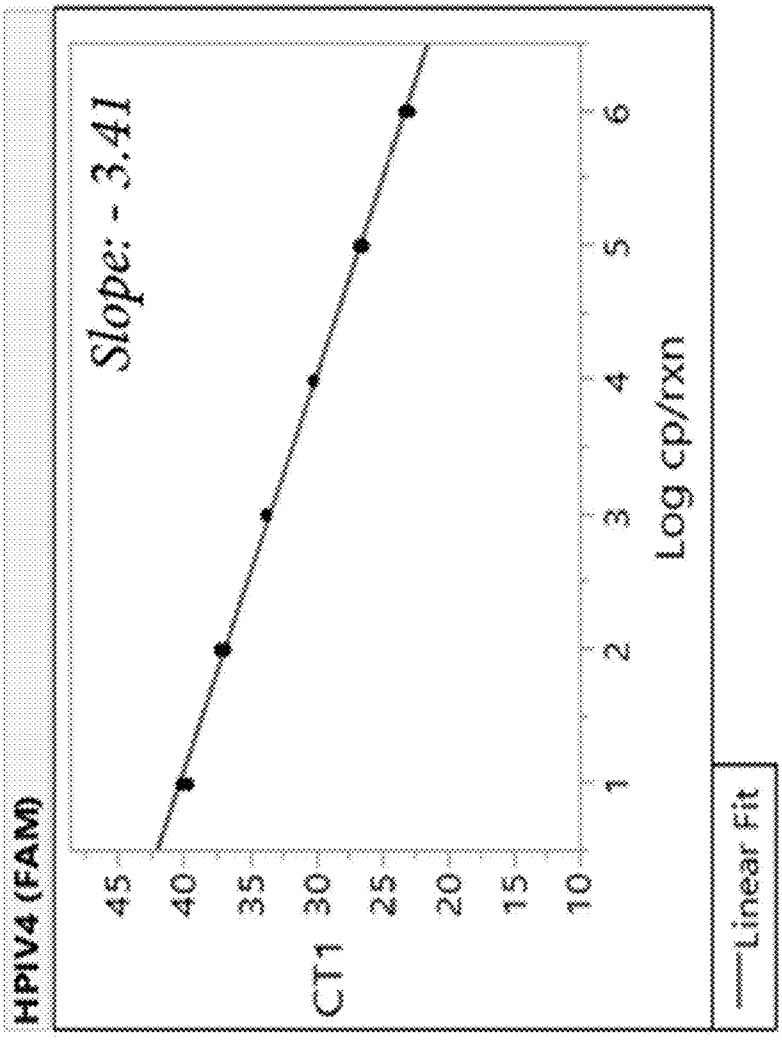
FIG. 10B shows the efficiency of the HPIV 4 assay, as described in Example 5 (using the oligonucleotides for HPIV 4, which include SEQ ID NOs: 11-13).

Example 5: HPIV 4 Primers and Probes Amplify and Detect the Large Protein Gene of HPIV 4 in a Real-Time PCR Assay HPIV 4 oligonucleotides were tested using primers/probes for detecting HPIV 3 (SEQ ID NOs:11-13). The final concentrations for the forward primer (SEQ ID NO:11) was 200 nM, the reverse primer (SEQ ID NO:12) was 200 nM, and the probe (SEQ ID NO:13) at 100 nM. The HPIV 4 assay was tested in the FAM channel. In vitro generated transcripts were used at the following concentrations: 10, $10^2$, $10^3$, $10^4$, $10^5$, and $10^6$ copies per reaction. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The results are shown in FIG. 10A, which shows PCR growth curves of a dilution series of the performance of a HPIV 4 assay. FIG. 10A shows that the HPIV 4 primers and probes (SEQ ID NOs:11-13) employed, are able to amplify and detect HPIV 4. FIG. 10B shows the efficiency of the HPIV 4 assay, and demonstrates that the HPIV 4 real-time PCR assay is efficient, showing excellent sensitivity at low target concentrations. These data show that the HPIV 4 real-time PCR assay is linear across the range tested, and can detect up to 10 copies per reaction. Taken together, these data demonstrate that the HPIV 4 real-time assay (which include oligonucleotide sequences of SEQ ID NOs:11-13) is able to detect and amplify HPIV 4.

Figure 11A:
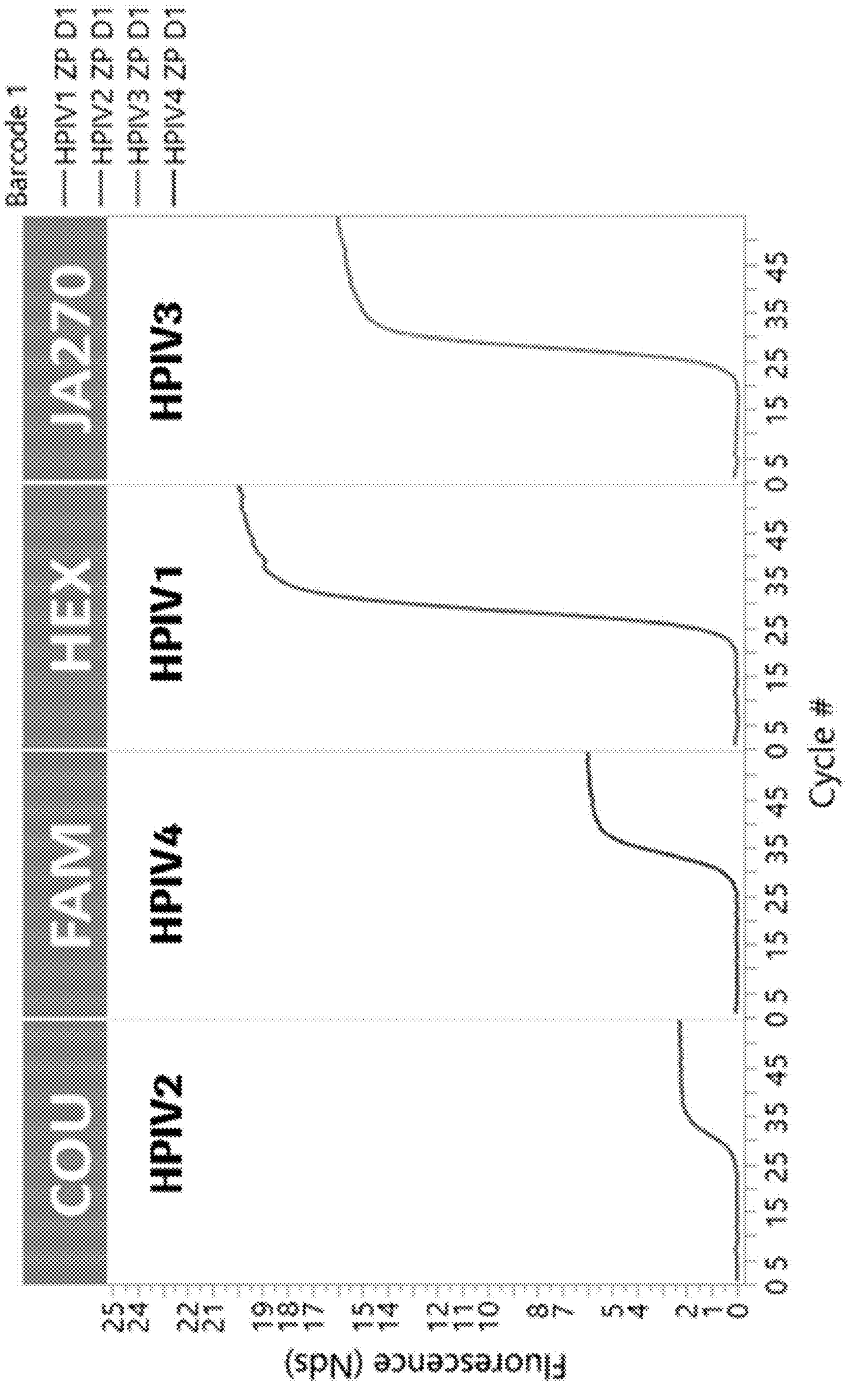

Example 6: HPIV 1-4 Primers and Probes Simultaneously Amplify and Detect Target HPIV 1-4 Nucleic Acids from Virus Eluates in an HPIV 1-4 Multiplex Real-Time PCR Assay HPIV 1-4 oligonucleotides were tested using primers/probes for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The virus eluate samples was obtained from ZeptoMetrix (Catalog No. NATRVP-IDI (Batch 318302)). The results are shown in FIG. 11A and FIG. 11B, which show PCR growth curves for each of the viral eluates1-4 multiplex assay. FIG. 11A and FIG. 11B show that the HPIV 1-4 primers and probes (SEQ ID NOs:1-5 and 7-13) employed, are able to amplify and detect HPIV 1-4 from virus eluates. That is, all virus eluates tested were detected in the expected channel. Taken together, these data demonstrate that the HPIV 1-4 multiplex real-time assay (which include oligonucleotide sequences of SEQ ID NOs:1-5 and 6-13) is able to detect and amplify viral eluates containing target nucleic acid sequences of HPIV 1-4. Furthermore, the HPIV 1-4 assay was tested for exclusivity, and to see if there was any cross-reactivity between the oligonucleotides for detecting and amplifying HPIV 1-4 with other respiratory virus targets. To that end, other respiratory virus targets were employed, including Adenovirus (AV), Enterovirus/Rhinovirus (EV/RV), and Human Metapneumovirus (HMPV) from high titer virus cultures. In this study, the oligonucleotides for detection and amplification of HPIV 1-4 (SEQ ID NOs:1-5 and 6-13) were tested in PCR assays against HPIV (HPIV 1-4) as well as AV (AV B, AV E, AV C, and AV A strains), EV/RV (EV A, EV B, EV D68, and RV A strains) and HMPV targets. Specific primers for AV, EV/RV, and HMPV targets were also employed. The results, shown in FIG. 11B, show that the oligonucleotides for HPIV 1-4 show no cross-reactivity with multiple respiratory virus targets from high titer virus cultures. Thus, these studies demonstrate the exclusivity and specificity of the HPIV 1-4 oligonucleotides for only HPIV 1-4 targets.

Figures 12A, 12B:
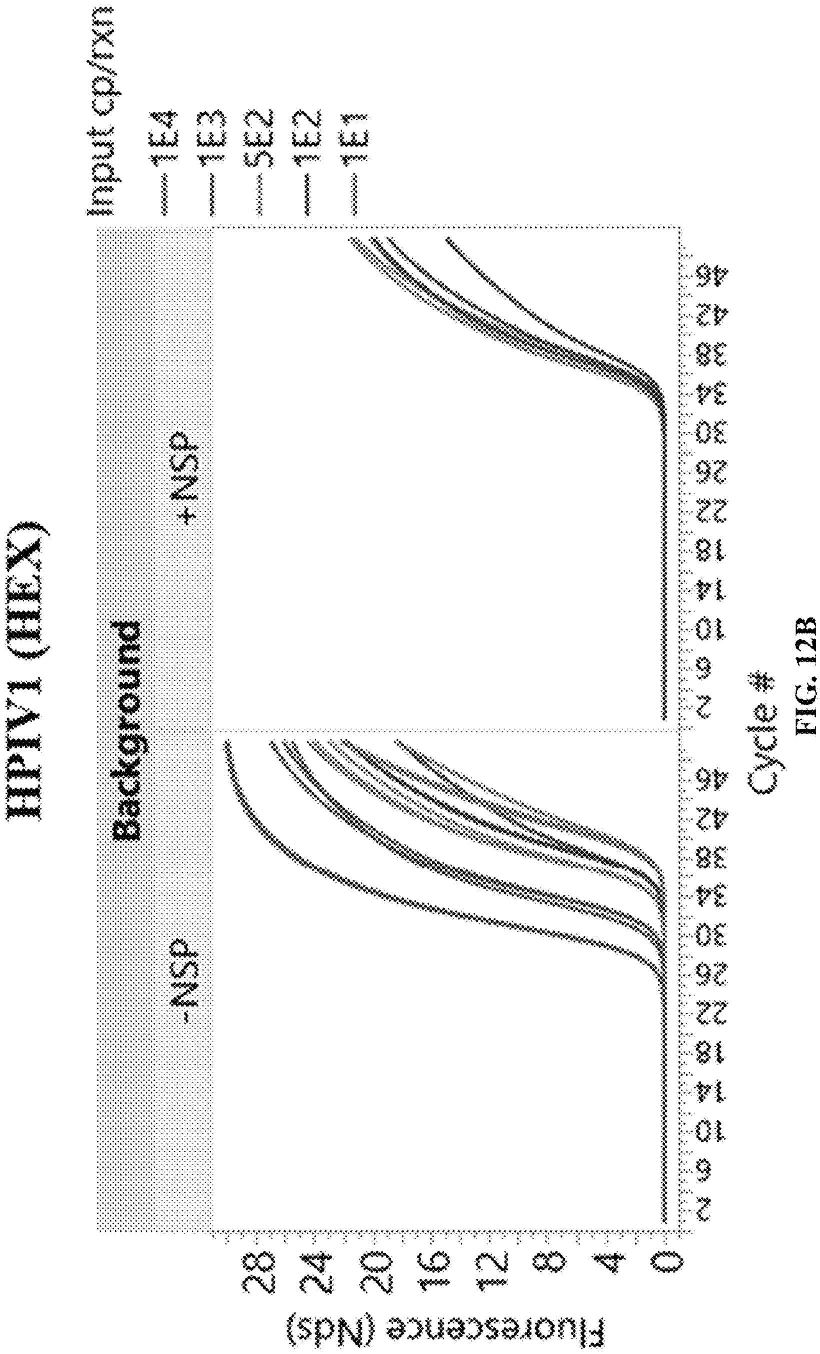
FIG. 12A shows the composition of the contrived nasopharyngeal simulated clinical sample employed in Example 7, which were used to test HPIV 1-4 oligonucleotides for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13).
FIG. 12B (HPIV 1), FIG. 12C (HPIV 2), FIG. 12D (HPIV 3), and FIG. 12E (HPIV 4) show the PCR growth curves of a dilution series of the performance of the HPIV 1-4 multiplex assay on the contrived nasopharyngeal simulated clinical sample.
Figure 12C:
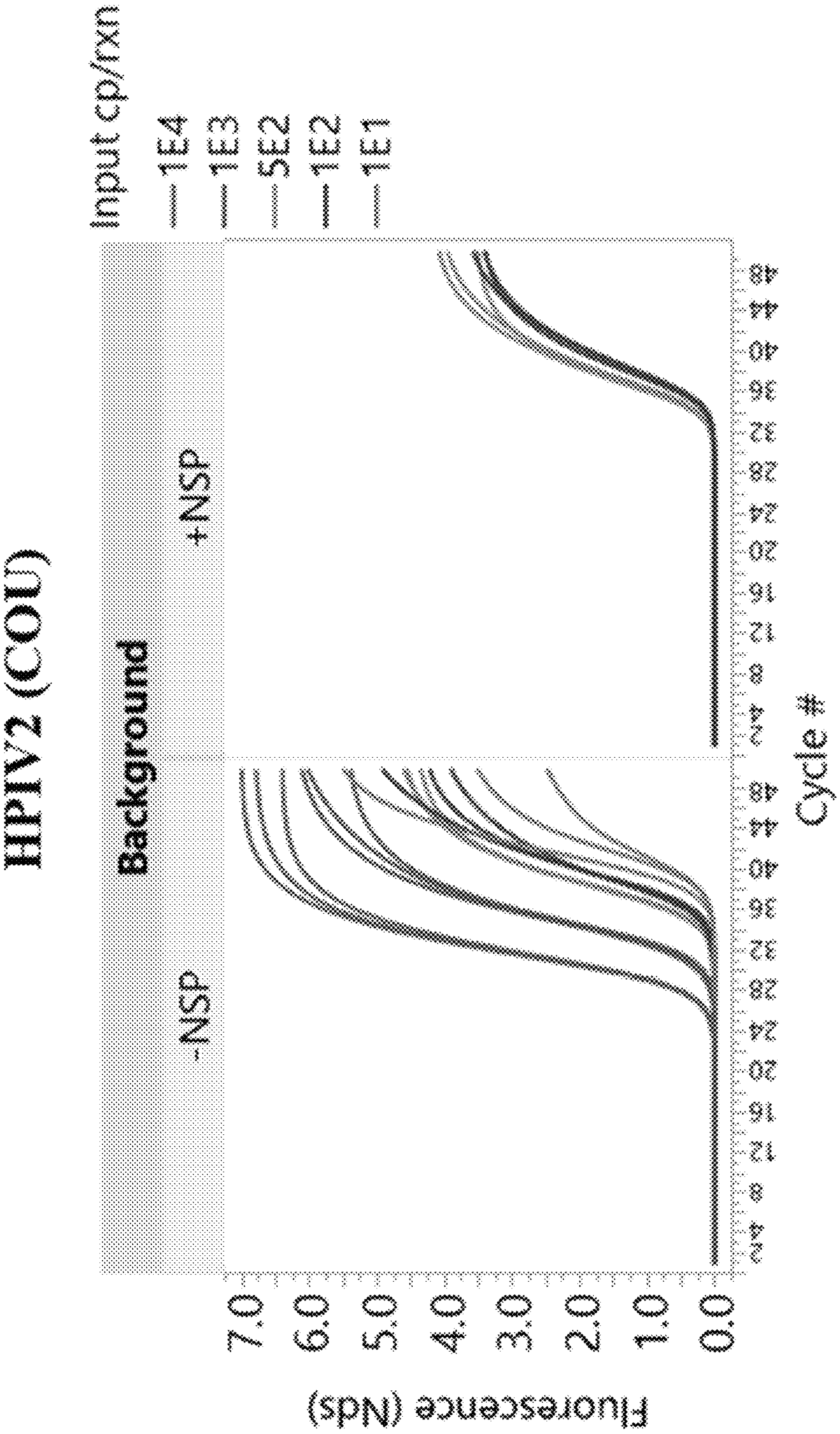
Figure 12D:
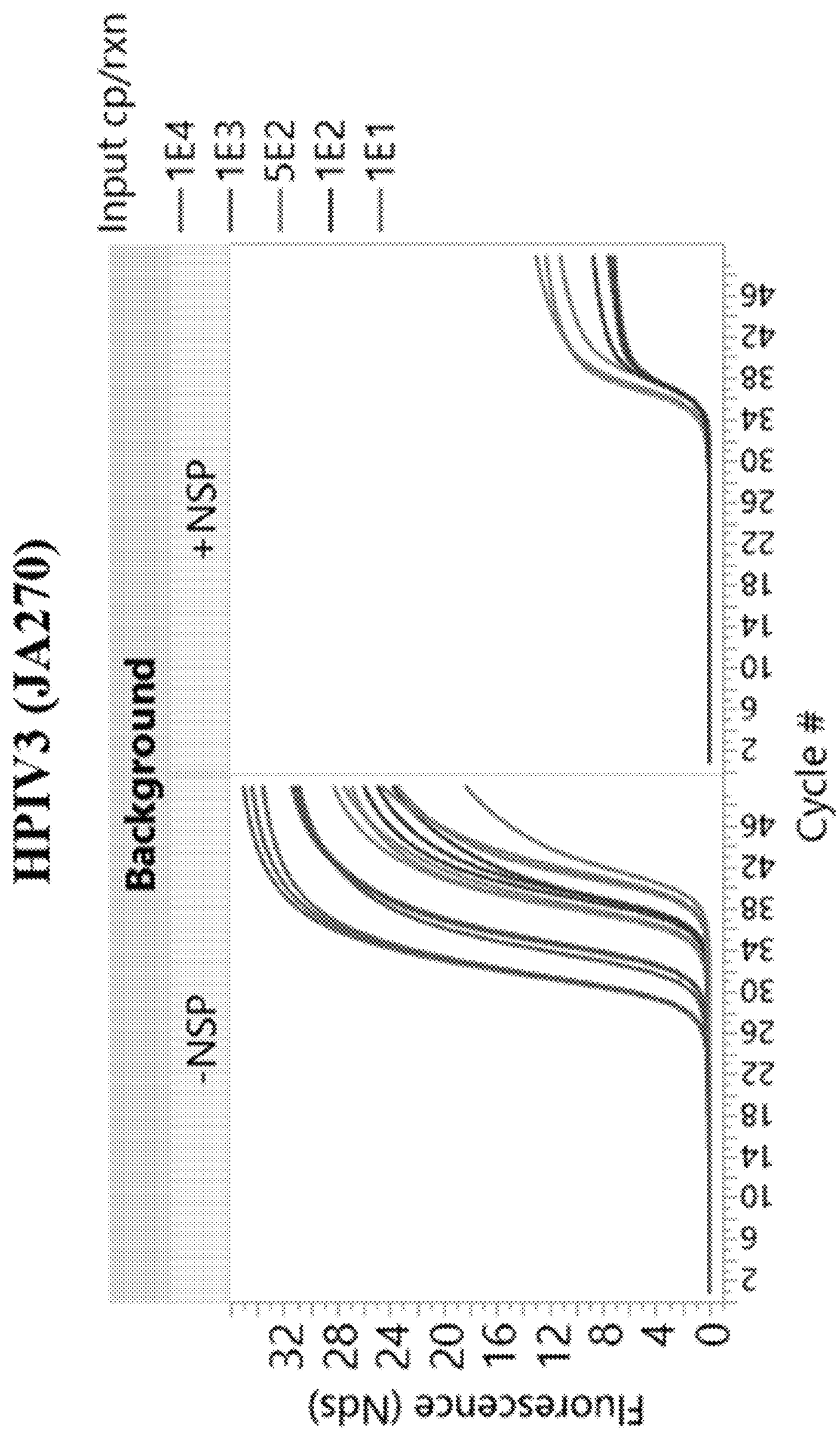
Figure 12E:
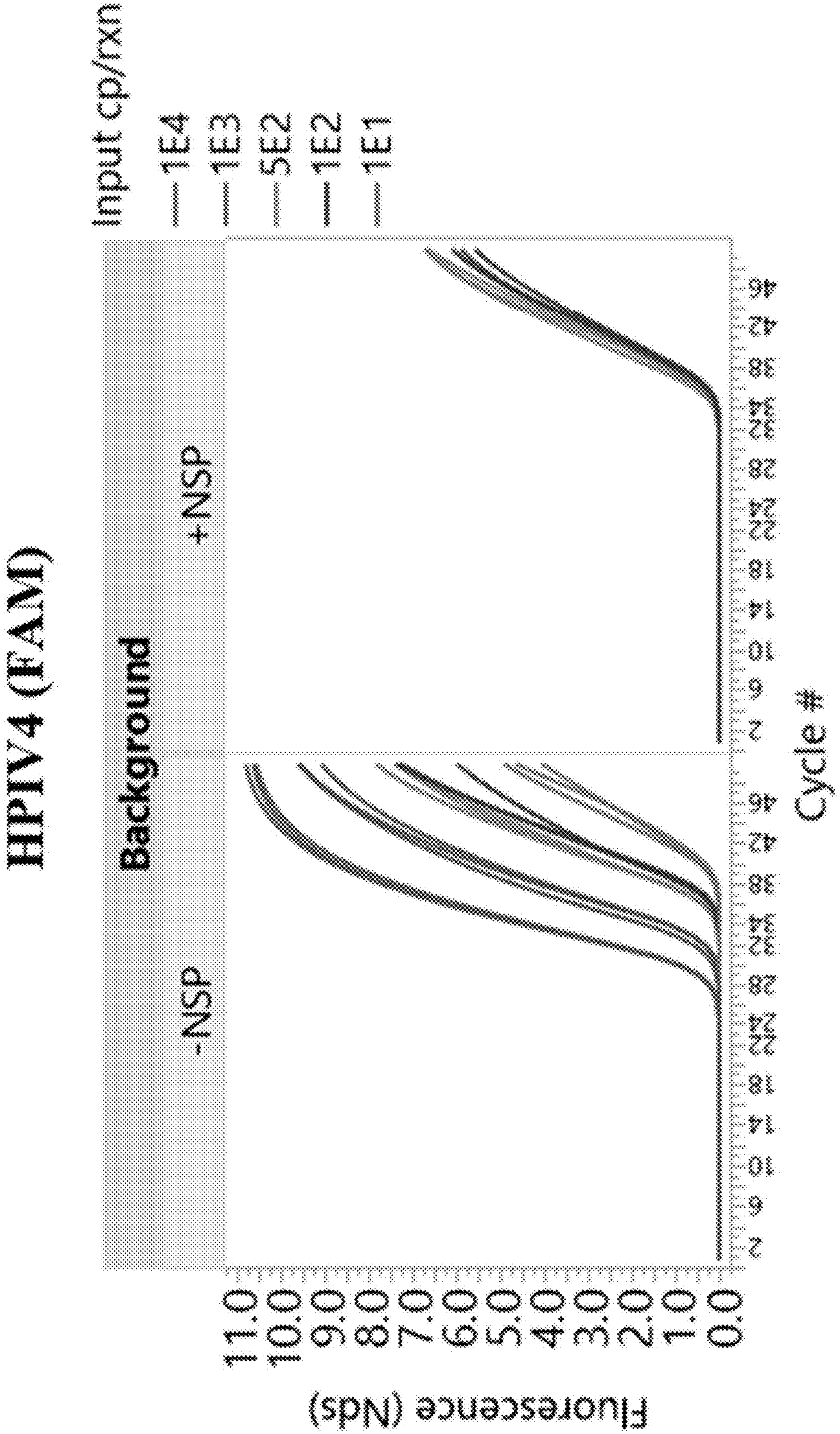

Example 7: HPIV 1-4 Primers and Probes Simultaneously Amplify and Detect Target HPIV 1-4 Nucleic Acids from a Contrived Nasopharyngeal Simulated Clinical Sample in an HPIV 1-4 Multiplex Real-Time PCR Assay HPIV 1-4 oligonucleotides were tested using primers/probes for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. The samples tested were tested in presence of contrived artificial nasopharyngeal matrix eluate, which was intended to simulate a clinical sample background, which would include cells, albumin, and mucin and were used at the following concentrations: 10, $10^2$, $10^3$, and $10^4$ copies per reaction. The composition of the matrix is shown in FIG. 12A. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The results are shown in FIG. 12B (HPIV 1), 12C (HPIV 2), 12D (HPIV 3), and 12E (HPIV 4), which shows PCR growth curves of a dilution series of the performance of a HPIV 1-4 assay. The results showed a sensitivity of the HPIV 1-4 types minimally up to 100 copies/reaction in the presence of the nasopharyngeal matrix. FIGS. 12B-12D demonstrate that the HPIV 1-4 oligonucleotides are able to simultaneously amplify and detect target HPIV 1-4 nucleic acids from a contrived artificial nasopharyngeal simulated clinical sample in a multiplex setting. Because the contrived artificial nasopharyngeal matrix simulates a nasopharyngeal clinical sample, these data suggest that the HPIV 1-4 oligonucleotides would be able to simultaneously amplify and detect target HPIV 1-4 nucleic acids from an actual nasopharyngeal sample.

Figure 13A:
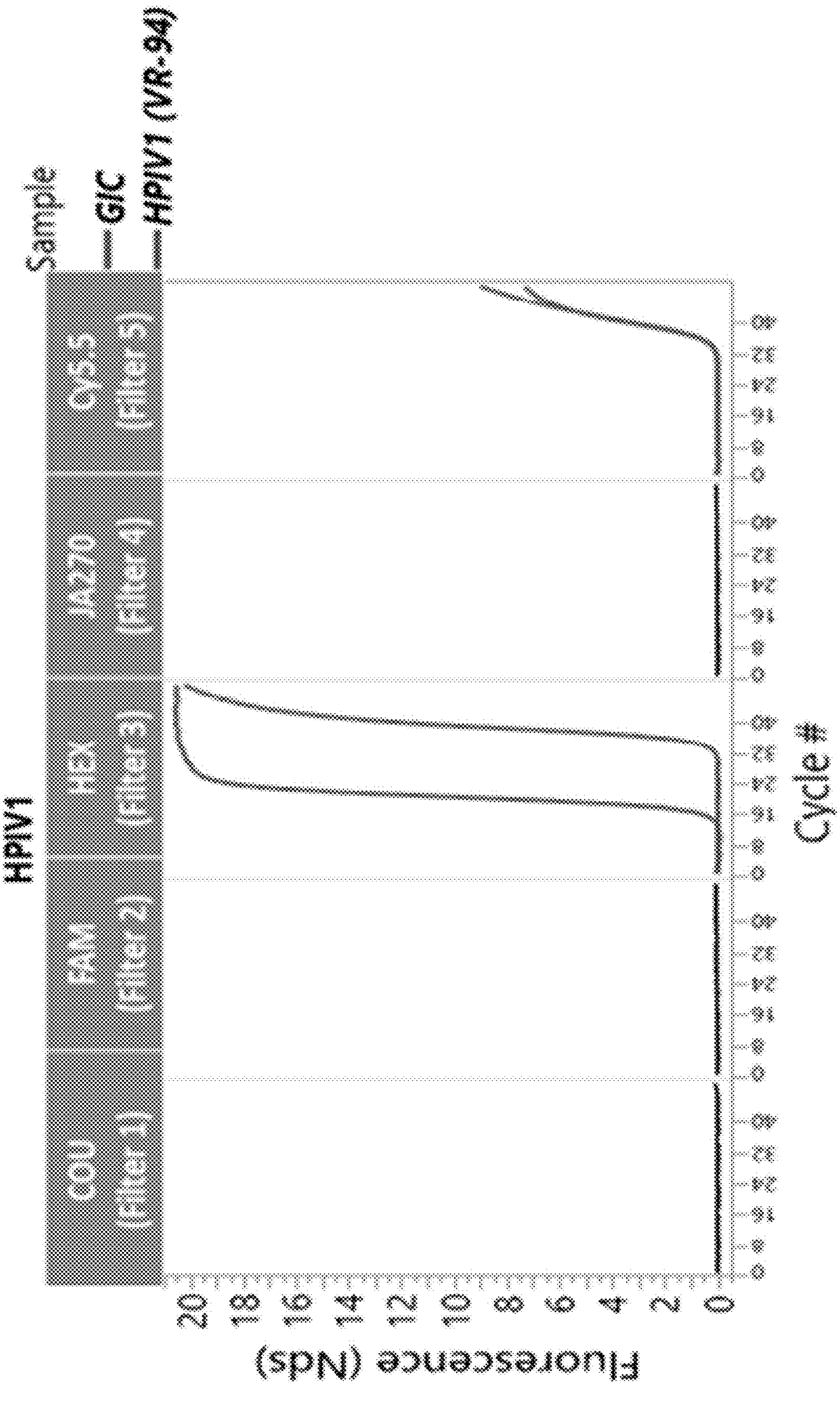
FIGS. 13A-D show that the HPIV 1-4 primers and probes simultaneously specifically detect target HPIV 1-4 nucleic acids from viral eluates in an HPIV 1-4 multiplex real-time PCR assay, as described in Example 8. HPIV 1-4 oligonucleotides were tested using primers/probes for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13). The HPIV 1-4 oligonucleotides were tested under multiplex conditions, such that the sample was simultaneously subject to exposure to all oligonucleotides for HPIV 1-4. The results are shown in FIG. 13A (HPIV 1), FIG. 13B (HPIV 2), FIG. 13C (HPIV 3), and FIG. 13D (HPIV 4), which shows PCR growth curves of a dilution series of the performance of a HPIV 1-4 assay. These results show that the HPIV 1-4 oligonucleotides are specific for their intended respective targets. As can be seen in FIGS. 13A-13D, no cross-reactivity was observed using these viral eluates in unintended channels for a specific HPIV type.
Figure 13B:
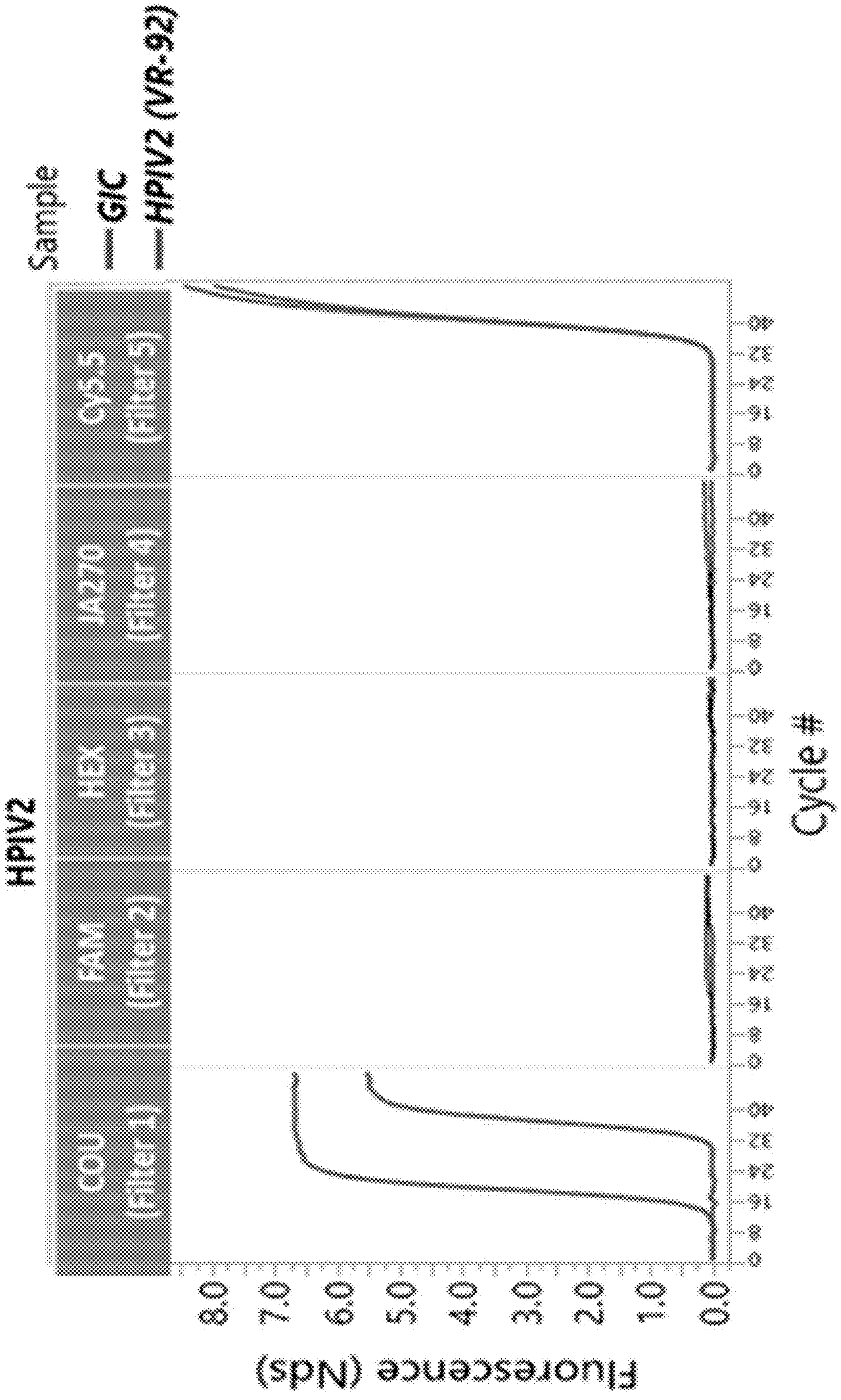
Figure 13C:
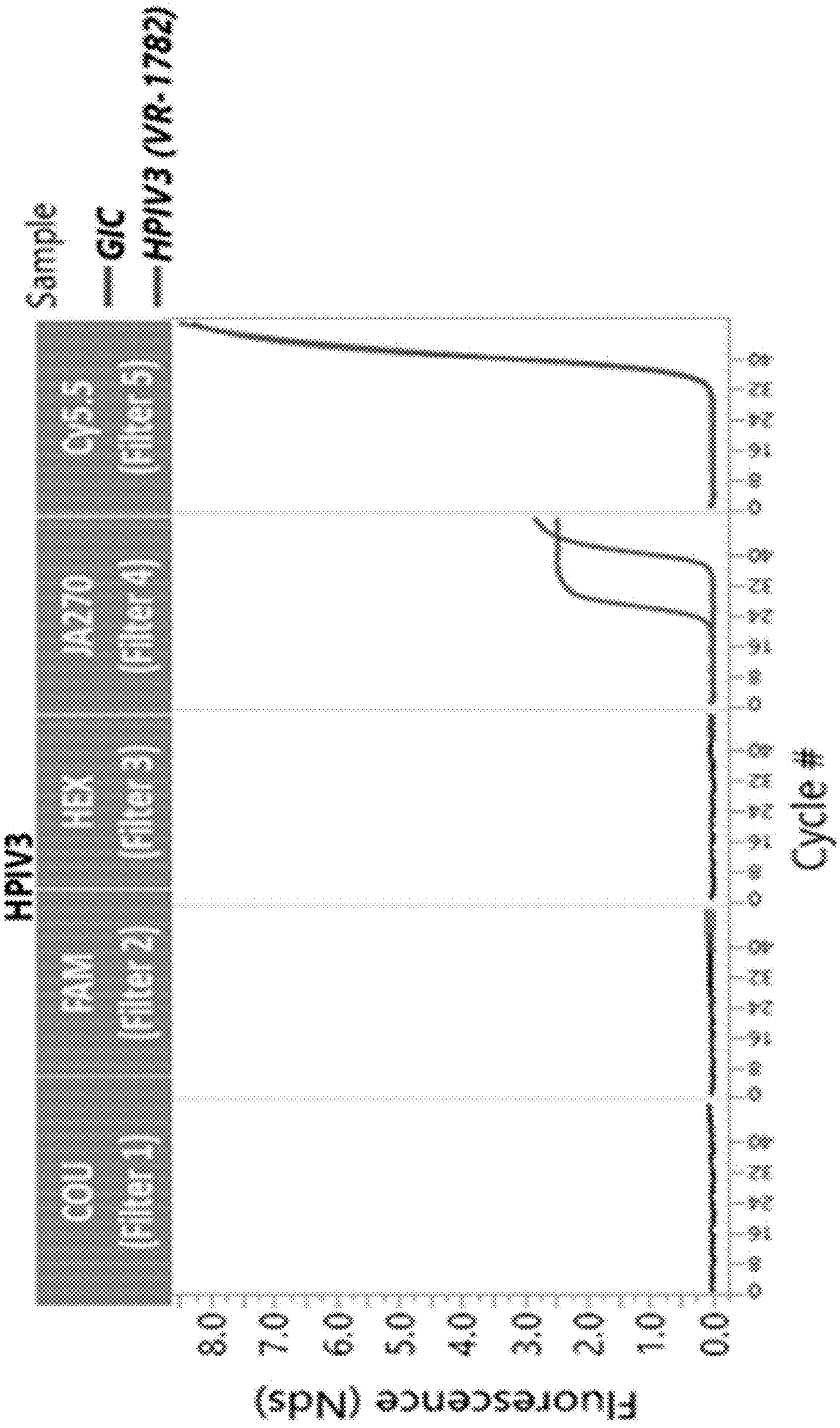
Figure 13D:
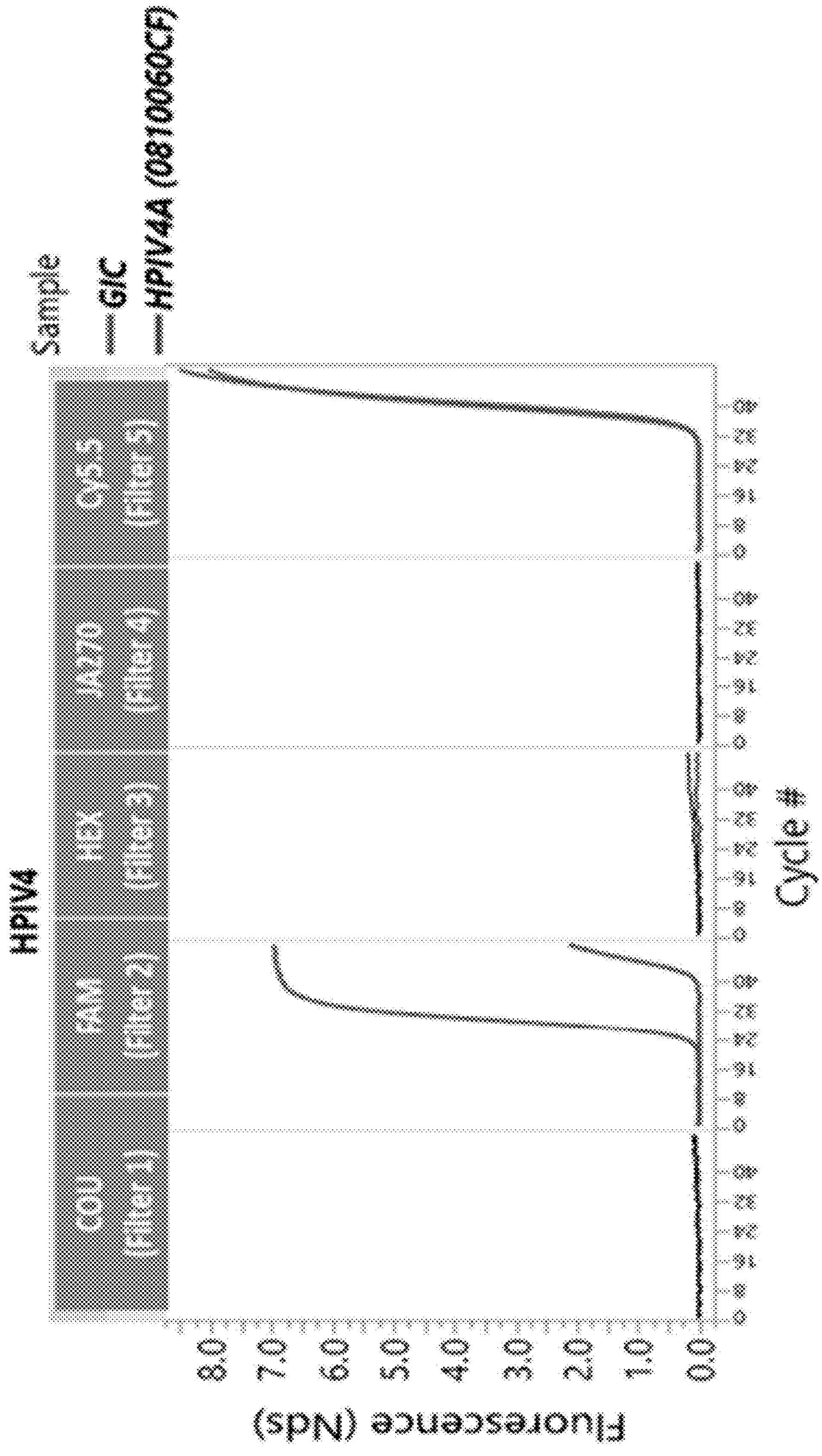

Example 8: HPIV 1-4 Primers and Probes Simultaneously Specifically Amplify and Detect Target HPIV 1-4 Nucleic Acids from Viral Eluates in an HPIV 1-4 Multiplex Real-Time PCR Assay HPIV 1-4 oligonucleotides were tested using primers/probes for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. The samples tested were viral eluates (ATCC Catalog No: HPIV1-VR-94; HPIV2-VR-92; HPIV3-VR-1782); ZeptoMetrix Catalog No: HPIV4A-0810060CF), which were tested at two concentrations: neat and at a 1:100,000 dilution. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. These studies were designed to test the specificity of the HPIV 1-4 oligonucleotides on viral eluates. The results are shown in FIG. 13A (HPIV 1), FIG. 13B (HPIV 2), FIG. 13C (HPIV 3), and FIG. 13D (HPIV 4), which shows PCR growth curves of a dilution series of the performance of a HPIV 1-4 assay. These results show that the HPIV 1-4 oligonucleotides are specific for their intended respective targets. As can be seen in FIGS. 13A-13D, no cross-reactivity was observed using these viral eluates in unintended channels for a specific HPIV type. Taken together, these studies demonstrate that the oligonucleotides for HPIV 1-4 specifically amplify and detect their intended targets in a multiplex setting.

Example 9: HPIV 1-4 Primers and Probes Demonstrate Specificity for HPIV 1-4 Targets by Failing to Amplify and Detect HPIV 1-4 Targets in Clinical Samples Known to be Negative for HPIV 1-4

Figure 14A:
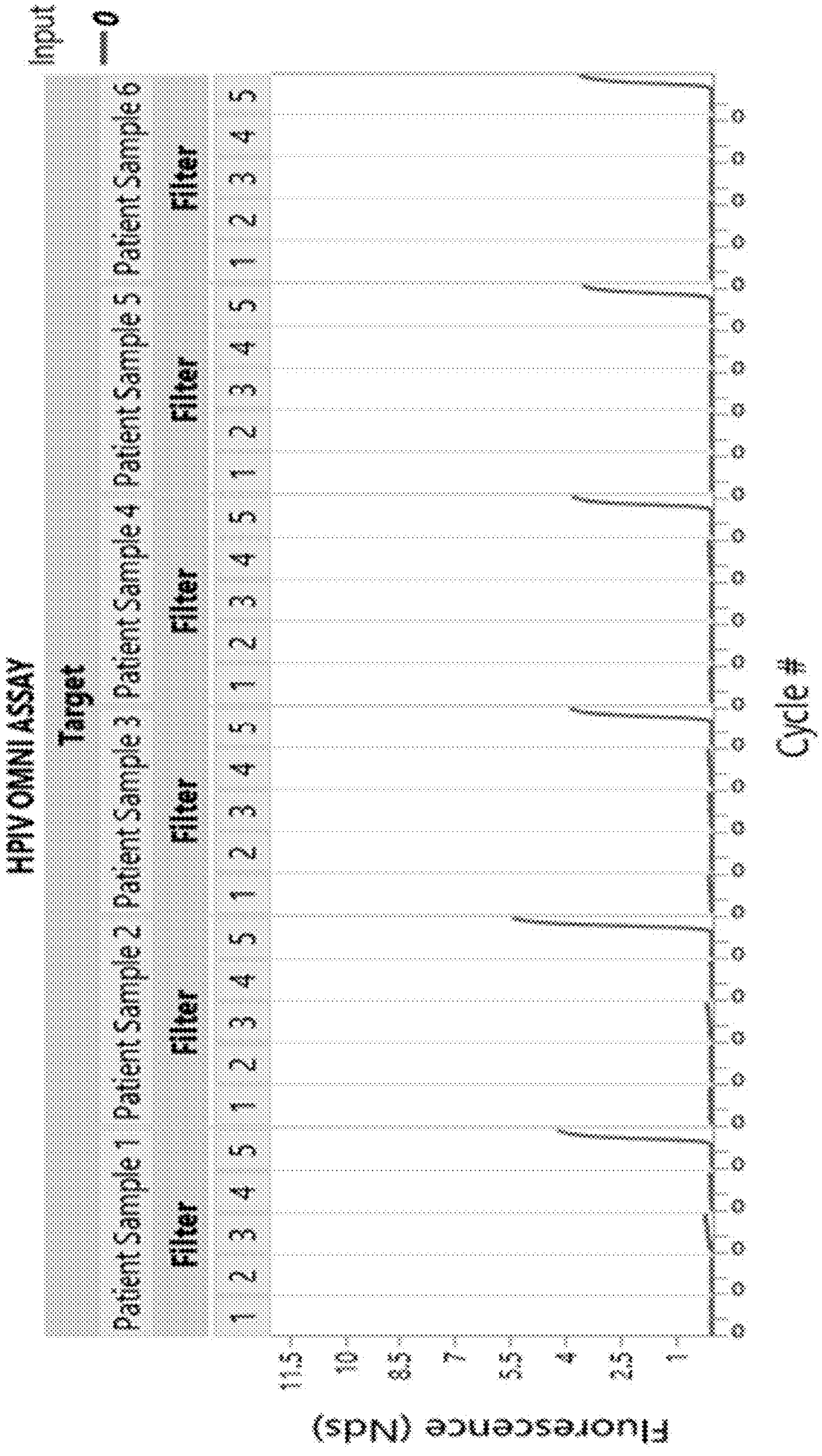
FIG. 14A and FIG. 14B show PCR growth curves of the performance of the HPIV 1-4 multiplex assay on samples known to be negative for any and all of HPIV 1-4, as described in Example 9. HPIV 1-4 oligonucleotides were tested using primers/probes for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13). The HPIV 1-4 oligonucleotides were tested under multiplex conditions, such that the sample was simultaneously subject to exposure to all oligonucleotides for HPIV 1-4. These studies were designed to test the specificity of the HPIV 1-4 oligonucleotides on HPIV 1-4-negative eluates. The results, as shown in FIG. 14A and FIG. 14B, show no amplification in any of the channels with any of the HPIV 1-4 oligonucleotides against nasopharyngeal eluates known to be negative for HPIV 1-4.
Figure 14B:
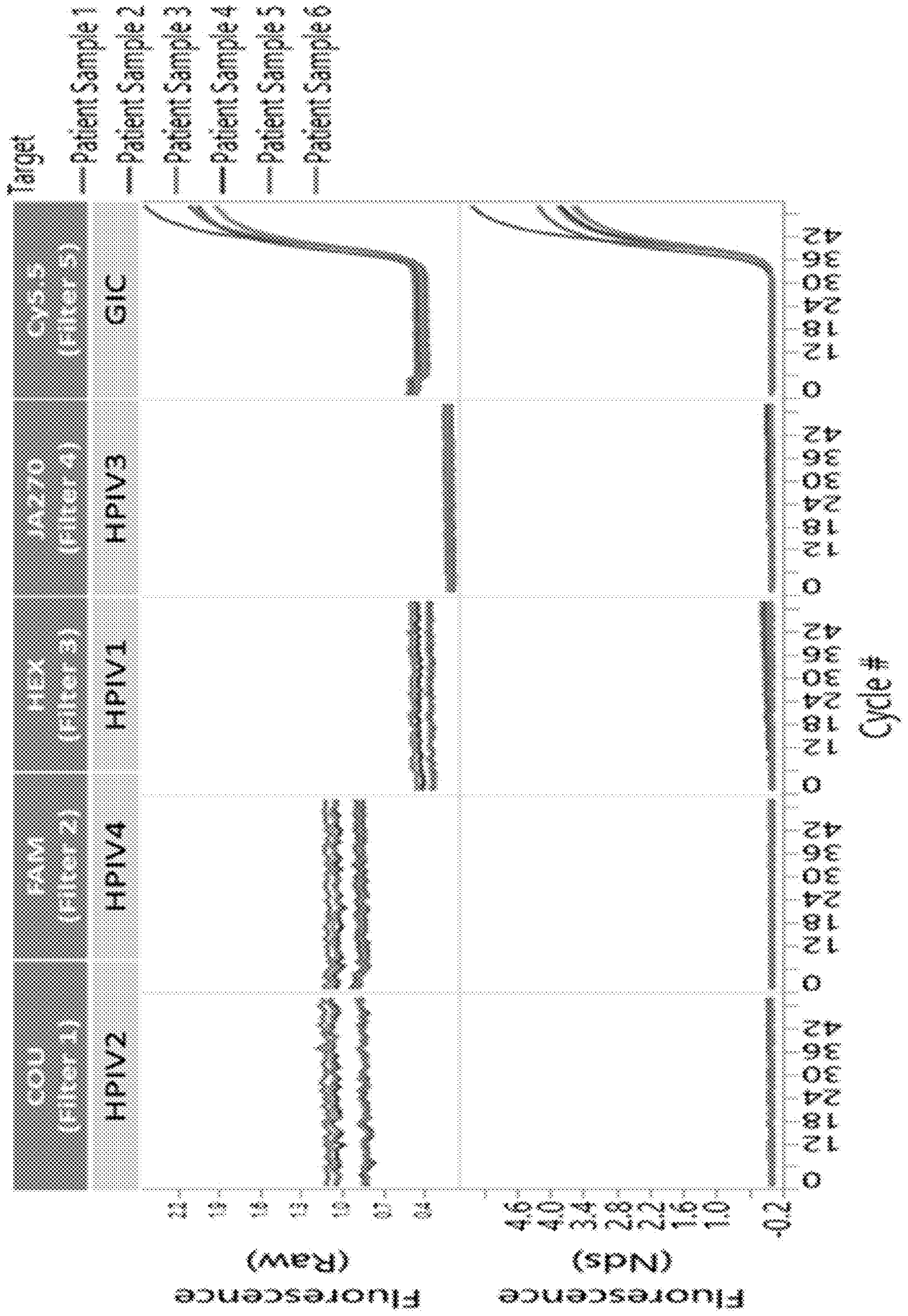

HPIV 1-4 oligonucleotides were tested using primers/probes for detecting HPIV 1 (SEQ ID NOs:1-3), HPIV 2 (SEQ ID NOs:4, 5, and 7), HPIV 3 (SEQ ID NOs:8-10), and HPIV 4 (SEQ ID NOs:11-13). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. The samples tested were nasopharyngeal eluates from six individual patients known to be negative for HPIV 1-4. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. These studies were designed to test the specificity of the HPIV 1-4 oligonucleotides on HPIV 1-4-negative eluates. The results are shown in FIG. 14A and FIG. 14B, which show PCR growth curves of the performance of a HPIV 1-4 assay. These results show no amplification in any of the channels with any of the HPIV 1-4 oligonucleotides against nasopharyngeal eluates known to be negative for HPIV 1-4. These results show that the oligonucleotides for HPIV 1-4 do not cross-react and/or inadvertently amplify nucleic acids, when the intended targets are not present in a nasopharyngeal eluate.

Example 10: HPIV 1-4 Primers and Probes Simultaneously Specifically Amplify and Detect Target HPIV 1-4 Nucleic Acids from Viral Eluates in an HPIV 1-4 Multiplex Real-Time PCR Assay HPIV 1 oligonucleotides were tested using primers/probes for detecting HPIV 1 (SEQ ID NOs:1-3). HPIV 1-4 oligonucleotides were tested using primers/probes for detecting HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19). The HPIV 1-4 oligonucleotides are shown in FIG. 15. In vitro generated transcripts were used at the following concentrations: 10, $10^2$, $10^3$, $10^4$, $10^5$ and $10^6$ copies per reaction. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. For HPIV 1, the forward primer (SEQ ID NO:1) is at a concentration of 400 nM, the reverse primer (SEQ ID NO:2) is at a concentration of 300 nM, and the probe (SEQ ID NO:3) is at a concentration of 100 nM. For HPIV 2, the forward primer (SEQ ID NO:4) is at a concentration of 200 nM, the reverse primer (SEQ ID NO:5) is at a concentration of 150 nM, and the probe (SEQ ID NO:6) is at a concentration of 100 nM. For HPIV 3, the forward primer (SEQ ID NO:15) is at a concentration of 500 nM, the reverse primer (SEQ ID NO:16) is at a concentration of 300 nM, and the probe (SEQ ID NO:17) is at a concentration of 100 nM. For HPIV 4, the forward primers (SEQ ID NOs:11 and 18) are at a concentrations of 100 nM and 400 nM, respectively, the reverse primer (SEQ ID NO:19) is at a concentration of 400 nM, and the probe (SEQ ID NO:13) is at a concentration of 100 nM. The results are shown in FIG. 16A (HPIV 1), FIG. 16B (HPIV 2), FIG. 16C (HPIV 3), and FIG. 16D (HPIV 4), which shows PCR growth curves of a dilution series of the performance of a HPIV 1-4 assays.

Figure 16A:
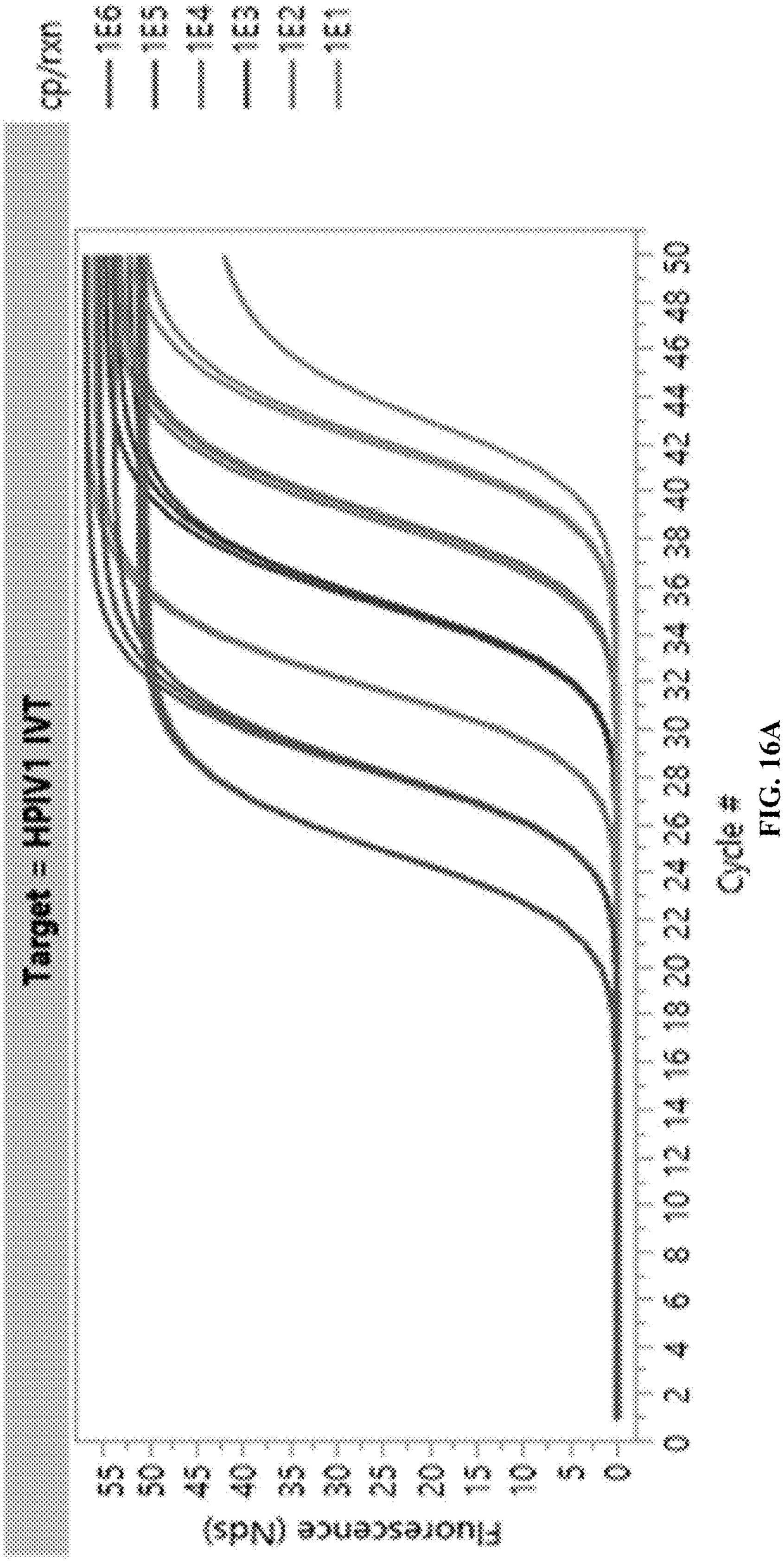
FIG. 16A shows PCR growth curves of a dilution series of the IVT transcript for HPIV 1, as described in Example 10 (using the oligonucleotides for HPIV 1, which include SEQ ID NOs:1-3).
Figure 16B:
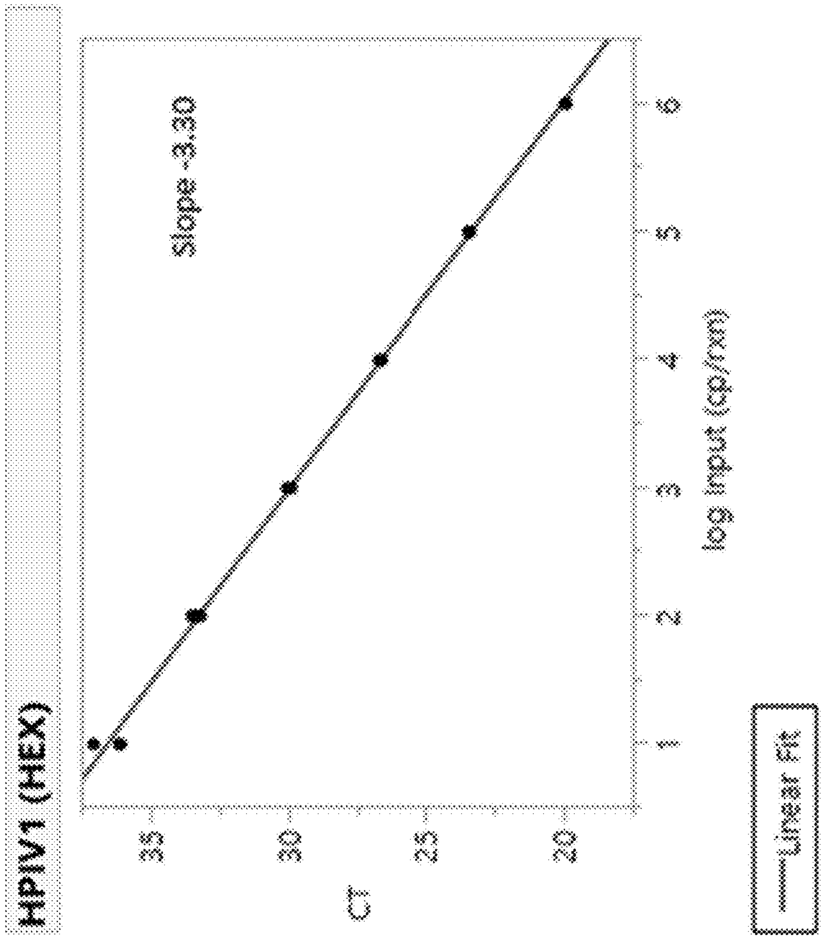
FIG. 16B shows the efficiency of the HPIV 1 assay, as described in Example 10 (using the oligonucleotides for HPIV 1, which include SEQ ID NOs: 1-3).
Figure 16C:
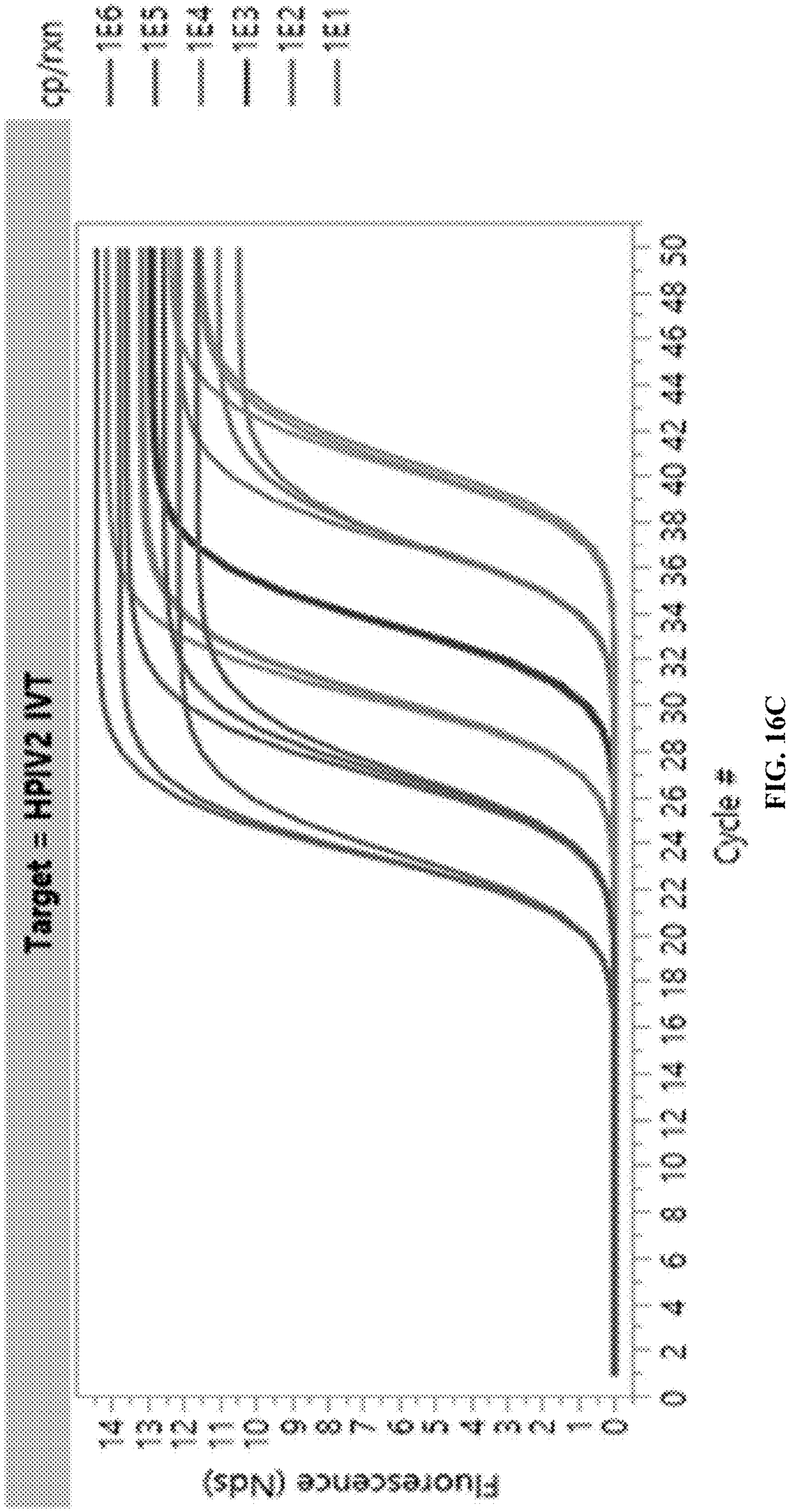
FIG. 16C shows PCR growth curves of a dilution series of the IVT transcript for HPIV 2, as described in Example 10 (using the oligonucleotides for HPIV 2, which include SEQ ID NOs:4-6).
Figure 16D:
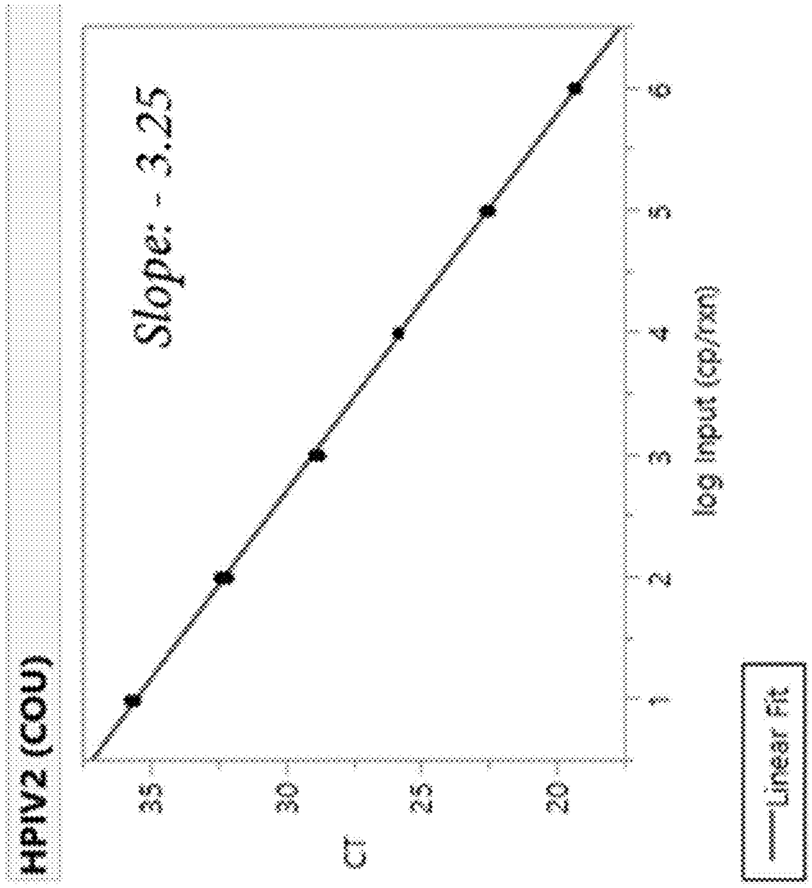
FIG. 16D shows the efficiency of the HPIV 2 assay, as described in Example 10 (using the oligonucleotides for HPIV 2, which include SEQ ID NOs: 4-6).
Figure 16E:
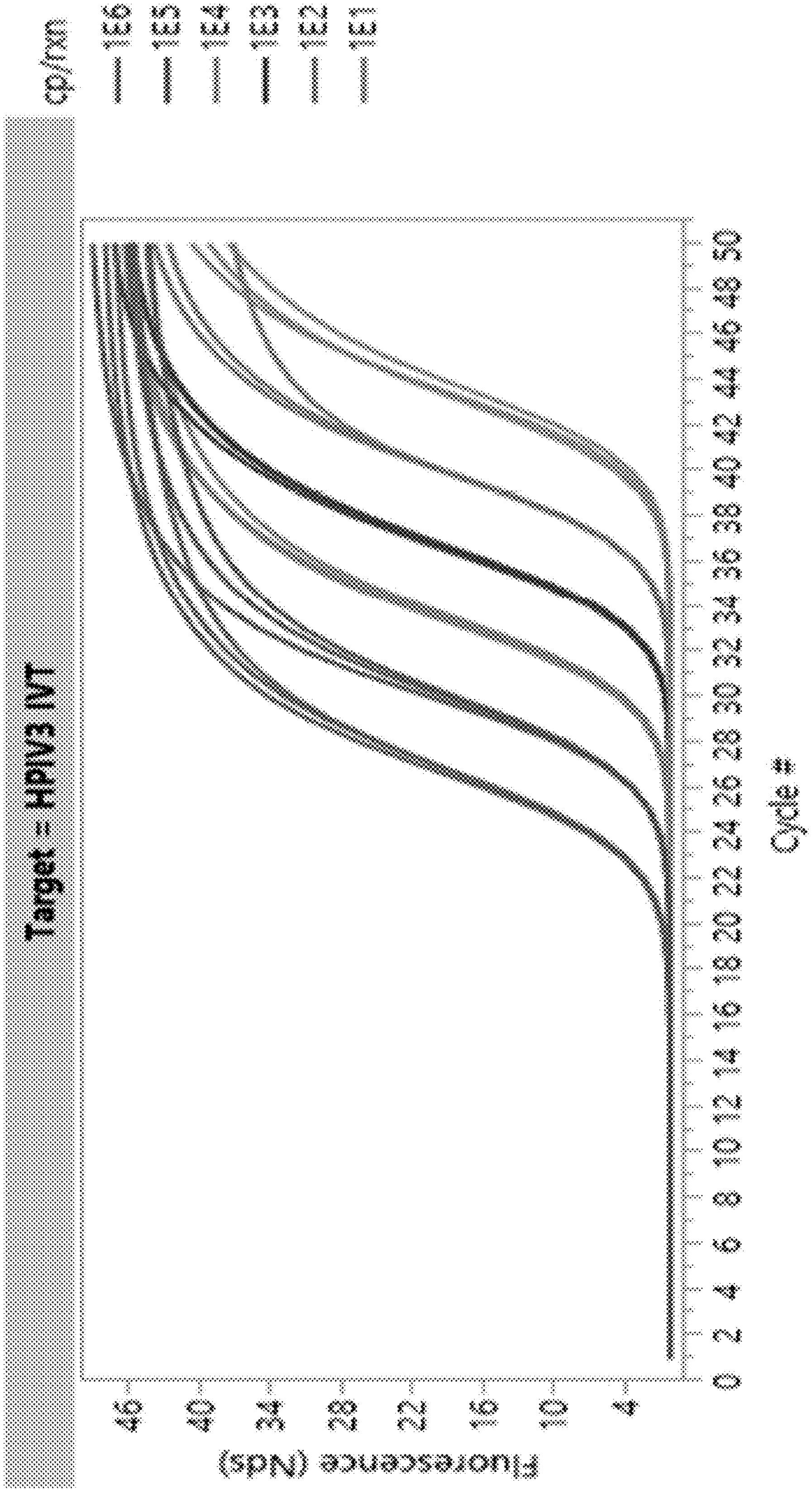
FIG. 16E shows PCR growth curves of a dilution series of the IVT transcript for HPIV 3, as described in Example 10 (using the oligonucleotides for HPIV 3, which include SEQ ID NOs:15-17).
Figure 16F:
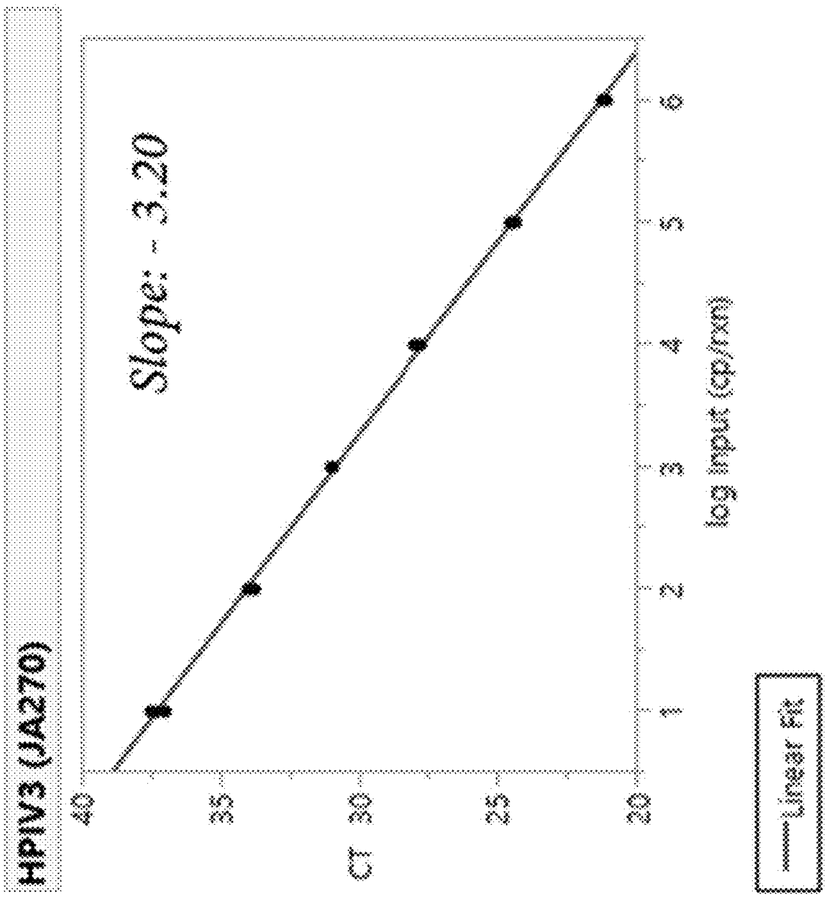
FIG. 16F shows the efficiency of the HPIV 3 assay, as described in Example 10 (using the oligonucleotides for HPIV 3, which include SEQ ID NOs: 15-17).
Figure 16G:
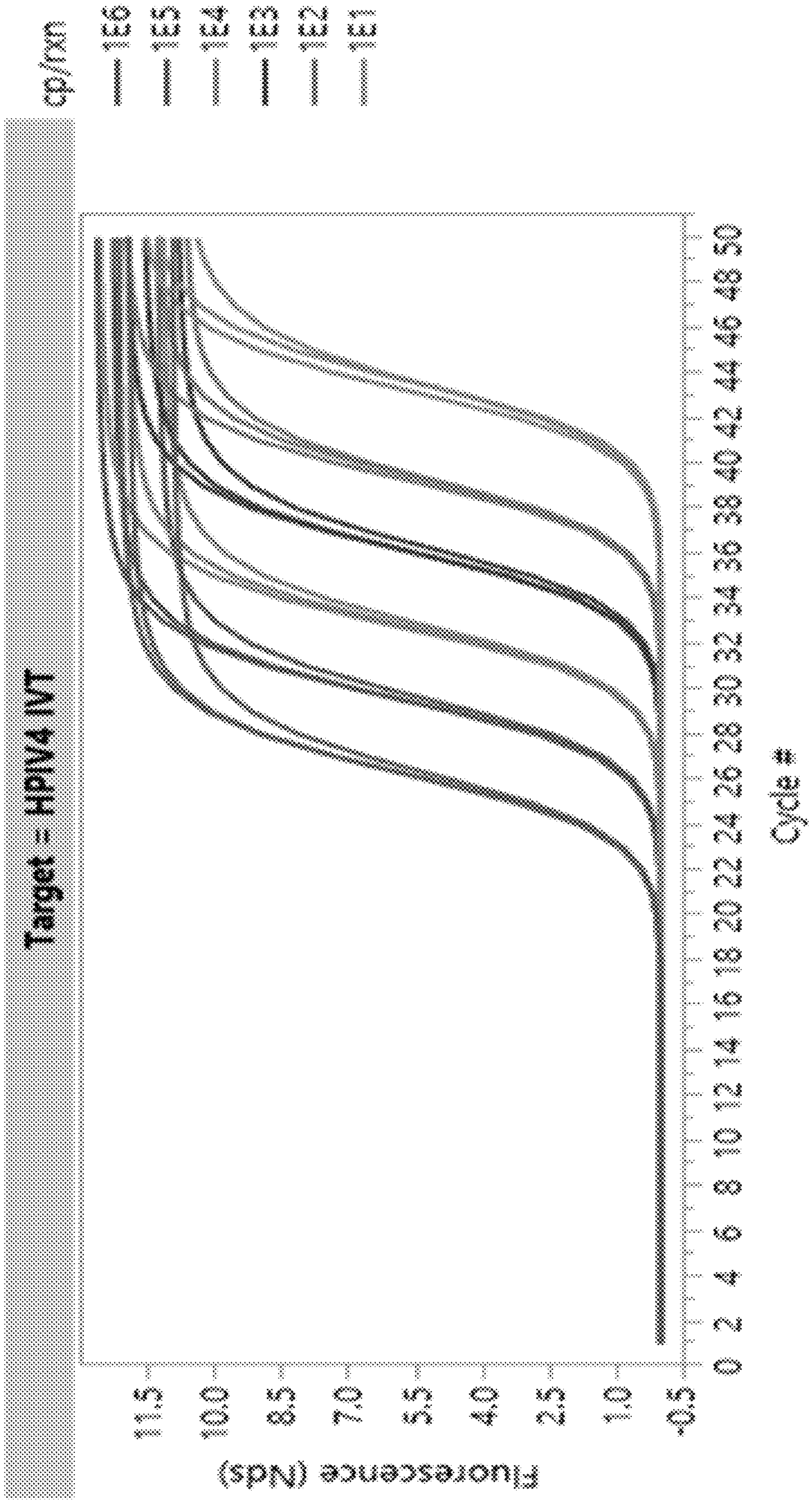
FIG. 16G shows PCR growth curves of a dilution series of the IVT transcript for HPIV 4, as described in Example 10 (using the oligonucleotides for HPIV 4, which include SEQ ID NOs:11, 13, 18, and 19).
Figure 16H:
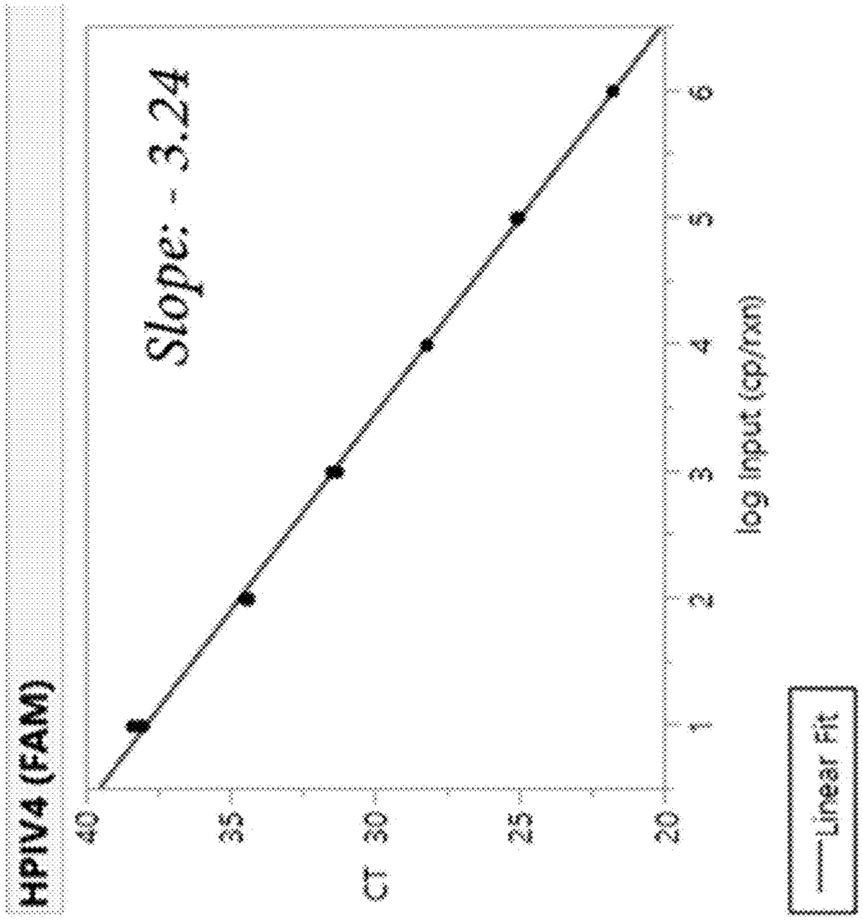
FIG. 16H shows the efficiency of the HPIV 4 assay, as described in Example 10 (using the oligonucleotides for HPIV 4, which include SEQ ID NOs: 11, 13, 18, and 19).

The results are shown in FIG. 16A, which shows PCR growth curves of a dilution series of the performance of a HPIV 1 assay. FIG. 16A shows that the HPIV 1 primers and probes (SEQ ID NOs:1-3) employed, are able to amplify and detect HPIV 1. FIG. 16B shows the efficiency of the HPIV 1 assay, and demonstrates that the HPIV 1 real-time PCR assay is efficient, showing excellent sensitivity at low target concentrations. The results are shown in FIG. 16C, which shows PCR growth curves of a dilution series of the performance of a HPIV 2 assay. FIG. 16C shows that the HPIV 2 primers and probes (SEQ ID NOs:4-6) employed, are able to amplify and detect HPIV 2. FIG. 16D shows the efficiency of the HPIV 2 assay, and demonstrates that the HPIV 2 real-time PCR assay is efficient, showing excellent sensitivity at low target concentrations. The results are shown in FIG. 16E, which shows PCR growth curves of a dilution series of the performance of a HPIV 3 assay. FIG. 16E shows that the HPIV 3 primers and probes (SEQ ID NOs:15-17) employed, are able to amplify and detect HPIV 3. FIG. 16F shows the efficiency of the HPIV 3 assay, and demonstrates that the HPIV 3 real-time PCR assay is efficient, showing excellent sensitivity at low target concentrations. The results are shown in FIG. 16G, which shows PCR growth curves of a dilution series of the performance of a HPIV 4 assay. FIG. 16G shows that the HPIV 4 primers and probes (SEQ ID NOs:11, 13, 18, and 19) employed, are able to amplify and detect HPIV 4. FIG. 16H shows the efficiency of the HPIV 4 assay, and demonstrates that the HPIV 4 real-time PCR assay is efficient, showing excellent sensitivity at low target concentrations. These data show that the real-time PCR assays for HPIV 1, HPIV 2, HPIV 3, and HPIV 4 are linear across the range tested, and can detect up to 10 copies of target per reaction. Taken together, these data demonstrate that the HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19) real-time assays are able to detect and amplify HPIV 1, HPIV 2, HPIV 3, and HPIV 4, respectively.

Example 11: HPIV 1-4 Primers and Probes Simultaneously Amplify and Detect Target HPIV 1-4

Figure 17A:
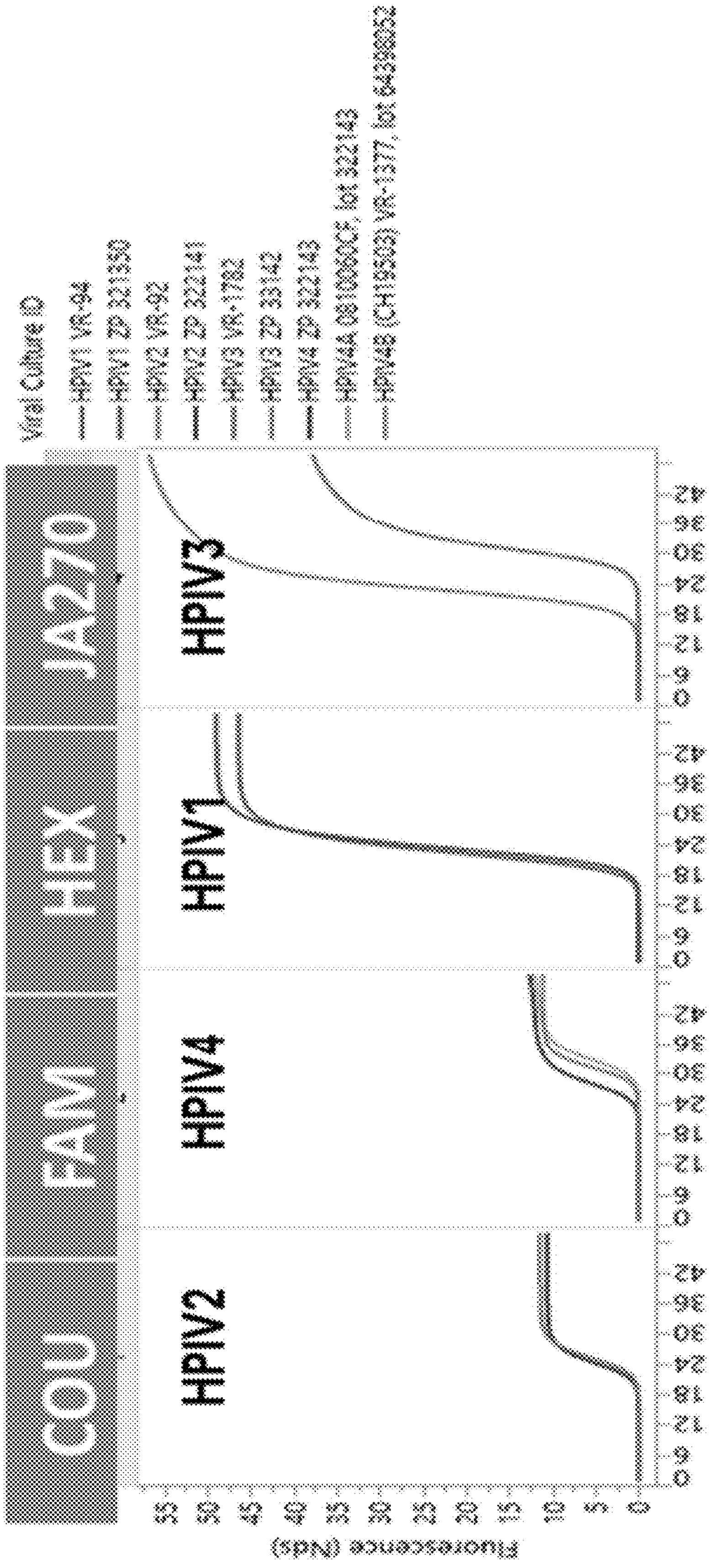
FIG. 17A shows the growth curve of the performance of the HPIV 1-4 primers and probes simultaneously amplifying and detecting HPIV 1-4 target nucleic acids from virus eluates, in singleplex fashion, as described in Example 11, using the following oligonucleotides: HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19).

Nucleic Acids from Virus Eluates in an HPIV 1-4 Multiplex Real-Time PCR Assay HPIV 1-4 oligonucleotides were tested using primers/probes for detecting HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. HPIV 1-4 oligonucleotides were tested using primers/probes for detecting HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19). Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The viral cultures were obtained from ZeptoMetrix (Catalog No. NATRVP-IDI (Batch 318302)) and ATCC. The results are shown in FIG. 17A, which shows PCR growth curves for each of the viral eluates HPIV 1-4 singleplex assay. FIG. 17A shows that the HPIV 1-4 primers and probes (HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19)) employed, are able to amplify and detect HPIV 1-4 from virus eluates. That is, all virus eluates tested were detected in the expected channel. Taken together, these data demonstrate that the HPIV 1-4 multiplex real-time assay (HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19)) is able to detect and amplify viral eluates containing target nucleic acid sequences of HPIV 1-4.

Figure 17B:
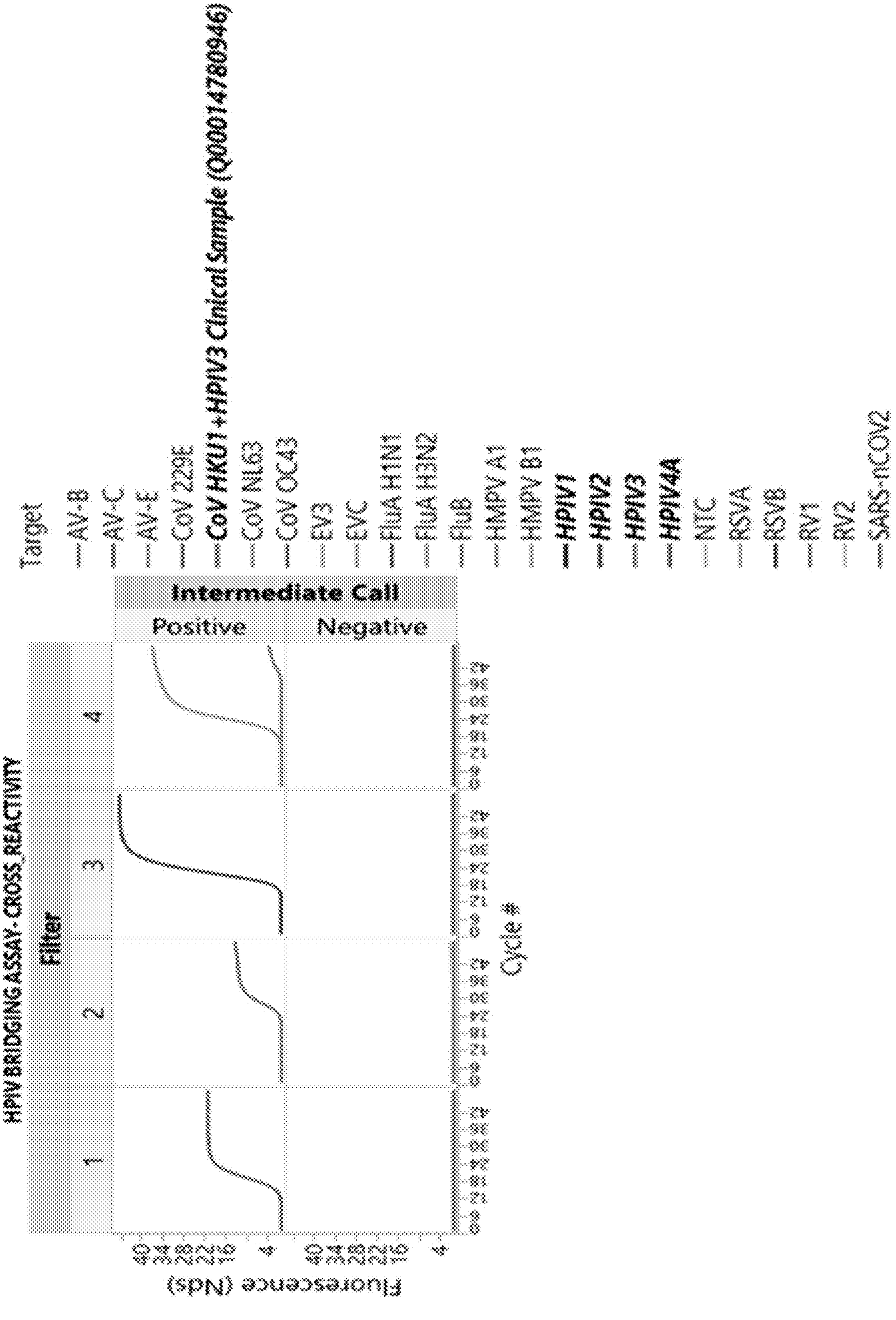
FIG. 17B shows the growth curve of the performance of the HPIV 1-4 primers and probes simultaneously amplifying and detecting HPIV 1-4 target nucleic acids in the presence of other respiratory virus targets in order to test for exclusivity as described in Example 11, using the following oligonucleotides: HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19).

Furthermore, the HPIV 1-4 assay was tested for exclusivity, and to see if there was any cross-reactivity between the oligonucleotides for detecting and amplifying HPIV 1-4 with other respiratory virus targets. To that end, other respiratory virus targets were employed, including Adenovirus (AdV), Human Coronaviruses (CoV), Enterovirus (EV), Influenza, Human Metapneumovirus (HMPV), Respiratory Syncytial Virus (RSV), Rhinovirus (RV), and severe acute respiratory syndrome coronavirus 2 (SARS-CoV-2) from high titer virus cultures. In this study, the oligonucleotides for detection and amplification of HPIV 1-4 (HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19)) were tested in PCR assays against HPIV (HPIV 1-4) as well as AdV (AdV-B, AdV-E and AdV-C strains), CoV (CoV 229E, CoV HKU1+HPIV3 (Clinical Sample), CoV NL63, CoV 0C43), EV (EV D68 and EV C), Influenza (FluA H1N1, FluA H3N2, and FluB), HMPV (HMPV A1 and HMPV B1), RSV (RSVA and RSVB), Rhinovirus (RV A and RV B), and SARS-CoV-2 eluates. The results, shown in FIG. 17B, show that the oligonucleotides for HPIV 1-4 in a multiplex setting show no cross-reactivity with multiple respiratory virus targets from high titer multiple respiratory virus cultures. Thus, these studies demonstrate the exclusivity and specificity of the HPIV 1-4 oligonucleotides for only HPIV 1-4 targets in a multiplex setting.

Figure 18B:
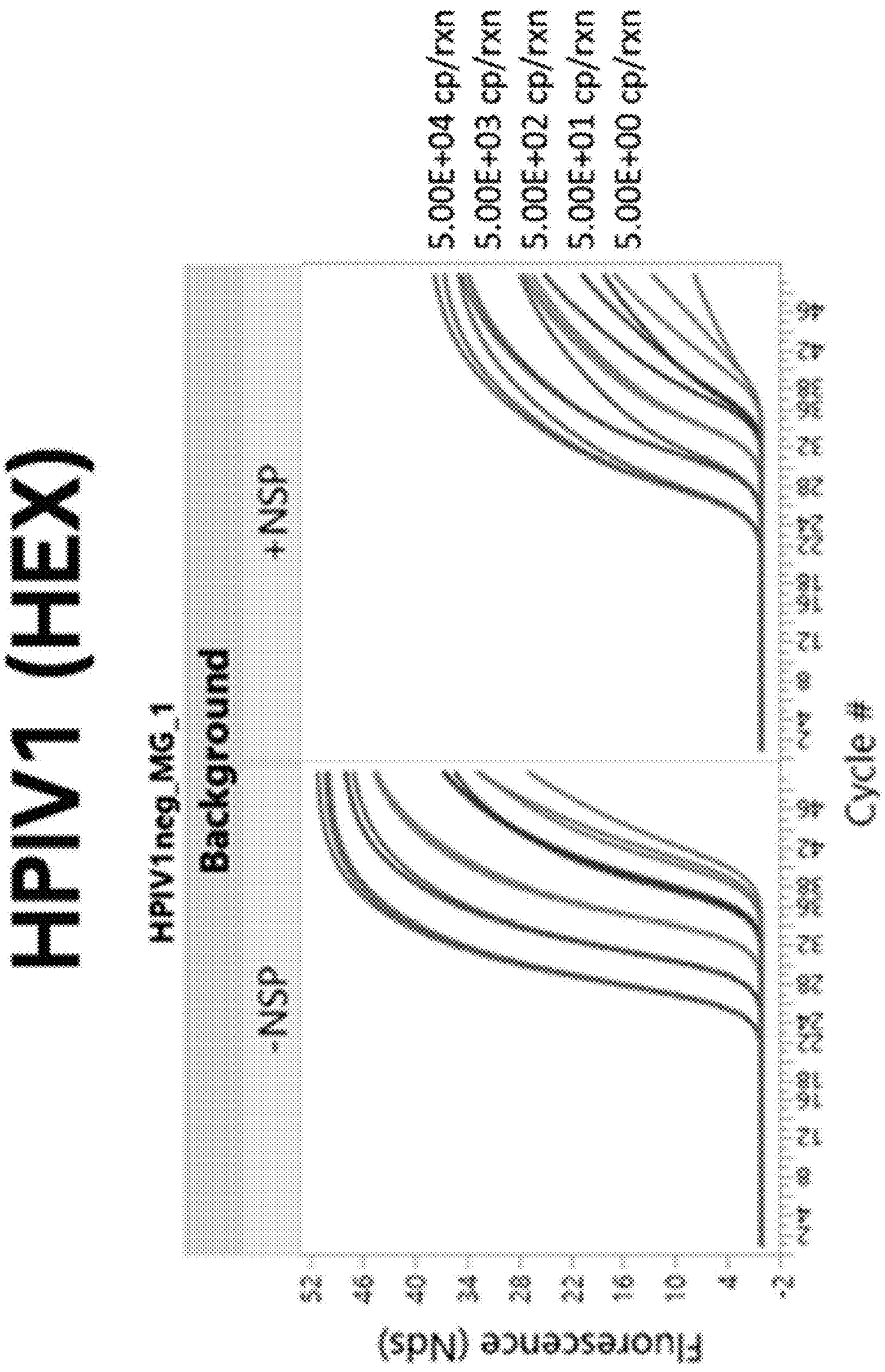
FIG. 18B (HPIV 1), FIG. 18C (HPIV 2), FIG. 18D (HPIV 3), and FIG. 18E (HPIV 4) show the PCR growth curves of a dilution series of the performance of the HPIV 1-4 multiplex assay in the contrived nasopharyngeal simulated clinical sample.
Figure 18C:
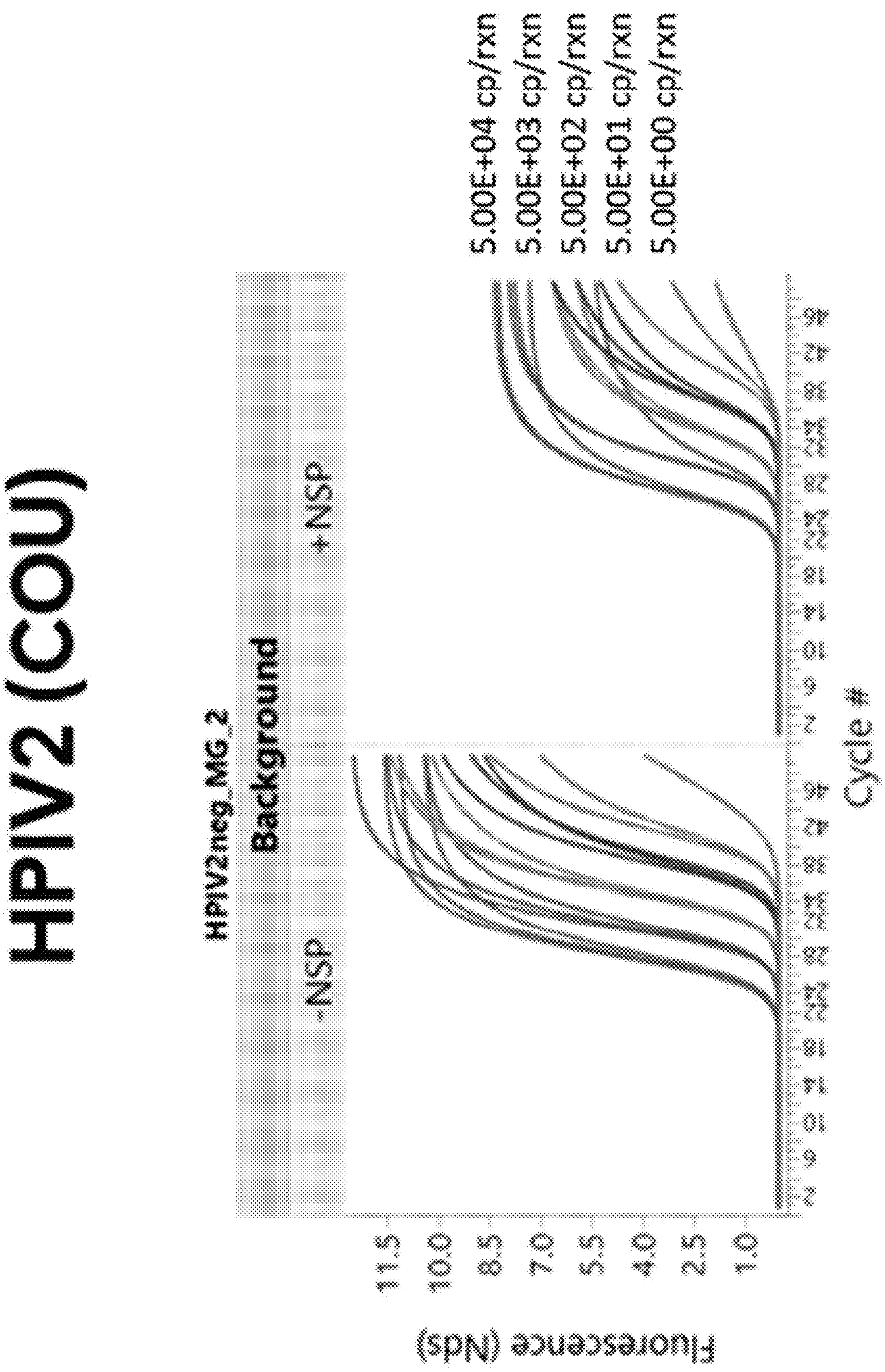
Figure 18D:
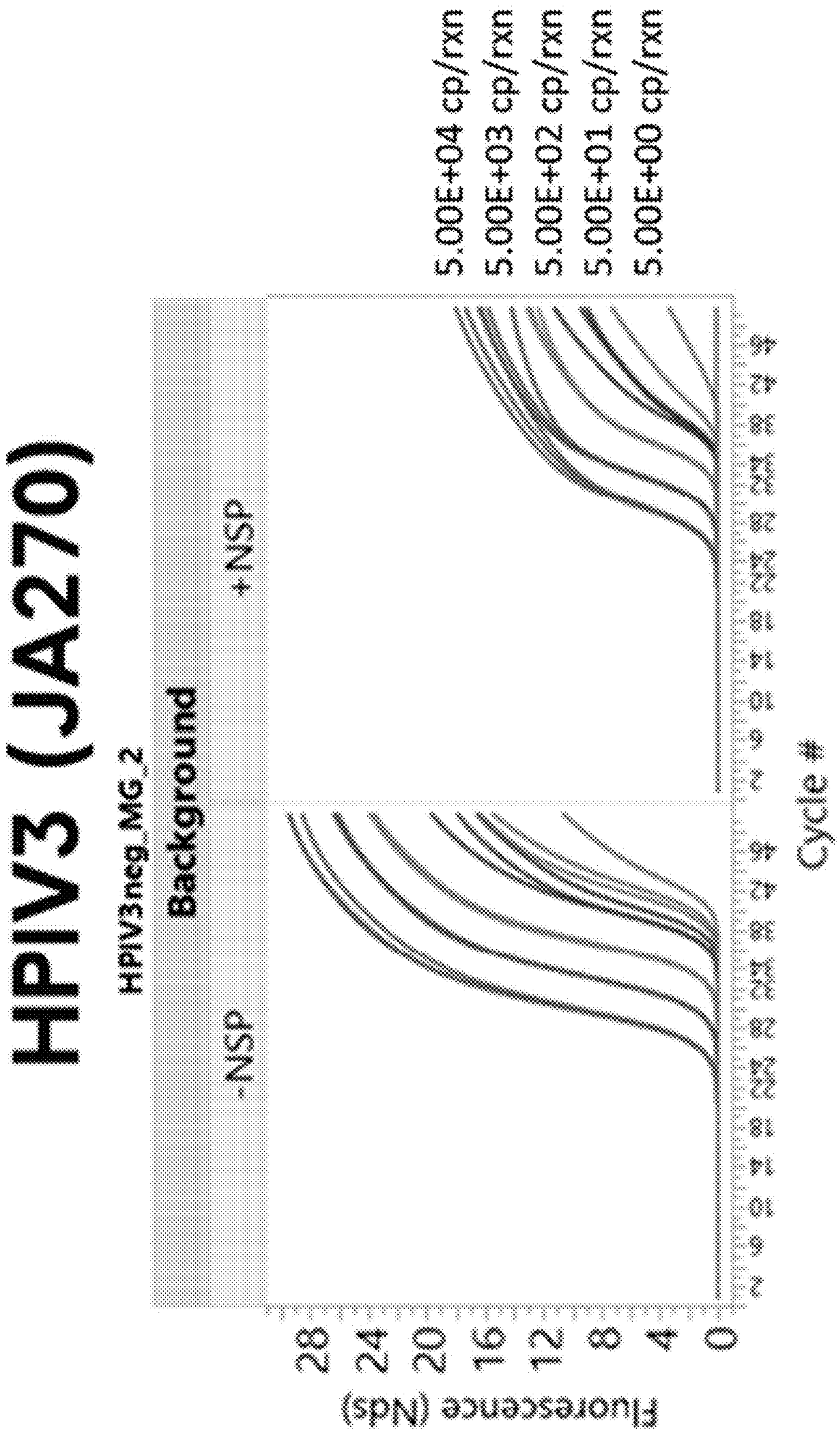
Figure 18E:
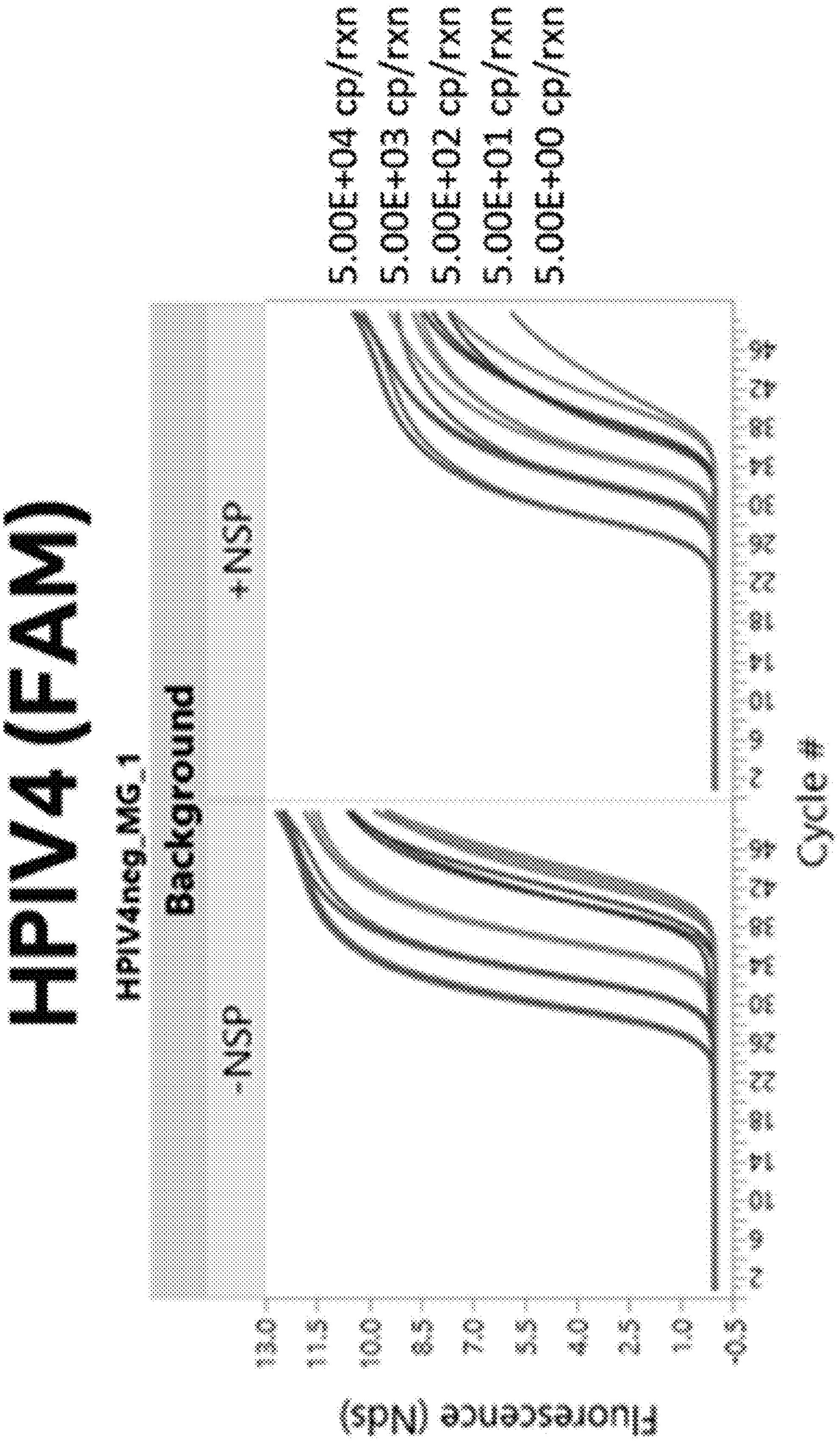

Example 12: HPIV 1-4 Primers and Probes Simultaneously Amplify and Detect Target HPIV 1-4 Nucleic Acids from a Contrived Nasopharyngeal Simulated Clinical Sample in an HPIV 1-4 Multiplex Real-Time PCR Assay HPIV 1-4 oligonucleotides were tested using primers/probes for detecting HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. The samples tested were tested in presence of contrived artificial nasopharyngeal matrix eluate, which was intended to simulate a clinical sample background, which would include cells, and mucin and were used at the following concentrations: $5\times10^0$, $\mathbf{5\times10}^1$, $\mathbf{5\times10}^2$, $\mathbf{5\times10}^3$, and $5\times10^4$ copies per reaction. The composition of the matrix is shown in FIG. 18A. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. The results are shown in FIG. 18B (HPIV 1), FIG. 18C (HPIV 2), FIG. 18D (HPIV 3), and FIG. 18E (HPIV 4), which shows PCR growth curves of a dilution series of the performance of a HPIV 1-4 assay. The results showed a sensitivity of the HPIV 1-4 types minimally up to 50 copies/reaction in the presence of the nasopharyngeal matrix. FIG. 18B, FIG. 18C, FIG. 18D, and FIG. 18E show that the HPIV 1-4 oligonucleotides are able to simultaneously amplify and detect target HPIV 1-4 nucleic acids from a contrived artificial nasopharyngeal simulated clinical sample in a multiplex setting. The data show that the HPIV 1-4 multiplex assay shows a sensitivity of four HPIV types minimally up to 50 copies/reaction in the presence of a nasopharyngeal background. Because the contrived artificial nasopharyngeal matrix simulates a nasopharyngeal clinical sample, these data suggest that the HPIV 1-4 oligonucleotides would be able to simultaneously amplify and detect target HPIV 1-4 nucleic acids from an actual nasopharyngeal sample.

Figure 19A:
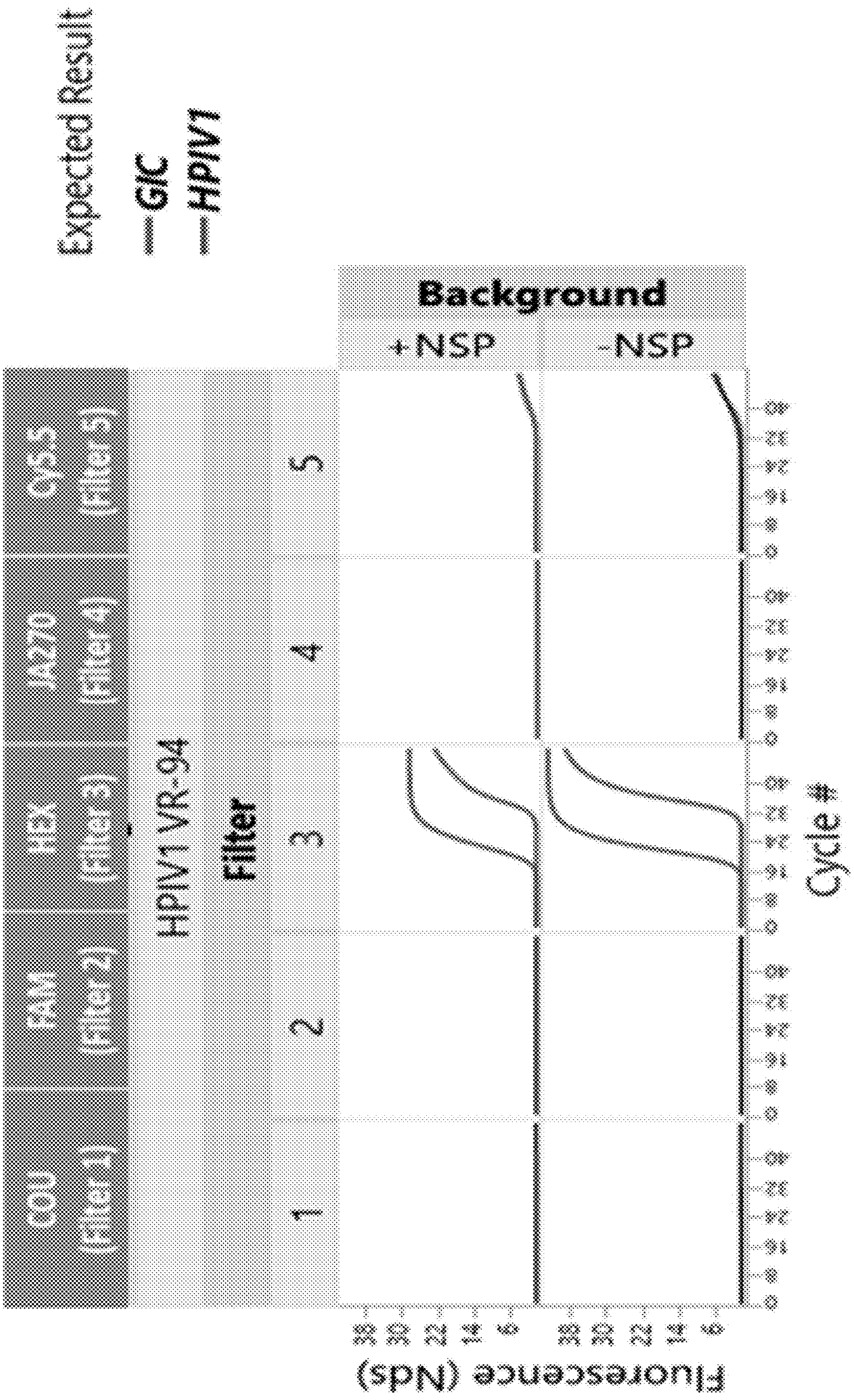
FIG. 19A, FIG. 19B, FIG. 19C, and FIG. 19D show that the HPIV 1-4 primers and probes simultaneously specifically detect target HPIV 1-4 nucleic acids from viral eluates in an HPIV 1-4 multiplex real-time PCR assay, as described in Example 13. HPIV 1-4 oligonucleotides were tested using primers/probes for detecting HPIV 1 (SEQ ID NOs:1-3), HPIV 2 (SEQ ID NOs:4-6), HPIV 3 (SEQ ID NOs:15-17), and HPIV 4 (SEQ ID NOs:11, 13, 18, and 19). The HPIV 1-4 oligonucleotides were tested under multiplex conditions, such that the sample was simultaneously subject to exposure to all oligonucleotides for HPIV 1-4. The results are shown in FIG. 19A (HPIV 1), FIG. 19B (HPIV 2), FIG. 19C (HPIV 3), and FIG. 19D (HPIV 4), which shows PCR growth curves of a dilution series of the performance of a HPIV 1-4 assay. These results show that the HPIV 1-4 oligonucleotides are specific for their intended respective targets. As can be seen in FIG. 19A, FIG. 19B, FIG. 19C, and FIG. 19D, no cross-reactivity was observed using these viral eluates in unintended channels for a specific HPIV type.
Figure 19B:
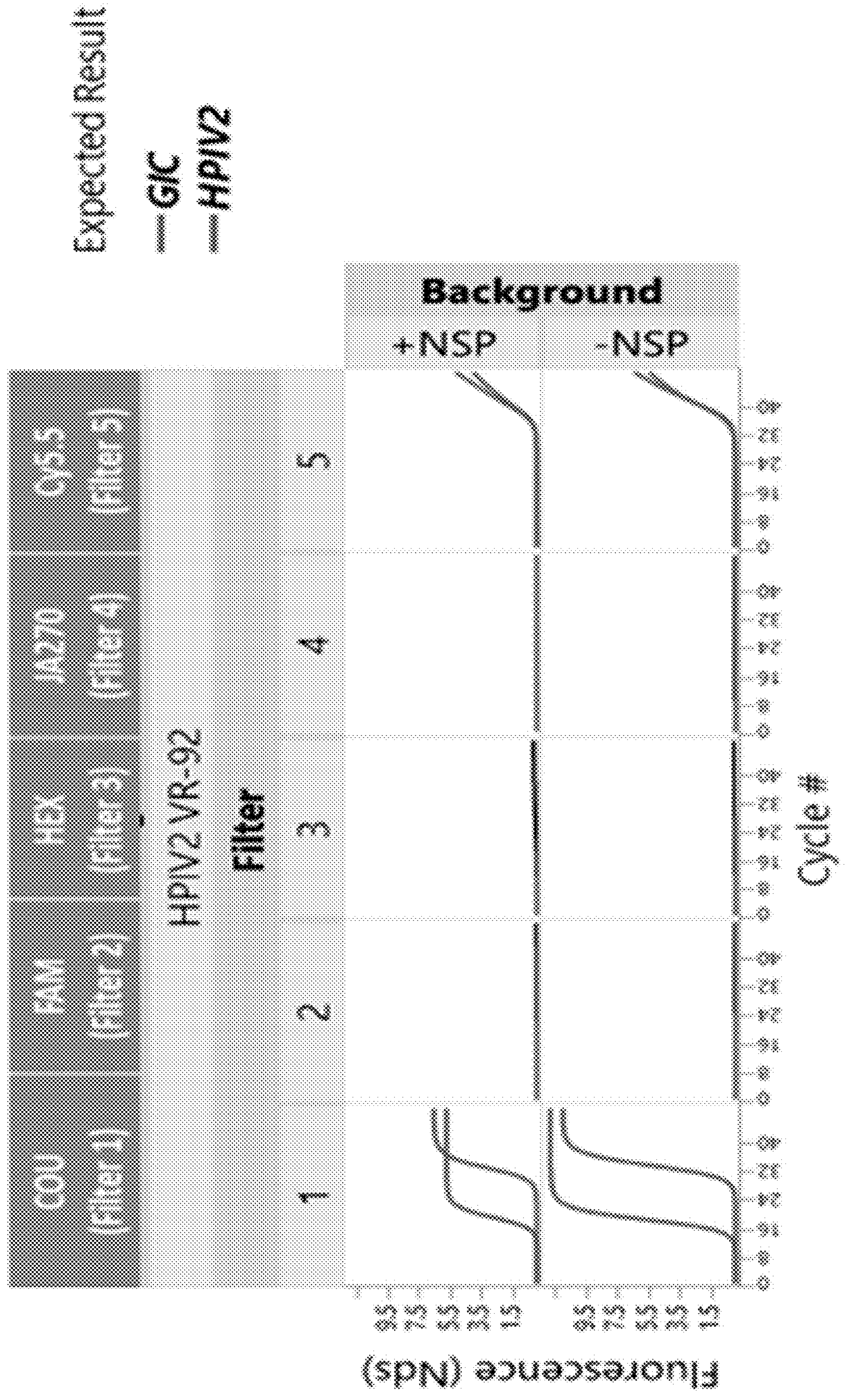
Figure 19C:
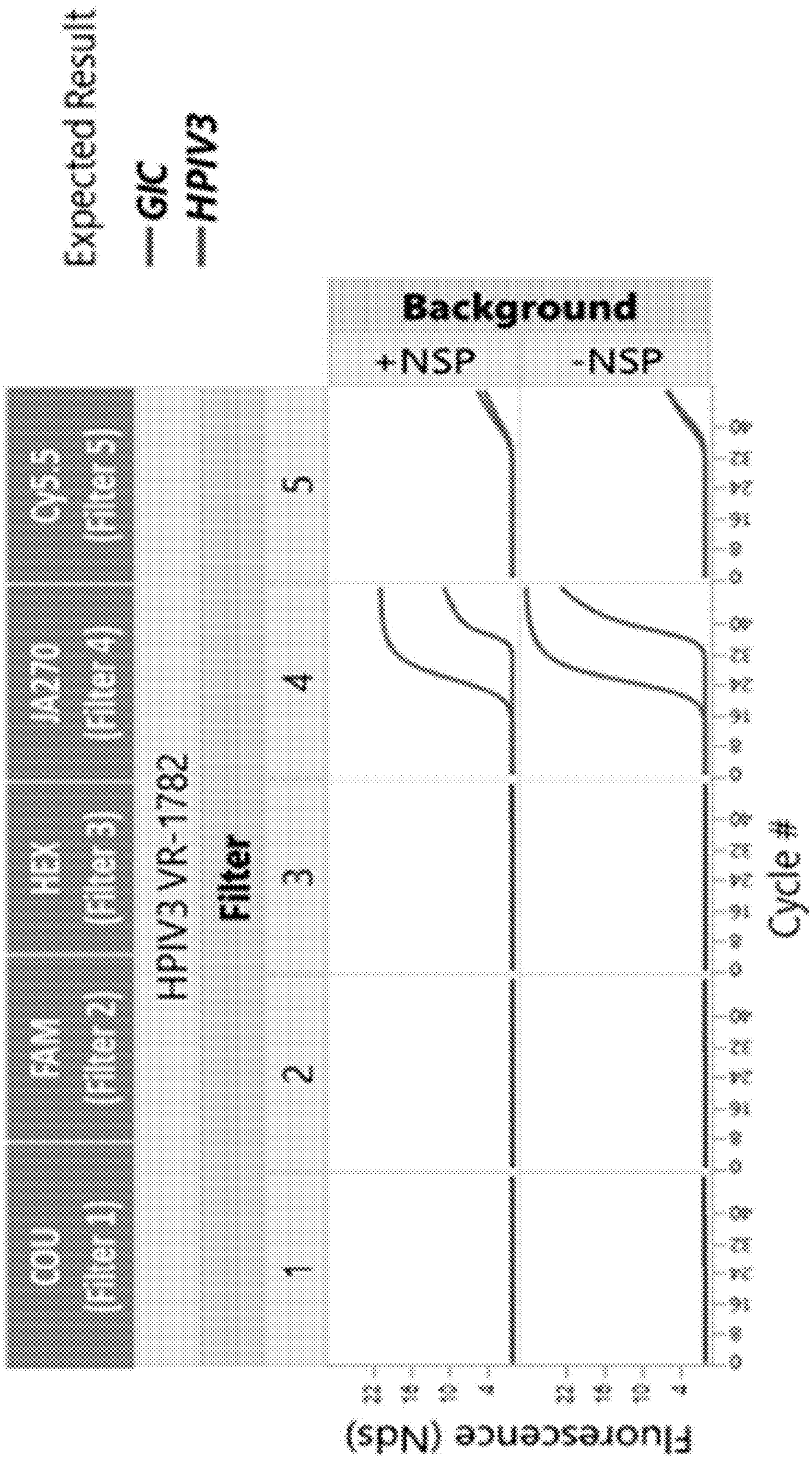
Figure 19D:
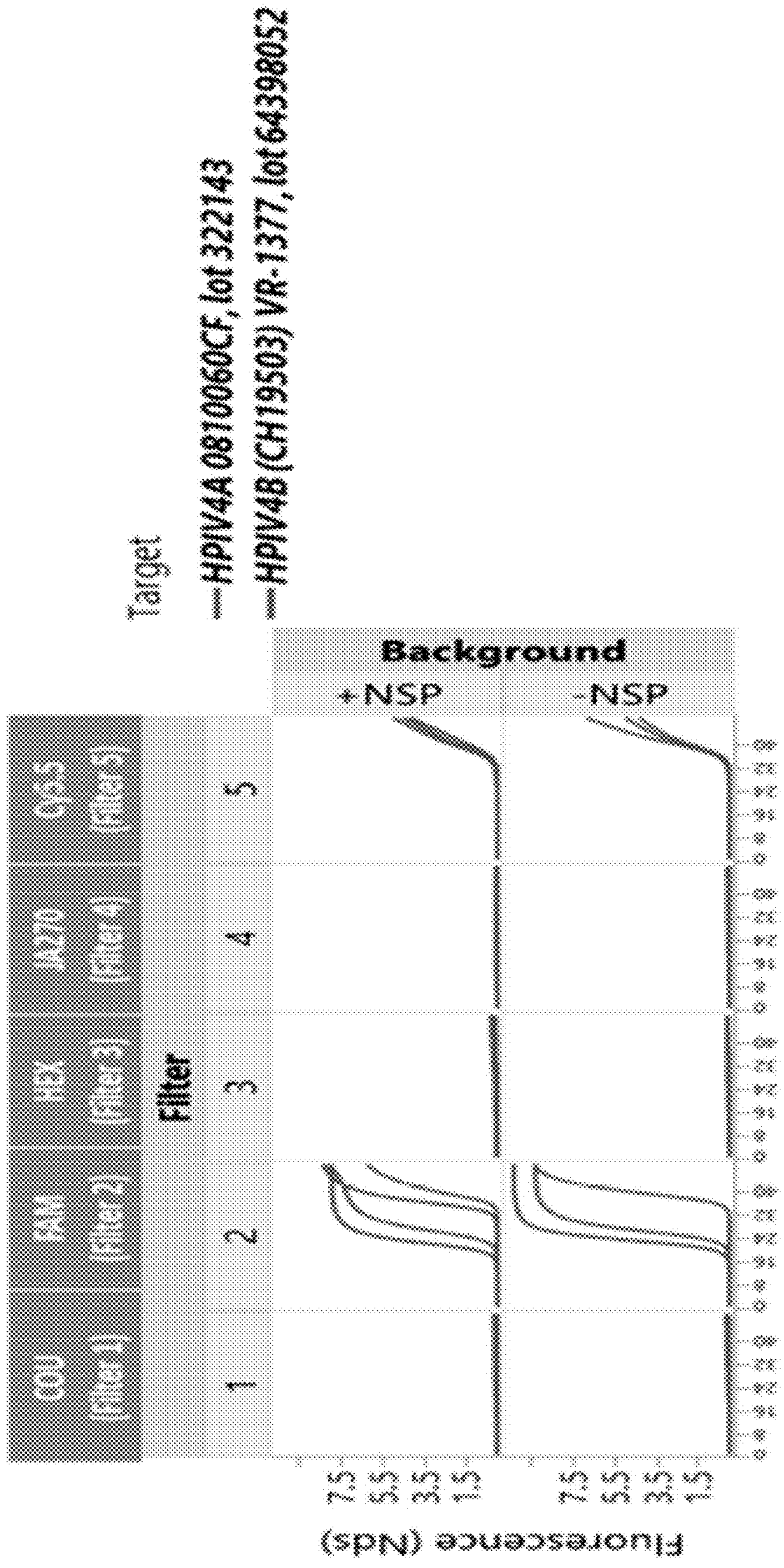

Example 13: HPIV 1-4 Primers and Probes Simultaneously Specifically Amplify and Detect Target HPIV 1-4 Nucleic Acids from Viral Eluates in an HPIV 1-4 Multiplex Real-Time PCR Assay HPIV 1-4 oligonucleotides were tested using primers/probes for detecting HPIV 1 (SEQ ID NOs:1-3), HPIV 2 (SEQ ID NO s:4-6), HPIV 3 (SEQ ID NOs:15-17), and HPIV 4 (SEQ ID NOs:11, 13, 18, and 19). The HPIV 1-4 oligonucleotides were tested under multiplex conditions, such that the sample was simultaneously subject to exposure to all oligonucleotides for HPIV 1-4. The oligonucleotides for the HPIV 1 assay were tested in the HEX channel, the oligonucleotides for the HPIV 2 assay were tested in the COU channel, the oligonucleotides for the HPIV 3 assay were tested in the JA270 channel, and the oligonucleotides for the HPIV 4 assay were tested in the FAM channel. The samples tested were viral eluates (ATCC Catalog No: HPIV1-VR-94; HPIV2-VR-92; HPIV3-VR-1782; HPIV-4B-VR1377); ZeptoMetrix Catalog No: HPIV4A-0810060CF), which were tested at two concentrations: neat and at a 1:100,000 dilution. Reagents used include Cobas® 6800/8800 generic PCR Master Mix, with the profile and conditions for use with the Cobas® 6800/8800, and using TaqMan® amplification and detection technology. The Cobas® 6800/8800 PCR Profile employed is shown in Table 2, above. These studies were designed to test the specificity of the HPIV 1-4 oligonucleotides on viral eluates. The results are shown in FIG. 19A (HPIV 1), FIG. 19B (HPIV 2), FIG. 19C (HPIV 3), and FIG. 19D (HPIV 4), which shows PCR growth curves of a dilution series of the performance of a HPIV 1-4 assay. These results show that the HPIV 1-4 oligonucleotides are specific for their intended respective targets. As can be seen in FIG. 19A, FIG. 19B, FIG. 19C, and FIG. 19D, no cross-reactivity was observed using these viral eluates in unintended channels for a specific HPIV type. Taken together, these studies demonstrate that the oligonucleotides for HPIV 1-4 specifically amplify and detect their intended targets in a multiplex setting.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method for detecting Human Parainfluenza Virus (HPIV) in a sample, wherein the HPIV comprises Human Parainfluenza Virus Type 1 (HPIV-1), Human Parainfluenza Virus Type 2 (HPIV-2), Human Parainfluenza Virus Type 3 (HPIV-3), and/or Human Parainfluenza Virus Type 4 (HPIV-4), the method comprising:

(a) performing an amplification step comprising contacting the sample with one or more set of primers to produce an amplification product of a target nucleic acid of HPIV-1, HPIV-2, HPIV-3, and/or HPIV-4, if one or more target nucleic acids of HPIV-1, HPIV-2, HPIV-3, and/or HPIV-4 is present in the sample;

(b) performing a hybridization step comprising contacting one or more probes with the amplification product of the target nucleic acid of HPIV-1, HPIV-2, HPIV-3, and/or HPIV-4, if the one or more target nucleic acids of HPIV-1, HPIV-2, HPIV-3, and/or HPIV-4 is present in the sample; and (c) detecting the presence or absence of the amplification product of the target nucleic acid of HPIV-1, HPIV-2, HPIV-3, and/or HPIV-4, wherein the presence of the amplification product of the target nucleic acid of HPIV-1, HPIV-2, HPIV-3, and/or HPIV-4 is indicative of the presence of HPIV-1, HPIV-2, HPIV-3, and/or HPIV-4, respectively, in the sample, and wherein the absence of the amplification product of the target nucleic acid of HPIV-1, HPIV-2, HPIV-3, and/or HPIV-4 is indicative of the absence of HPIV-1, HPIV-2, HPIV-3, and/or HPIV-4, respectively, from the sample; and wherein the one or more set of primers and the one or more probes comprises:

(1) a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO:3, or a complement thereof; and/or (2) a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO:7, or a complement thereof; and/or (3) a set of primers and a probe specific for target nucleic acids of HPIV-3, wherein the set of primers specific for target nucleic acids of HPIV-3 comprises a first primer comprising the nucleic acid sequence of SEQ ID NO:8, or a complement thereof, and a second primer comprising the nucleic acid sequence of SEQ ID NO:9, or a complement thereof; and wherein the probe specific for target nucleic acids of HPIV-3 comprises the nucleic acid sequence of SEQ ID NO: 10, or a complement thereof; and/or (4) a set of primers and a probe specific for target nucleic acids of HPIV-4, wherein the set of primers specific for target nucleic acids of HPIV-4 comprises a first primer comprising the nucleic acid sequence of SEQ ID NO: 11, or a complement thereof, a second primer comprising the nucleic acid sequence of SEQ ID NO: 12, or a complement thereof; and wherein the probe specific for target nucleic acids of HPIV-4 comprises the nucleic acid sequence of SEQ ID NO: 13, or a complement thereof.

2. The method of claim 1, wherein the sample is a biological sample.

3. The method of claim 2, wherein the biological sample is a nasopharyngeal sample.

4. The method of claim 1, wherein the one or more probes is labeled.

5. The method of claim 4, wherein the one or more probes is labeled with a donor fluorescent moiety and a corresponding acceptor moiety.

6. The method of claim 5, wherein detecting the presence or absence of the amplification product of the target nucleic acid of HPIV-1, HPIV-2, HPIV-3, and/or HPIV-4 in step (c) comprises detecting the presence or absence of fluorescent resonance energy transfer (FRET) between the donor fluorescent moiety and the acceptor moiety of the probes specific for the target nucleic acid of HPIV-1, HPIV-2, HPIV-3, and/or HPIV-4, wherein the presence or absence of fluorescence is indicative of the presence or absence of HPIV-1, HPIV-2, HPIV-3, and/or HPIV-4, respectively, in the sample.

7. A method for simultaneously detecting one or more target nucleic acids of HPIV-1, HPIV-2, HPIV-3, and/or HPIV-4 in a sample, the method comprising:

(a) performing an amplification step comprising contacting the sample with one or more set of primers to produce an amplification product of a target nucleic acid of HPIV-1, HPIV-2, HPIV-3, and/or HPIV-4, if one or more target nucleic acids of HPIV-1, HPIV-2, HPIV-3, and/or HPIV-4 is present in the sample;

(b) performing a hybridization step comprising contacting one or more probes with the amplification product of the target nucleic acid of HPIV-1, HPIV-2, HPIV-3, and/or HPIV-4, if the one or more target nucleic acids of HPIV-1, HPIV-2, HPIV-3, and/or HPIV-4 is present in the sample; and (c) detecting the presence or absence of the amplification product of the target nucleic acid of HPIV-1, HPIV-2, HPIV-3, and/or HPIV-4, wherein the presence of the amplification product of the target nucleic acid of HPIV-1, HPIV-2, HPIV-3, and/or HPIV-4 is indicative of the presence of HPIV-1, HPIV-2, HPIV-3, and/or HPIV-4, respectively, in the sample, and wherein the absence of the amplification product of the target nucleic acid of HPIV-1, HPIV-2, HPIV-3, and/or HPIV-4 is indicative of the absence of HPIV-1, HPIV-2, HPIV-3, and/or HPIV-4, respectively, from the sample; and wherein the one or more set of primers and the one or more probes comprises:

(1) a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO:3, or a complement thereof; and/or (2) a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO:7, or a complement thereof; and/or (3) a set of primers and a probe specific for target nucleic acids of HPIV-3, wherein the set of primers specific for target nucleic acids of HPIV-3 comprises a first primer comprising the nucleic acid sequence of SEQ ID NO:8, or a complement thereof, and a second primer comprising the nucleic acid sequence of SEQ ID NO:9, or a complement thereof; and wherein the probe specific for target nucleic acids of HPIV-3 comprises the nucleic acid sequence of SEQ ID NO:10, or a complement thereof; and/or (4) a set of primers and a probe specific for target nucleic acids of HPIV-4, wherein the set of primers specific for target nucleic acids of HPIV-4 comprises a first primer comprising the nucleic acid sequence of SEQ ID NO:11, or a complement thereof, a second primer comprising the nucleic acid sequence of SEQ ID NO: 12, or a complement thereof; and wherein the probe specific for target nucleic acids of HPIV-4 comprises the nucleic acid sequence of SEQ ID NO:13, or a complement thereof.

8. The method of claim 7, wherein the sample is a biological sample.

9. The method of claim 8, wherein the biological sample is a nasopharyngeal sample.

10. The method of claim 7, wherein the one or more probes is labeled.

11. The method of claim 10, wherein the one or more probes is labeled with a donor fluorescent moiety and a corresponding acceptor moiety.

12. The method of claim 11, wherein detecting the presence or absence of the amplification product of the target nucleic acid of HPIV-1, HPIV-2, HPIV-3, and/or HPIV-4 in step (c) comprises detecting the presence or absence of fluorescent resonance energy transfer (FRET) between the donor fluorescent moiety and the acceptor moiety of the probes specific for target nucleic acid of HPIV-1, HPIV-2, HPIV-3, and/or HPIV-4, wherein the presence or absence of fluorescence is indicative of the presence or absence of HPIV-1, HPIV-2, HPIV-3, and/or HPIV-4, respectively, in the sample.

13. A method for detecting a first target nucleic acid, second target nucleic acid, third target nucleic acid, and/or fourth target nucleic acid in a sample, if the first target nucleic acid, the second target nucleic acid, the third target nucleic acid, and/or the fourth target nucleic acid is present in the sample, the method comprising:

(a) performing an amplification step comprising contacting the sample with one or more set of primers to produce an amplification product of the first target nucleic acid, the second target nucleic acid, the third target nucleic acid, and/or the fourth target nucleic acid, if the first target nucleic acid, the second target nucleic acid, the third target nucleic acid, and/or the fourth target nucleic acid is present in the sample;

(b) performing a hybridization step comprising contacting the one or more probes with the amplification product, if the first target nucleic acid, the second target nucleic acid, the third target nucleic acid, and/or the fourth target nucleic acid is present in the sample; and (c) detecting the presence or absence of the amplification product of the first target nucleic acid, the second target nucleic acid, the third target nucleic acid, and/or the fourth target nucleic acid, wherein the presence of the amplification product of the first target nucleic acid, the second target nucleic acid, the third target nucleic acid, and/or the fourth target nucleic acid is indicative of the presence of the first target nucleic acid, the second target nucleic acid, the third target nucleic acid, and/or the fourth target nucleic acid, respectively, in the sample, and wherein the absence of the amplification product of the first target nucleic acid, the second target nucleic acid, the third target nucleic acid, and/or the fourth target nucleic acid is indicative of the absence of the first target nucleic acid, the second target nucleic acid, the third target nucleic acid, and/or the fourth target nucleic acid, respectively, in the sample; and wherein the one or more set of primers and the one or more probes comprises:

(1) a set of primers and a probe for the first target nucleic acid, wherein the set of primers for the first target nucleic acid comprises a first primer comprising the nucleic acid sequence of SEQ ID NO:1, or a complement thereof, and a second primer comprising the nucleic acid sequence of SEQ ID NO:2, or a complement thereof; and wherein the probe for the first target nucleic acid comprises the nucleic acid sequence of SEQ ID NO:3, or a complement thereof; and/or (2) a set of primers and a probe for the second target nucleic acid, wherein the set of primers for the second target nucleic acid comprises a first primer comprising the nucleic acid sequence of SEQ ID NO:4, or a complement thereof, and a second primer comprising the nucleic acid sequence of SEQ ID NO:5, or a complement thereof; and wherein the probe for the second target nucleic acid comprises the nucleic acid sequence of SEQ ID NO:7, or a complement thereof; and/or (3) a set of primers and a probe for the third target nucleic acid, wherein the set of primers for the third target nucleic acid comprises a first primer comprising the nucleic acid sequence of SEQ ID NO:8, or a complement thereof, and a second primer comprising the nucleic acid sequence of SEQ ID NO:9, or a complement thereof; and wherein the probe for the third target nucleic acid comprises the nucleic acid sequence of SEQ ID NO:10, or a complement thereof; and/or (4) a set of primers and a probe for the fourth target nucleic acid, wherein the set of primers for the fourth target nucleic acid comprises a first primer comprising the nucleic acid sequence of SEQ ID NO:11, or a complement thereof, and a second primer comprising the nucleic acid sequence of SEQ ID NO:12, or a complement thereof; and wherein the probe for the fourth target nucleic acid comprises the nucleic acid sequence of SEQ ID NO:13, or a complement thereof; and wherein the first target nucleic acid is a target nucleic acid of HPIV-1, wherein the second target nucleic acid is a target nucleic acid of HPIV-2, wherein the third target nucleic acid is a target nucleic acid of HPIV-3, and wherein the fourth target nucleic acid is a target nucleic acid of HPIV-4.

14. A method for simultaneously detecting a first target nucleic acid, second target nucleic acid, third target nucleic acid, and/or fourth target nucleic acid in a sample, if the first target nucleic acid, the second target nucleic acid, the third target nucleic acid, and/or the fourth target nucleic acid is present in the sample, the method comprising:

(a) performing an amplification step comprising contacting the sample with one or more set of primers to produce an amplification product of the first target nucleic acid, the second target nucleic acid, the third target nucleic acid, and/or the fourth target nucleic acid, if the first target nucleic acid, the second target nucleic acid, the third target nucleic acid, and/or the fourth target nucleic acid is present in the sample;

(b) performing a hybridization step comprising contacting the one or more probes with the amplification product of the first target nucleic acid, the second target nucleic acid, the third target nucleic acid, and/or the fourth target nucleic acid, if the first target nucleic acid, the second target nucleic acid, the third target nucleic acid, and/or the fourth target nucleic acid is present in the sample; and (c) detecting the presence or absence of the amplification product of the first target nucleic acid, the second target nucleic acid, the third target nucleic acid, and/or the fourth target nucleic acid, wherein the presence of the amplification product of the first target nucleic acid, the second target nucleic acid, the third target nucleic acid, and/or the fourth target nucleic acid is indicative of the presence of the first target nucleic acid, the second target nucleic acid, the third target nucleic acid, and/or the fourth target nucleic acid, respectively, in the sample, and wherein the absence of the amplification product of the first target nucleic acid, the second target nucleic acid, the third target nucleic acid, and/or the fourth target nucleic acid is indicative of the absence of the first target nucleic acid, the second target nucleic acid, the third target nucleic acid, and/or the fourth target nucleic acid, respectively, in the sample; and wherein the one or more set of primers and the one or more probes comprises:

(1) a set of primers and a probe for the first target nucleic acid, wherein the set of primers for the first target nucleic acid comprises a first primer comprising the nucleic acid sequence of SEQ ID NO:1, or a complement thereof, and a second primer comprising the nucleic acid sequence of SEQ ID NO:2, or a complement thereof; and wherein the probe for the first target nucleic acid comprises the nucleic acid sequence of SEQ ID NO:3, or a complement thereof;

(2) a set of primers and a probe for the second target nucleic acid, wherein the set of primers for the second target nucleic acid comprises a first primer comprising the nucleic acid sequence of SEQ ID NO:4, or a complement thereof, and a second primer comprising the nucleic acid sequence of SEQ ID NO:5, or a complement thereof; and wherein the probe for the second target nucleic acid comprises the nucleic acid sequence of SEQ ID NO:7, or a complement thereof;

(3) a set of primers and a probe for the third target nucleic acid, wherein the set of primers for the third target nucleic acid comprises a first primer comprising the nucleic acid sequence of SEQ ID NO:8, or a complement thereof, and a second primer comprising the nucleic acid sequence of SEQ ID NO:9, or a complement thereof; and wherein the probe for the third target nucleic acid comprises the nucleic acid sequence of SEQ ID NO:10, or a complement thereof, and (4) a set of primers and a probe for the fourth target nucleic acid, wherein the set of primers for the fourth target nucleic acid comprises a first primer comprising the nucleic acid sequence of SEQ ID NO: 11, or a complement thereof, and a second primer comprising the nucleic acid sequence of SEQ ID NO:12, or a complement thereof; and wherein the probe for the fourth target nucleic acid comprises the nucleic acid sequence of SEQ ID NO:13, or a complement thereof; and wherein the first target nucleic acid is a target nucleic acid of HPIV-1, wherein the second target nucleic acid is a target nucleic acid of HPIV-2, wherein the third target nucleic acid is a target nucleic acid of HPIV-3, and wherein the fourth target nucleic acid is a target nucleic acid of HPIV-4.

15. The method of claim 13 or 14, wherein the sample is a biological sample.

16. The method of claim 15, wherein the biological sample is a nasopharyngeal sample.

17. The method of claim 13 or 14, wherein the one or more probes is labeled.

18. The method of claim 17, wherein the one or more probes is labeled with a donor fluorescent moiety and a corresponding acceptor moiety.

19. The method of claim 18, wherein detecting the presence or absence of the amplification product of the first target nucleic acid, the second target nucleic acid, the third target nucleic acid, and/or the fourth target nucleic acid in step (c) comprises detecting the presence or absence of fluorescent resonance energy transfer (FRET) between the donor fluorescent moiety and the acceptor moiety of the probe for the first target nucleic acid, the second target nucleic acid, the third target nucleic acid, and/or the fourth target nucleic acid, wherein the presence of fluorescence is indicative of the presence of HPIV-1, HPIV-2, HPIV-3, and/or HPIV-4 in the sample, and the absence of fluorescence is indicative of the absence of HPIV-1, HPIV-2, HPIV-3, and/or HPIV-4 in the sample.

20. A kit for detecting HPIV that may be present in a sample, wherein the HPIV comprises HPIV-1, HPIV-2, HPIV-3, and/or HPIV-4, the kit comprising amplification and detection reagents, wherein the amplification and detection reagents comprise: (i) a DNA polymerase; (ii) nucleotide monomers; and (iii) one or more set of primers and one or more probes, wherein the one or more set of primers and the one or more probes comprises:

(1) a set of primers and a probe specific for target nucleic acids of HPIV-1, wherein the set of primers specific for target nucleic acids of HPIV-1 comprises a first primer comprising the nucleic acid sequence of SEQ ID NO:1, or a complement thereof, and a second primer comprising the nucleic acid sequence of SEQ ID NO:2, or a complement thereof; and wherein the probe specific for target nucleic acids of HPIV-1 comprises the nucleic acid sequence of SEQ ID NO: 3, or a complement thereof, and/or (2) a set of primers and a probe specific for target nucleic acids of HPIV-2, wherein the set of primers specific for target nucleic acids of HPIV-2 comprises a first primer comprising the nucleic acid sequence of SEQ ID NO:4, or a complement thereof, and a second primer comprising the nucleic acid sequence of SEQ ID NO:5, or a complement thereof; and wherein the probe specific for target nucleic acids of HPIV-2 comprises the nucleic acid sequence of SEQ ID NO: 7, or a complement thereof; and/or (3) a set of primers and a probe specific for target nucleic acids of HPIV-3, wherein the set of primers specific for target nucleic acids of HPIV-3 comprises a first primer comprising the nucleic acid sequence of SEQ ID NO:8, or a complement thereof, and a second primer comprising the nucleic acid sequence of SEQ ID NO:9, or a complement thereof; and wherein the probe specific for target nucleic acids of HPIV-3 comprises the nucleic acid sequence of SEQ ID NO: 10, or a complement thereof; and/or (4) a set of primers and a probe specific for target nucleic acids of HPIV-4, wherein the set of primers specific for target nucleic acids of HPIV-4 comprises a first primer comprising the nucleic acid sequence of SEQ ID NO:11, or a complement thereof, and a second primer comprising the nucleic acid sequence of SEQ ID NO: 12, or a complement thereof; and wherein the probe specific for target nucleic acids of HPIV-4 comprises the nucleic acid sequence of SEQ ID NO: 13, or a complement thereof.

21. The kit of claim 20, wherein the sample is a biological sample.

22. The kit of claim 21, wherein the biological sample is a nasopharyngeal sample.

23. The kit of claim 20, wherein the one or more probes is labeled.

24. The kit of claim 23, wherein the one or more probes is labeled with a donor fluorescent moiety and a corresponding acceptor moiety.

25. A kit for simultaneous detection of a target nucleic acid of HPIV-1, HPIV-2, HPIV-3, and/or HPIV-4 in a sample, if a target nucleic acid of HPIV-1, HPIV-2, HPIV-3, and/or HPIV-4 is present in the sample, the kit comprising amplification and detection reagents, wherein the amplification and detection reagents comprise: (i) a DNA polymerase; (ii) nucleotide monomers; and (iii) one or more set of primers and one or more probes, wherein the one or more set of primers and the one or more probes comprises:

(1) a set of primers and a probe specific for target nucleic acids of HPIV-1, wherein the set of primers comprises a first primer comprising the nucleic acid sequence of SEQ ID NO: 1, or a complement thereof, and a second primer comprising the nucleic acid sequence of SEQ ID NO:2, or a complement thereof, and wherein the probe comprises the nucleic acid sequence of SEQ ID NO:3, or a complement thereof;

(2) a set of primers and a probe specific for target nucleic acids of HPIV-2, wherein the set of primers comprises a first primer comprising the nucleic acid sequence of SEQ ID NO: 4, or a complement thereof, and a second primer comprising the nucleic acid sequence of SEQ ID NO:5, or a complement thereof; and wherein the probe comprises the nucleic acid sequence of SEQ ID NO:7, or a complement thereof;

(3) a set of primers and a probe specific for target nucleic acids of HPIV-3, wherein the set of primers comprises a first primer comprising the nucleic acid sequence of SEQ ID NO: 8, or a complement thereof, and a second primer comprising the nucleic acid sequence of SEQ ID NO:9, or a complement thereof; and wherein the probe comprises the nucleic acid sequence of SEQ ID NO: 10, or a complement thereof; and (4) a set of primers and a probe specific for target nucleic acids of HPIV-4, wherein the set of primers comprises a first primer comprising the nucleic acid sequence of SEQ ID NO: 11, or a complement thereof, and a second primer comprising the nucleic acid sequence of SEQ ID NO: 12, or a complement thereof; and wherein the probe comprises the nucleic acid sequence of SEQ ID NO: 13, or a complement thereof.

26. The kit of claim 25, wherein the sample is a biological sample.

27. The kit of claim 26, wherein the biological sample is a nasopharyngeal sample.

28. The kit of claim 25, wherein the one or more probes is labeled.

29. The kit of claim 28, wherein the one or more probes is labeled with a donor fluorescent moiety and a corresponding acceptor moiety.

* * * * *

SEQUENCE LISTING

```
<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 1

tcaggtgtta attcttgtga tctcaa                                          26


<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

tgacccagga ttcccattga a                                               21


<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (6)..(7)
<223> OTHER INFORMATION: BHQ-2

<400> SEQUENCE: 3

tcgtgacatt attcaatttc ttccctacca gtgcca                               36


<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gttaagatat ccctagagca acttca                                          26


<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

tgagtataac tagaaaatgc ataggaacta                                      30


<210> SEQ ID NO 6
<211> LENGTH: 40
<212> TYPE: DNA
<213> ORGANISM: Artificial Sequence
```

<220> FEATURE:
<223> OTHER INFORMATION: Description of Artificial Sequence: Synthetic
      probe
<220> FEATURE:
<221> NAME/KEY: misc_feature
<222> LOCATION: (6)..(7)
<223> OTHER INFORMATION: BHQ-2

<400> SEQUENCE: 6
tggctccatc atctaaacgg tgtgtaatat ttgcagatgt 40

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (6)..(7)
<223> OTHER INFORMATION: BHQ-2

<400> SEQUENCE: 7
ttaagtgttg tggctccatc atctaaacgg tgtgtaat 38

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcagaaatg atctcacaac ca 22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggatagagtc aaagctgcca ttc 23

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (11)..(12)
<223> OTHER INFORMATION: BHQ-2

<400> SEQUENCE: 10
ttgttggtaa ctacataaga gatgcaggtc tcgct 35

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ggtggtattc aaatagatct tgagc 25

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
tcattatcac caaaagccca aatatatac 29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
probe
<220> FEATURE:
<221> NAME/KEY: misc_feature
<222> LOCATION: (6)..(7)
<223> OTHER INFORMATION: BHQ-2

<400> SEQUENCE: 13
agattttgag aagcacctgg tatttgggcc 30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
probe
<220> FEATURE:
<221> NAME/KEY: misc_feature
<222> LOCATION: (6)..(7)
<223> OTHER INFORMATION: BHQ-2

<400> SEQUENCE: 14
agattttgag aagcacctgg tatttgggcc 30

<210> SEQ ID NO 15
<211> LENGTH: 450
<212> TYPE: DNA
<213> ORGANISM: Human parainfluenza virus 1

<400> SEQUENCE: 15
tgcaatcctg atcacactat aatgttcatg taagaccacc tgatcacatt tgtgttctcc 60
gccttccatg tcacaatgaa taaaccctat tgaattattc tgtaattcat tccagattag 120
tgtttcacat tcatcattcc ctatccaagt tgacccagga ttcccattga ataaaacctt 180 gacccttga cataaactcg tgacattatt caatttcttc cctaccagtg ccacttctga 240
aggataaata tttaattctc tttgtccgtt gagatcacaa gaattaacac ctgaattgta 300
atagttcatg cagggtccta atgtagcatc ataacaagac agcattgcac ctgcaccttc 360
tccgagatat aatctatctt tatccttatt gactagagga ttcagtaaat aggtaagttc 420
taaaaaaaaa aaaaaaaaaa aaaaaaaaaa 450

<210> SEQ ID NO 16

<211> LENGTH: 442
<212> TYPE: DNA
<213> ORGANISM: Human parainfluenza virus 2

<400> SEQUENCE: 16
ttaaaggtgc cacacacagt ttgaaggctg ctcttagggg cgcaggggta tatatttggg 60
catttgggga tactatagtg aactggaatg atgcacttga tattgcaaat actagagtta 120
agatatccct agagcaactt cagactctta cacctcttcc tacatctgca aatattacac 180
accgtttaga tgatggagcc acaacactta aattcactcc agctagttcc tatgcatttt 240
ctagttatac tcatatatca aatgatcaac aatatttaga aatagatcag agagtagttg 300
attccaatat tatttatcaa caattaatga taacaggact tgggatcatt gagacctacc 360
ataacccacc tataagaact tctacacaag aaatcactct ccatttgcac aaaaaaaaaa 420
aaaaaaaaaa aaaaaaaaaa cc 442

<210> SEQ ID NO 17
<211> LENGTH: 696
<212> TYPE: DNA
<213> ORGANISM: Human parainfluenza virus 3

<400> SEQUENCE: 17
aaccaaaccg actctgacgg cagtttacga gagagatgat agggtctgct tcagtaagcc 60
agatgctaca caattaggct tgtacatatt gtcgttagaa cgcggctaca attaatacat 120
aaccttatgt atcatacaca tacgatttag gtgacactat agaatacaag cttcattgca 180
taactccata tggcaggata gttgcctggt gcgaactcac catgtatggg atctctgagg 240
atacagatga atggagcgcg tggtcccttt gacaaataca gttccattag agcttttaat 300
ctattgatat ccggtctgag agtggataga gtcaaagctg ccattctagt ctcaattcca 360
tatctgattg tattgaagaa tgaagcgaga cctgcatctc ttatgtagtt accaacaatt 420
tgtatattct tttctatggt tgtgagatca tttctgctag tattcattgt tattaacgtc 480
tcaaccataa gagttaccaa gctctgttgg gaccgcatga ttgacccaat ctgatccact 540
gtgtcaccgc tcaacaccag ccctgcctgc actgttccat cttgtctgaa agcttccaat 600
cgagtgaaaa aaaaaaaaaa aaaaaaaaaa aaaaaccgaa ttcgtaatca tgtcatagct 660
gtttcctgtg tgaaattgtt atccgctcac aattcc 696

<210> SEQ ID NO 18
<211> LENGTH: 664
<212> TYPE: DNA
<213> ORGANISM: Human parainfluenza virus 4

<400> SEQUENCE: 18
cgactctgac ggcagtttac gagagagatg atagggtctg cttcagtaag ccagatgcta 60
cacaattagg cttgtacata ttgtcgttag aacgcggcta caattaatac ataaccttat 120
gtatcataca catacgattt aggtgacact atagaataca agcttcttgc aggtgtaaat 180
ttcatctgag ttactccgtc atctagccga tgggtcaaat ttgctgaagt aggtagagga 240
gttagtactc tgagctgatc taaagttata tttacacgtg tcttagacag ttcgtatgca 300
tcttgccaat tctgttcatt atcaccaaaa gcccaaatat atacgccagt tagccttaaa 360
actgacttta gattttgaga agcacctggt atttgggcca atgatgcaat tcttcgttca 420
tctgtttttg aaccaatata tggaactctc ataggtggat ttttgcttgg ctcaagatct 480
atttgaatac cacccggtaa ataaagccaa gtaaacttat cattacctga tgcacattga 540

-continued

```
tgacacaaag atttatttgt taacaagact ccatcaaaaa aaaaaaaaaa aaaaaaaaaa    600

aaaaccgaat tcgtaatcat gtcatagctg tttcctgtgt gaaattgtta tccgctcaca    660

attc                                                                  664
```